(12) United States Patent
Sueyoshi et al.

(10) Patent No.: US 10,613,314 B2
(45) Date of Patent: Apr. 7, 2020

(54) OBLIQUE VIEWING ENDOSCOPE AND IMAGING SYSTEM

(71) Applicant: PANASONIC I-PRO SENSING SOLUTIONS CO., LTD., Fukuoka (JP)

(72) Inventors: Masafumi Sueyoshi, Kanagawa (JP); Yuichi Hatase, Fukuoka (JP)

(73) Assignee: PANASONIC I-PRO SENSING SOLUTIONS CO., LTD., Fukuoka (JP)

( * ) Notice: Subject to any disclaimer, the term of this patent is extended or adjusted under 35 U.S.C. 154(b) by 0 days.

(21) Appl. No.: 16/134,347

(22) Filed: Sep. 18, 2018

(65) Prior Publication Data

US 2019/0086657 A1 Mar. 21, 2019

(30) Foreign Application Priority Data

Sep. 19, 2017 (JP) .................. 2017-179424

(51) Int. Cl.
*G02B 23/24* (2006.01)
*A61B 1/00* (2006.01)
*A61B 1/05* (2006.01)
*H04N 9/04* (2006.01)
(Continued)

(52) U.S. Cl.
CPC ........ *G02B 23/243* (2013.01); *A61B 1/00009* (2013.01); *A61B 1/00096* (2013.01); *A61B 1/00179* (2013.01); *A61B 1/00195* (2013.01); *A61B 1/05* (2013.01); *A61B 1/051* (2013.01); *A61B 1/07* (2013.01); *G02B 23/2423* (2013.01); *G02B 23/2484* (2013.01);
(Continued)

(58) Field of Classification Search
CPC combination set(s) only.
See application file for complete search history.

(56) References Cited

U.S. PATENT DOCUMENTS 6,636,254 B1 * 10/2003 Onishi .................. A61B 1/0005
348/65
7,280,283 B1 * 10/2007 Kasai .................. A61B 1/00179
359/656
(Continued)

FOREIGN PATENT DOCUMENTS

| JP | 2002-318353 A | 10/2002 |
| JP | 2010-097208 A | 4/2010 |
| JP | 5430482 B | 12/2013 |

OTHER PUBLICATIONS

U.S. Appl. No. 16/126,670 to Seiji Higashiyama et al., filed Sep. 10, 2018.

*Primary Examiner* — Janese Duley
(74) *Attorney, Agent, or Firm* — Greenblum & Bernstein P.L.C.

(57) ABSTRACT

An oblique viewing endoscope has an aperture through which some rays out of rays reflected from an object in an oblique viewing direction pass, an imaging element that captures an image, based on image forming of the rays passing through the aperture, and a lens that is disposed between the aperture and the imaging element, and that has a lens surface on which the image is formed by causing some rays in at least a visual field center out of the rays passing through the aperture in the oblique viewing direction to be substantially vertically incident on a center of the imaging element.

7 Claims, 44 Drawing Sheets

(51) Int. Cl.
*A61B 1/07* (2006.01)
*H04N 5/225* (2006.01)

(52) U.S. Cl.
CPC ....... *H04N 5/2254* (2013.01); *H04N 9/04517* (2018.08); *H04N 2005/2255* (2013.01)

(56) References Cited

U.S. PATENT DOCUMENTS

2010/0076268 A1 3/2010 Takasugi et al.
2017/0049305 A1* 2/2017 Takasugi ................ G02B 13/04

* cited by examiner

OBLIQUE VIEWING ENDOSCOPE AND IMAGING SYSTEM

BACKGROUND

1. Technical Field

The present disclosure relates to an oblique viewing endoscope and an imaging system which have a forward oblique viewing optical system.

2. Description of the Related Art

In the related art, as an imaging device, a lateral viewing-type medical endoscope (hereinafter, referred to as an "oblique viewing endoscope") is known which can observe a body cavity of a human body or an inner wall surface of a tube. For example, Japanese Patent Unexamined Publication No. 2010-97208 (PTL 1) discloses an oblique viewing endoscope including a forward oblique viewing optical system.

FIG. 43 is a layout view of the forward oblique viewing optical system in the related art. As illustrated in FIG. 43, in the oblique viewing endoscope, objective system 2A2 which is the forward oblique viewing optical system has prism PA2 for a forward oblique viewing angle of 45°. Front lens group G1 having positive refractive power is located between an object and prism PA2. Rear lens group G2 having the positive refractive power is located between prism PA2 and CCD 501 which is an imaging element. Aperture S is located on a front side of prism PA2.

SUMMARY

However, according to the oblique viewing endoscopes in the related art as disclosed in PTL 1, rays reflected from the object are transmitted through front lens group G1. Thereafter, the rays are redirected by being reflected on prism PA2. After the rays are further transmitted through rear lens group G2, the rays form an image on CCD 501. Therefore, the oblique viewing endoscope in the related art needs a large number of components, thereby causing a problem in that a structure for a distal end portion is less likely to be miniaturized.

On the other hand, for example, as in an endoscope image-forming optical system disclosed in Japanese Patent Unexamined Publication No. 2002-318353 (PTL 2), in order to observe the object in an oblique direction, there is a method of partially using a super wide angle lens by shifting a visual field. In a case of the endoscope image-forming optical system, the imaging element is located far away from an optical axis of the lens. Consequently, there is a problem in that a maximum outer diameter of the endoscope becomes large.

If the super wide angle lens is miniaturized, an angle of the rays emitted from the lens becomes large. FIG. 44 is a plan view of an optical system in the related art, in which the imaging element is shifted in a horizontal direction. That is, in FIG. 44, a center of an imaging plane of imaging element 501 is shifted in a rightward direction (upward direction of a paper surface in FIG. 44) with respect to an axial line at the center of super wide angle lens 503.

If super wide angle lens 503 is used for the miniaturized optical system by shifting imaging element 501, incident light on imaging element 501 forms an incident angle which is greatly asymmetric with respect to the center of the imaging plane of imaging element 501. Here, imaging element 501 is generally designed and configured so that the incident light is vertically incident on the center of the imaging plane and a large incident angle is allowed as the incident light is incident on a periphery away from the center of the imaging plane.

FIG. 45 is a view for describing a ray example from the center of the imaging plane to each periphery in the shifted imaging element. In imaging element 501, the incident angle is configured so that efficiency is maximized at approximately 30 degrees in utmost periphery 505, for example. FIG. 46 is a view for describing a correlation between the incident angle and an image height in the shifted imaging element. As described above, in a case of imaging element 501 whose pupil is corrected to a central object so that the center is shifted 0 degrees and the periphery is shifted 20 to 30 degrees, if the incident light is greatly deviated from design value characteristic 507 due to shifted imaging element 501, the light is not partially effectively used, and a screen partially becomes dark. In order to avoid this problem, if an image side is set to an optical system close to a telecentric system, a lens system becomes large, thereby causing a problem in that an outer diameter of the endoscope becomes large. Types of the respective rays (a long broken line, a short broken line, and two-dot chain line) in FIGS. 45 and 46 correspond to each other.

The present disclosure is devised in view of the above-described circumstances in the related art, and an object thereof is to provide an imaging device, an oblique viewing endoscope, and an imaging system, which can be miniaturized and can capture an image in a forward oblique visual field direction while minimizing the number of components.

According to an aspect of the present disclosure, there is provided an oblique viewing endoscope including an aperture, a lens including a free curve surface having positive power, and an imaging element that captures an image formed by the lens including the free curve surface having the positive power. Rays passed through a center of the aperture and incident on a center of the imaging element are incident in an oblique viewing direction, are bent by the lens including the free curve surface having the positive power, and are substantially vertically incident on the imaging element.

According to another aspect of the present disclosure, there is provided an imaging system including an imaging device and a correction processor that performs correction processing on an image signal imaged by the imaging device.

According to the present disclosure, the oblique viewing endoscope and the imaging system can be miniaturized and the visual field direction can be obliquely set, while the number of components is minimized.

DETAILED DESCRIPTION

Hereinafter, each exemplary embodiment of an oblique viewing endoscope and an imaging system according to the present disclosure will be described in detail with reference to the drawings as appropriate. The oblique viewing endoscope is one optical device or optical instrument configuring oblique viewing endoscope system 11 (an example of an imaging system). However, unnecessarily detailed description may be omitted in some cases. For example, detailed description for already well-known items or repeated description for substantially the same configurations may be omitted in some cases. The reason is to avoid the following description from becoming unnecessarily redundant, and to facilitate understanding of those skilled in the art. The accompanying drawings and the following description are provided in order to enable those skilled in the art to sufficiently understand the present disclosure, and are not intended to limit the gist described in the appended claims.

Exemplary Embodiment 1

Figure 1:
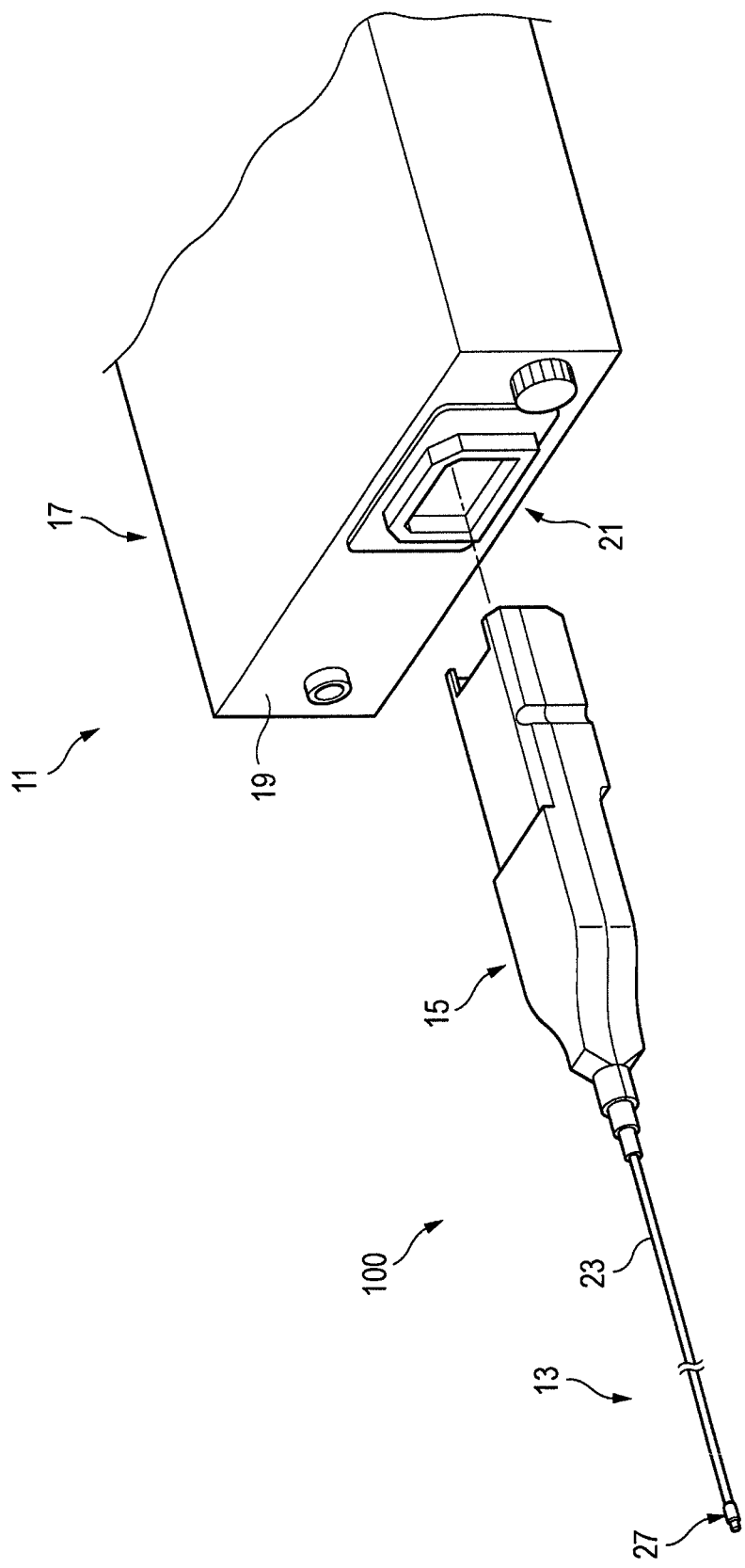
FIG. 1 is an overall configuration diagram illustrating an example of an oblique viewing endoscope system using an oblique viewing endoscope according to Exemplary Embodiment 1.

FIG. 1 is an overall configuration diagram illustrating an example of oblique viewing endoscope system 11 using oblique viewing endoscope 100 according to Exemplary Embodiment 1.

For example, oblique viewing endoscope system 11 is configured to include elongated oblique viewing endoscope 100 which is a flexible mirror for medical uses, and a console (not illustrated) which performs known image processing on a still image or a moving image obtained by imaging an interior of an observation target (for example, a blood vessel of a human body). Oblique viewing endoscope 100 includes insertion portion 13 located on one end side (front side) in a longitudinal direction which is inserted into the observation target, and a plug 15 to which a rear portion of insertion portion 13 is connected.

A cable (not illustrated) is connected to the console. Repeater 17 is attached to a distal end of the cable. Repeater 17 has a socket portion 21 disposed on front surface panel 19. A rear portion of plug 15 connected to oblique viewing endoscope 100 via the cable is inserted into socket portion 21. Oblique viewing endoscope 100 can transmit or receive power and various signals (video signals or control signals) and can transmit illumination light to or from the console via repeater 17.

The power and various signals described above are introduced from plug 15 to repeater 17 via transmission cable 25 (refer to FIG. 2) inserted into flexible portion 23. Image data output by the imaging element disposed in distal end portion 27 is transmitted to the console via repeater 17. The console performs image processing such as color correction or gradation correction on the image data transmitted from imaging element 29, and outputs the image data obtained after the image processing to a display device (not illustrated) of the console. The display device is a monitor device having a display device such as a liquid crystal display panel, and displays an image of a subject imaged by oblique viewing endoscope 100 (for example, the image data showing a state of a vascular inner wall of a human body serving as the subject).

In oblique viewing endoscope system 11, a control circuit of the console has a correction processor (not illustrated) which performs correction processing (in particular, correcting a color for magnification chromatic aberration) on an imaging signal (image signal) of a distorted optical image captured by imaging element 29.

Insertion portion 13 has flexible soft portion 23, to a rear end of which plug 15 is connected, and distal end portion 27 connected to a distal end of soft portion 23. Soft portion 23 connects plug 15 and distal end portion 27 to each other. Soft portion 23 has a proper length corresponding to methods of various endoscopic examinations or endoscopic surgeries. For example, soft portion 23 is configured so that an outer periphery of a thin metal sheet wound in a spiral shape is covered with a net and the outer periphery is further coated, and is formed to be sufficiently flexible.

Oblique viewing endoscope 100 according to the present exemplary embodiment, which will be described below, can be inserted into a body cavity having a small diameter by forming the small diameter. The body cavity having the small diameter is not limited to the blood vessel of the human body, and includes a ureter, a pancreatic duct, a bile duct, and a bronchiole, for example. That is, oblique viewing endoscope 100 can be inserted into the vessel, the ureter, the pancreatic duct, the bile duct, and the bronchiole of the human body. In other words, oblique viewing endoscope 100 can be used in observing vascular lesions. Oblique viewing endoscope 100 is effectively used in identifying an atherosclerotic plaque. Oblique viewing endoscope 100 is also applicable to observation at the time of cardiac catheter examinations. Furthermore, oblique viewing endoscope 100 is also effectively used in detecting a thrombus or an arteriosclerotic yellow plaque. For arteriosclerotic lesions, a color tone (white color, pale yellow color, or yellow color) or a surface (smooth or irregular) is observed. For the thrombus, a color tone (red color, white color, dark red color, yellow color, brown color, or mixed color) is observed.

Oblique viewing endoscope 100 can be used for observation when diagnosing and treating renal pelvis/ureter cancers and idiopathic renal bleeding. In this case, oblique viewing endoscope 100 is inserted into a bladder from a urethra, and is further moved forward into the ureter. In this manner, it is possible to internally observe the ureter and the renal pelvis.

Oblique viewing endoscope 100 can be inserted into a Vater's papilla which is open to a duodenum. A bile is generated from a liver, and passes through the bile duct. A pancreatic juice is generated from a pancreas, and passes through the pancreatic duct. Both of these are discharged from the Vater's papilla present in the duodenum. Oblique viewing endoscope 100 is inserted from the Vater's papilla serving as an opening of the bile duct and the pancreatic duct so as to enable the bile duct or the pancreatic duct to be observed.

Furthermore, oblique viewing endoscope 100 can be inserted into a bronchus. Oblique viewing endoscope 100 is inserted through an oral cavity or a nasal cavity of an examination body (that is, a treatment target person) who is at a supine position. Oblique viewing endoscope 100 passes through a pharynx and a larynx, and is inserted into a trachea while a vocal cord is visually checked. A bronchial tube is narrowed each time the bronchial tube is branched. For example, according to oblique viewing endoscope 100 whose maximum outer diameter is smaller than 2 mm, it is possible to check a lumen leading to a subsegmental bronchus.

Figure 2:
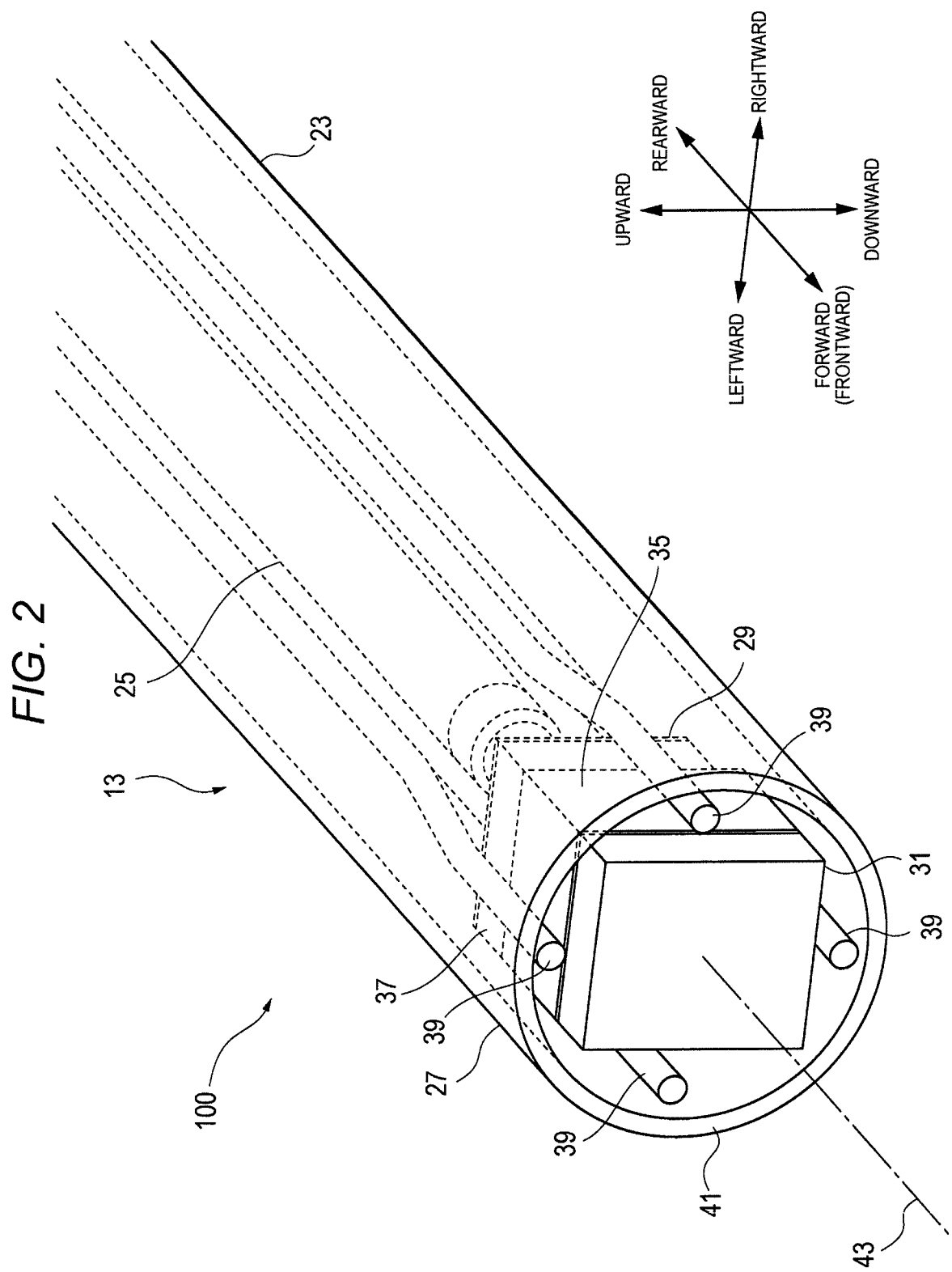
FIG. 2 is a perspective view when a distal end portion of the oblique viewing endoscope according to Exemplary Embodiment 1 is viewed from a front side.

FIG. 2 is a perspective view when distal end portion 27 of oblique viewing endoscope 100 according to Exemplary Embodiment 1 is viewed from the front side.

Directions used in the description herein will be respectively referred to as an "upward direction", a "downward direction", a "forward (frontward) direction, and a "rearward direction" which are directions of arrows illustrated in FIG. 2. Here, the "forward (frontward) direction" and the "rearward direction" respectively correspond to the distal side of insertion portion 13 and the proximal side of plug 15 in the oblique viewing endoscope.

Oblique viewing endoscope 100 according to the present exemplary embodiment has objective cover glass 31, aperture 33, lens 35, element cover glass 37, imaging element 29, transmission cable 25, optical fiber 39, and sheath 41.

In oblique viewing endoscope 100, objective cover glass 31, aperture 33, lens 35, element cover glass 37, and imaging element 29 are fixed by being integrally covered with a mold resin, and the outside covered with the mold resin is further covered with sheath 41. Oblique viewing endoscope 100 may have an optical column and a holder instead of the mold resin. However, from a viewpoint of reducing the diameter, it is more preferable to adopt a covering structure which is integrally molded using the mold resin instead of the optical column.

As an adhesion resin, the mold resin covers at least imaging element 29 and lens 35 so as to continuously cover a clearance portion therebetween. Accordingly, the mold resin is continuously molded from objective cover glass 31 throughout imaging element 29, thereby contributing to an increase in fixing strength of these optical systems. Mold resin improves airtightness, watertightness, and a light-blocking property of the clearance portion. Furthermore, the mold resin also improves the light-blocking property when light guide optical fiber 39 is incorporated therein. Therefore, as the mold resin, it is desirable to adopt a black resin containing carbon particles. In this manner, stray light from the outside can be prevented from being incident on imaging element 29.

Figure 3:
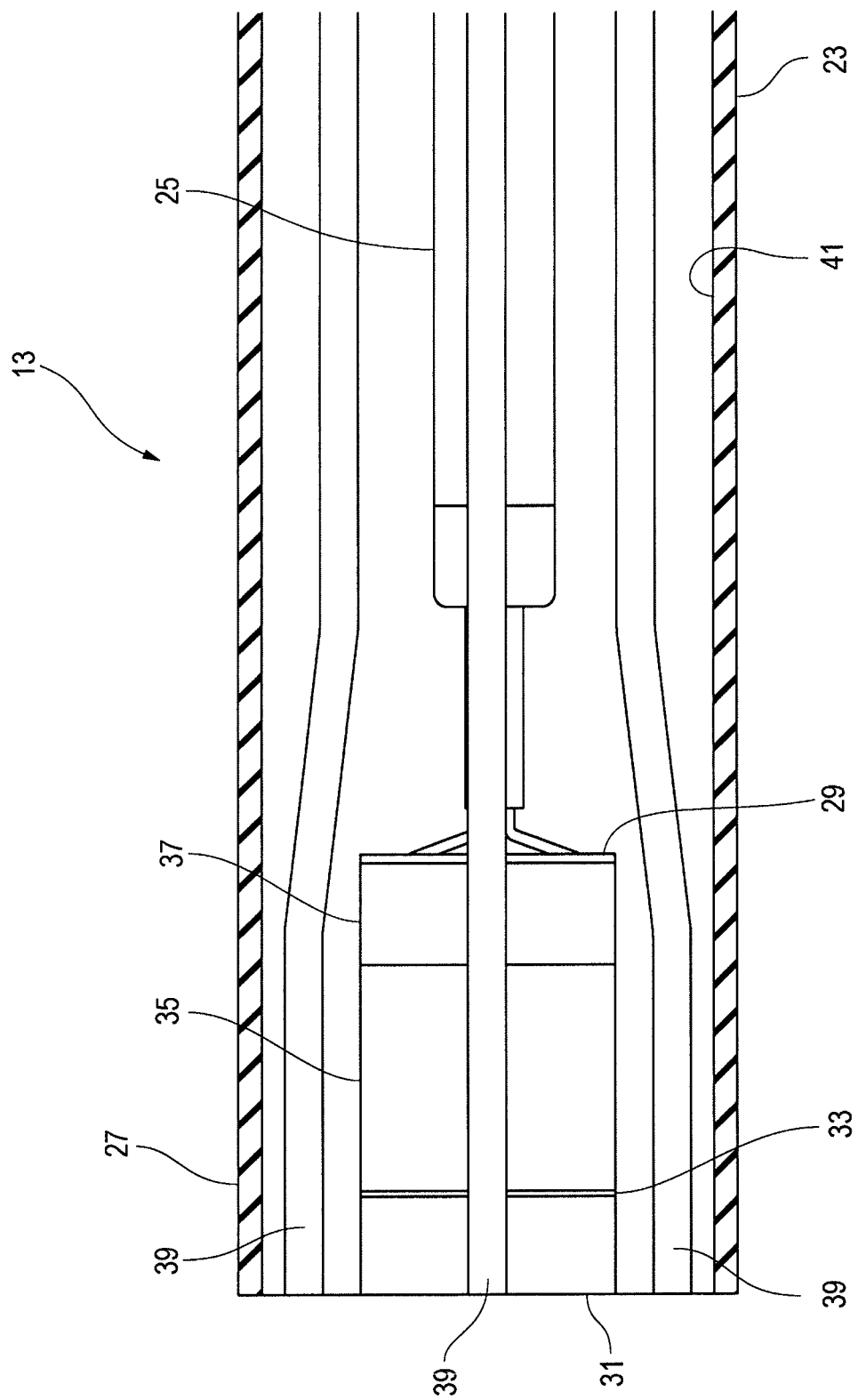
FIG. 3 is a plan view of a sheath interior of the oblique viewing endoscope according to Exemplary Embodiment 1.

FIG. 3 is a plan view of a sheath interior of oblique viewing endoscope 100 according to Exemplary Embodiment 1.

Sheath 41 is connected to distal end portion 27 formed in a cylindrical shape by using the mold resin in which objective cover glass 31 and optical fiber 39 are incorporated. As a connection structure between distal end portion 27 and sheath 41, sheath 41 having the same outer diameter can be connected to the rear end of distal end portion 27. In this case, sheath 41 can be fitted to the outer periphery of the small diameter portion formed in the rear end of distal end portion 27. As the connection structure between distal end portion 27 and sheath 41, both of these may be connected to each other by inserting the outer periphery of distal end portion 27 into the inner periphery of sheath 41. From a viewpoint of reducing the diameter and improving the connection strength, it is more preferable to fit sheath 41 to the outer periphery of the small diameter portion formed in the rear end of distal end portion 27. For example, the inner diameter side of sheath 41 is fixed to the outer periphery of the small diameter portion by using an adhesive.

For example, sheath 41 is configured to include a flexible resin material. In order to improve the strength, the inner peripheral side of sheath 41 can be provided with a single wire, a plurality of wires, or a braided tensile strength wire. As an example, the tensile strength wire includes aramid fiber such as poly-p-phenylene terephthalamide fiber, polyester-based fiber such as polyarylate fiber, polyparaphenylene benzbisoxazole fiber, and polyethylene terephthalate fiber, or nylon fiber.

Figure 4:
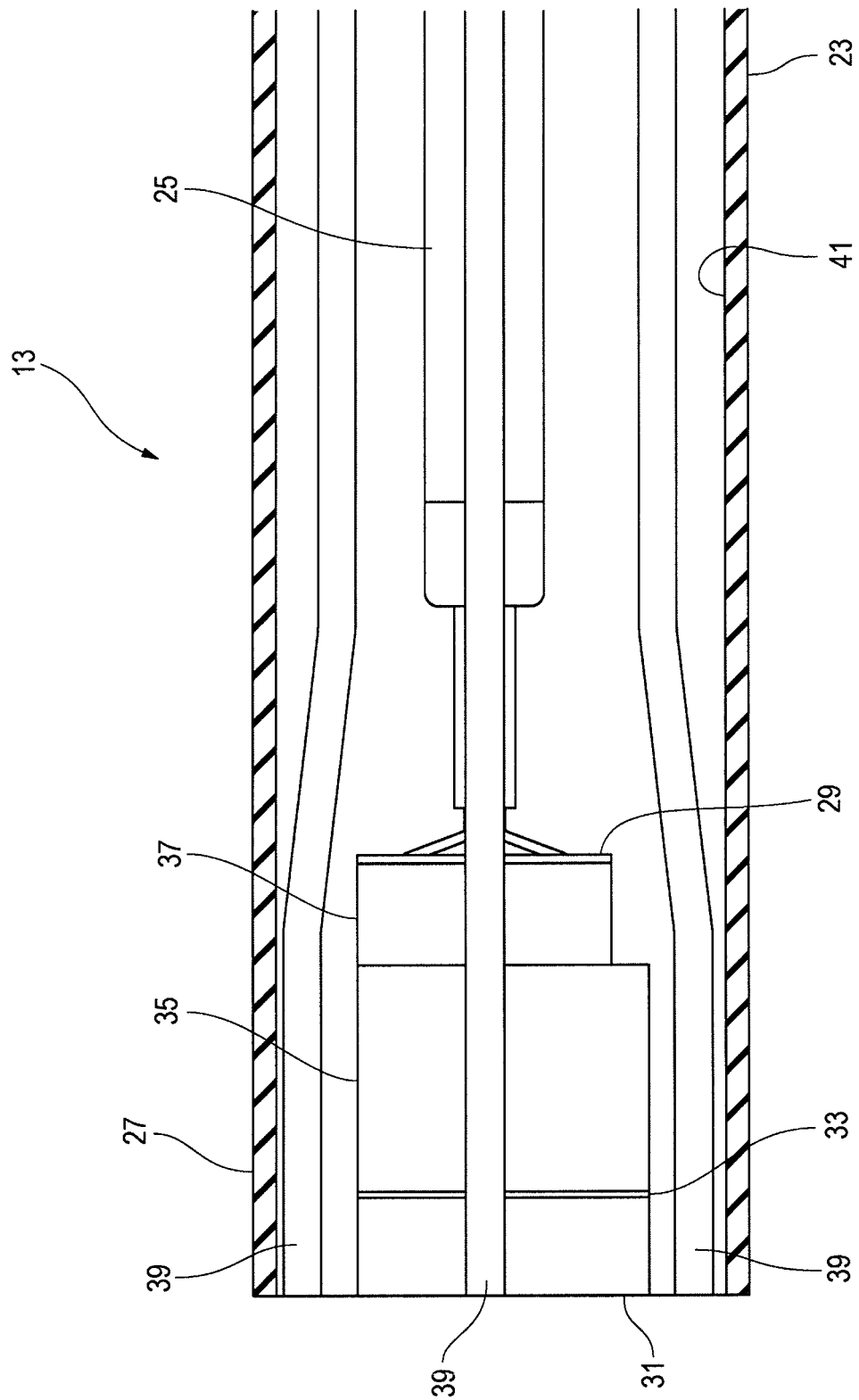
FIG. 4 is a side view of the sheath interior of the oblique viewing endoscope according to Exemplary Embodiment 1.

FIG. 4 is a side view of the sheath interior of oblique viewing endoscope 100 according to Exemplary Embodiment 1.

In oblique viewing endoscope 100, objective cover glass 31 and lens 35 are formed in the same oblong shape which is longitudinally long in a front view. On the other hand, element cover glass 37 and imaging element 29 are formed in the same square shape. Lens 35 and element cover glass 37 are connected to each other so that upper end surfaces are on the same plane (for example, flush). Therefore, a stepped portion in which lens 35 protrudes downward is formed between the lower end surface of lens 35 and the lower end surface of element cover glass 37.

In oblique viewing endoscope 100 according to the present exemplary embodiment, lens 35 is formed in a shape which is further expanded in a downward direction (visual field direction) than element cover glass 37 in this way. In oblique viewing endoscope 100, the expanded shape of lens 35 suppresses a decrease in an effective luminous flux in the visual field direction tilting forward and downward. Accordingly, oblique viewing endoscope 100 has the stepped portion. In this manner, it is possible to suppress the occurrence of so-called shading which is vignetting caused by the lower edge of objective cover glass 31 or lens 35.

Figure 5:
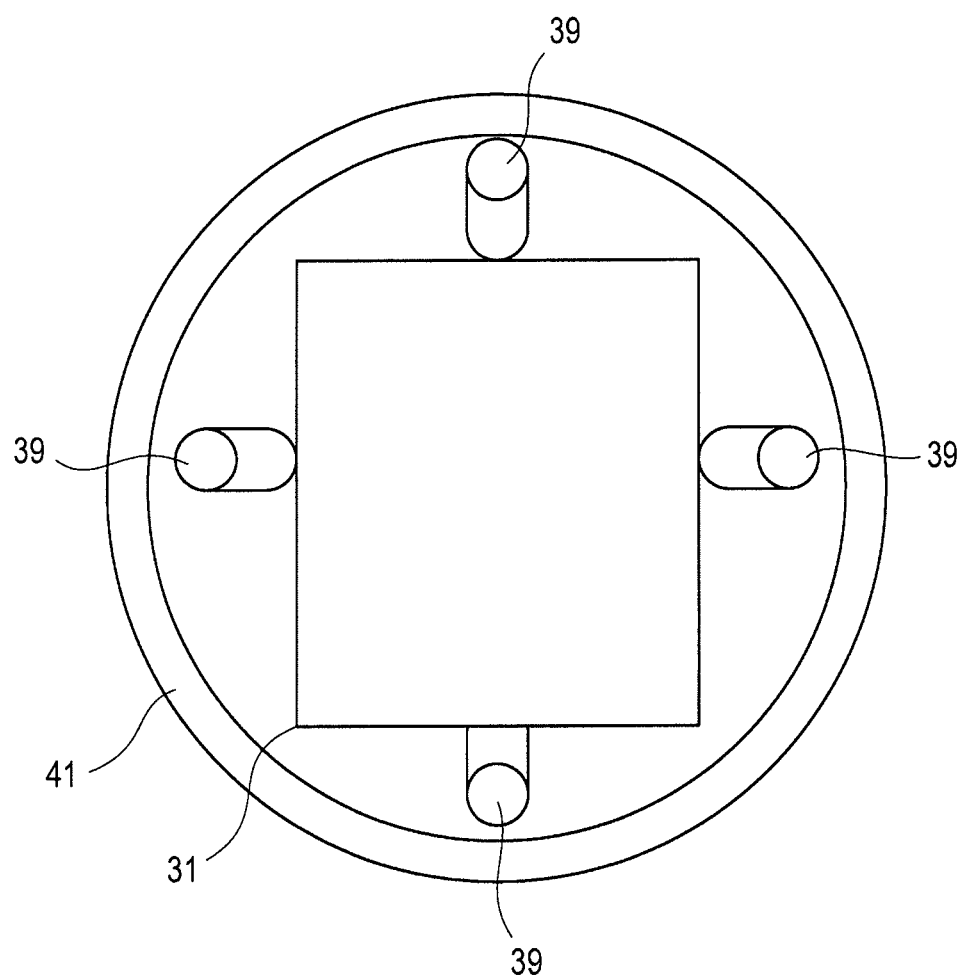
FIG. 5 is a front view of the sheath interior of the oblique viewing endoscope according to Exemplary Embodiment 1.

FIG. 5 is a front view of the sheath interior of oblique viewing endoscope 100 according to Exemplary Embodiment 1.

For example, as optical fiber 39, a plastic optical fiber (POF) is preferably used. The plastic optical fiber is formed of a material containing a silicone resin or an acrylic resin, and both a core and a clad are formed of plastic. For example, optical fiber 39 may be a bundle fiber in which a plurality of optical fiber wires are bundled and terminal fittings are attached to both ends thereof. The distal end of optical fiber 39 is distal end portion 27 serving as a light emitting end surface, and the proximal end of optical fiber 39 is connected to a ferrule of plug 15. For example, a light source is an LED disposed in socket portion 21. In oblique viewing endoscope 100, plug 15 is connected to socket portion 21. In this manner, the light emitted from the LED is propagated to optical fiber 39, and is emitted from the distal end. According to this configuration, a configuration from the light source to the light emitting end of the illumination light can be adopted using one optical fiber 39, and thus, light loss can be minimized.

Therefore, according to oblique viewing endoscope 100, since optical fiber 39 is provided, it is possible to independently capture an image in a dark place.

A plurality of optical fibers 39 are provided in the circumferential direction of sheath 41. Four optical fibers 39 can be provided at a substantially equal interval in the circumferential direction. In oblique viewing endoscope 100, objective cover glass 31 is formed in a rectangular shape. Four optical fibers 39 are arranged at substantially the center in each of four spaces interposed between sheath 41 surrounding objective cover glass 31 and each side portion of objective cover glass 31.

According to this configuration, it is possible to effectively use a crescent-shaped space formed by being interposed between objective cover glass 31 having a rectangular shape and sheath 41 having a circular shape. As a result, a plurality (particularly four) of optical fibers 39 can be easily arranged without increasing the outer diameter of distal end portion 27. In oblique viewing endoscope 100, optical fiber 39 has a layout in this way. Accordingly, it is possible to obtain a clear image while manufacture is facilitated without increasing the outer diameter of distal end portion 27.

For example, the visual field direction of oblique viewing endoscope 100 can be set to a downward direction in which a dip angle (dip) is 30°. Therefore, a configuration may be adopted as follows. Among four optical fibers 39 illustrated in FIG. 5, one upper optical fiber 39 having a lower illumination effect on the subject is omitted, and three optical fibers 39 are used. According to oblique viewing endoscope 100 using three optical fibers 39, the number of components can be minimized. Therefore, it is possible to realize a structure whose cost is reduced, whose weight is reduced, and which is likely to be flexible.

In the description herein, the dip angle of the visual field direction is used to facilitate the understanding of the operation. When oblique viewing endoscope 100 is actually used, oblique viewing endoscope 100 is rotated at any desired angle of 360° so as to observe the interior of the tube. Therefore, in a case where oblique viewing endoscope 100 is rotated 180°, the dip angle is read as an elevation angle (angle of elevation). In the description herein, the visual field direction of "oblique viewing" means a "direction of an angle formed by a principal ray in the visual field direction with respect to axial line 43 (refer to FIG. 2) of distal end portion 27". That is, an "oblique viewing direction" means a direction obliquely tilting with respect to axial line 43 of distal end portion 27. In this case, the principal ray is approximated to an optical axis of the visual field direction.

Figure 6:
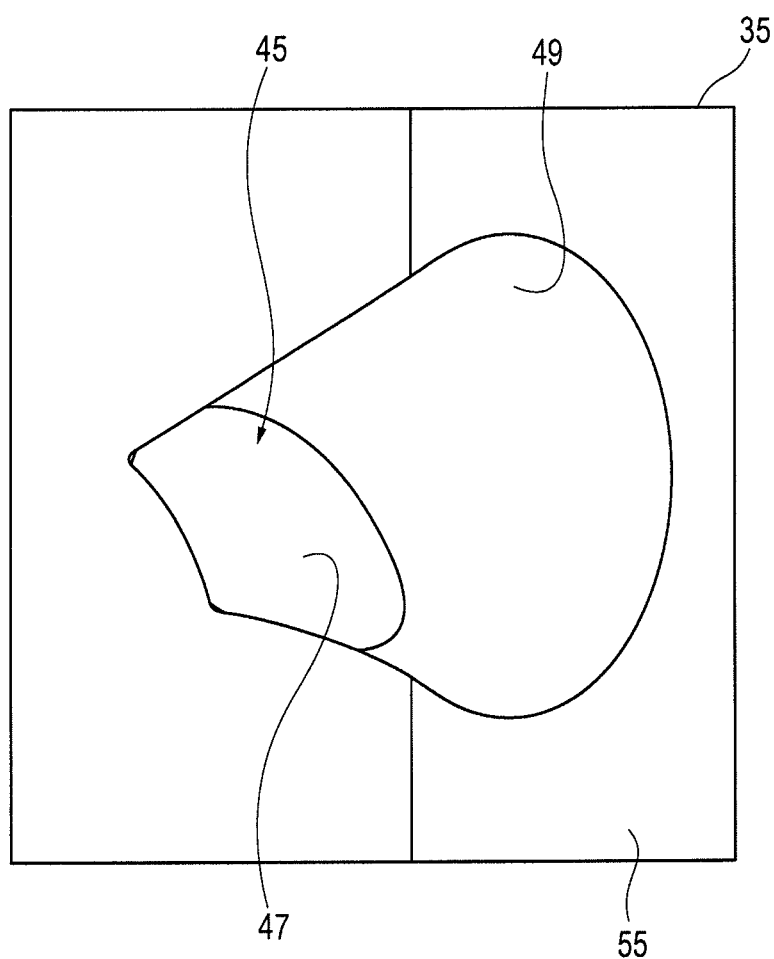
FIG. 6 is a perspective view of a lens which is partially cut off in the oblique viewing endoscope according to Exemplary Embodiment 1.

FIG. 6 is a perspective view of lens 35 partially cut off in oblique viewing endoscope 100 according to Exemplary Embodiment 1.

The light reflected from the object (that is, object light having information on the object: object beam) is incident on lens 35. In oblique viewing endoscope 100, lens 35 is configured to serve as a single lens in which a first surface on the object side is a flat surface and a second surface on the imaging side is a convex surface. Here, an example will be described in which lens 35 is the single lens. However, the example is not limited to the single lens. In lens 35, the central portion on the imaging side has lens surface 45 having a convex curved surface. Oblique viewing endoscope 100 is formed so that lens surface 45 has free curve surface 47 (to be described later). The peripheral edge portion of lens 35 is formed so as to have tapered hole 49 whose inner peripheral surface is an outer peripheral surface of a conical shape which increases in diameter toward imaging element 29.

Lens 35 has a substantially rectangular outer shape or a rectangular outer shape. For example, lens 35 is manufactured by means of nano-imprint or injection molding. In manufacturing lens 35, a lens group in which a plurality of microscopic lenses 35 having the same shape are arranged is formed using a mold such as an original plate of the nano-imprint. After the lens group of the molded object is released, the lens group is cut into individual lenses 35 by means of dicing so that lenses 35 are manufactured one by one. When lens 35 is manufactured, it is necessary to provide a draft to release lens 35 from the mold, and tapered hole 49 of lens 35 is effectively used as the draft.

Figure 7:
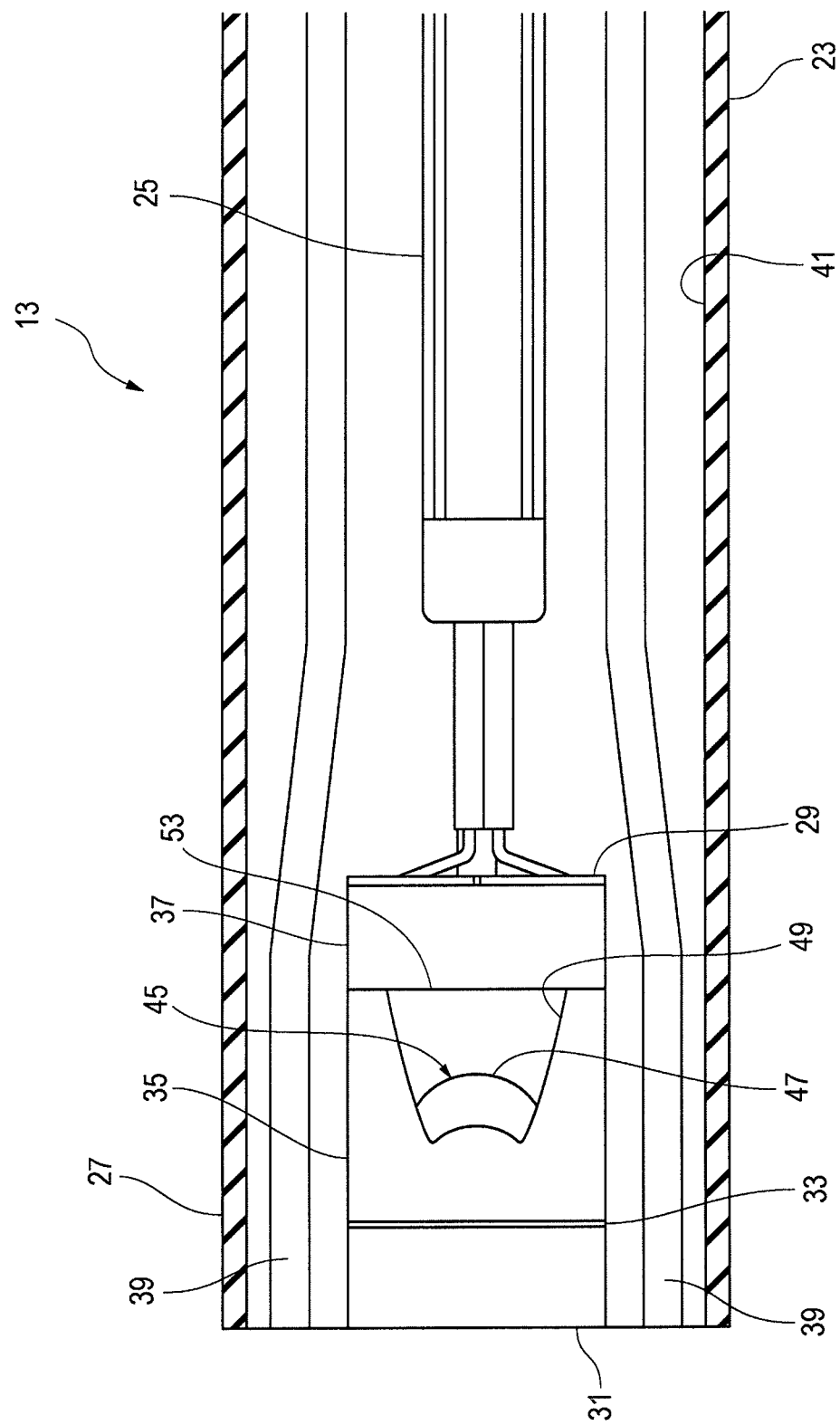
FIG. 7 is a planar sectional view of the oblique viewing endoscope according to Exemplary Embodiment 1.

FIG. 7 is a planar sectional view of oblique viewing endoscope 100 according to Exemplary Embodiment 1.

Objective cover glass 31 is located in the distal end on the objective side. According to the present exemplary embodiment, in oblique viewing endoscope 100, objective cover glass 31 and imaging element 29 are located parallel to each other. Objective cover glass 31, aperture 33, lens 35, element cover glass 37, and imaging element 29 are formed so as to have the same width in a direction orthogonal to axial line 43 of distal end portion 27 in a plan view in FIG. 7. Objective cover glass 31, aperture 33, lens 35, element cover glass 37, and imaging element 29 can be integrally fixed using an adhesion resin, for example. Objective cover glass 31, aperture 33, lens 35, element cover glass 37, and imaging element 29 are covered with a mold resin together with optical fiber 39 as described above.

Element cover glass 37 covers light receiving plane 51 of imaging element 29. In the description herein, light receiving plane 51 is a focal plane including a focal point. For example, element cover glass 37 is formed so that the thickness in a direction along axial line 43 is a predetermined thickness (for example, approximately 0.4 mm). Element cover glass 37 is formed to have the predetermined thickness, and is integrated with imaging element 29. In this manner, a handling property of imaging element 29 formed to have a thin thickness (for example, 0.1 mm) can be improved.

As described above, objective cover glass 31, aperture 33, lens 35, element cover glass 37, and imaging element 29 may be respectively fixed at a proper interval by using an optical column or a holder. In this case, for example, element cover glass 37 can be omitted between lens 35 and imaging element 29, and air layer 53 can be formed therebetween.

In lens 35, lens surface 45 is in contact with the air. In lens 35, an end surface on the opening side of tapered hole 49 is formed as an edge portion 55 having a planar adhesive surface. Edge portion 55 serves as a portion to which the adhesion resin is attached and which is fixed to the front surface of element cover glass 37. In lens 35, element cover glass 37 adheres to edge portion 55. In this manner, an adhesion area between lens 35 and element cover glass 37 can be secured in edge portion 55, and air layer 53 sealed in tapered hole 49 is formed between lens surface 45 and element cover glass 37.

In imaging element 29, the light emitted through lens 35 and air layer 53 is transmitted through the element cover glass 37, and forms an image on light receiving plane 51.

Figure 8:
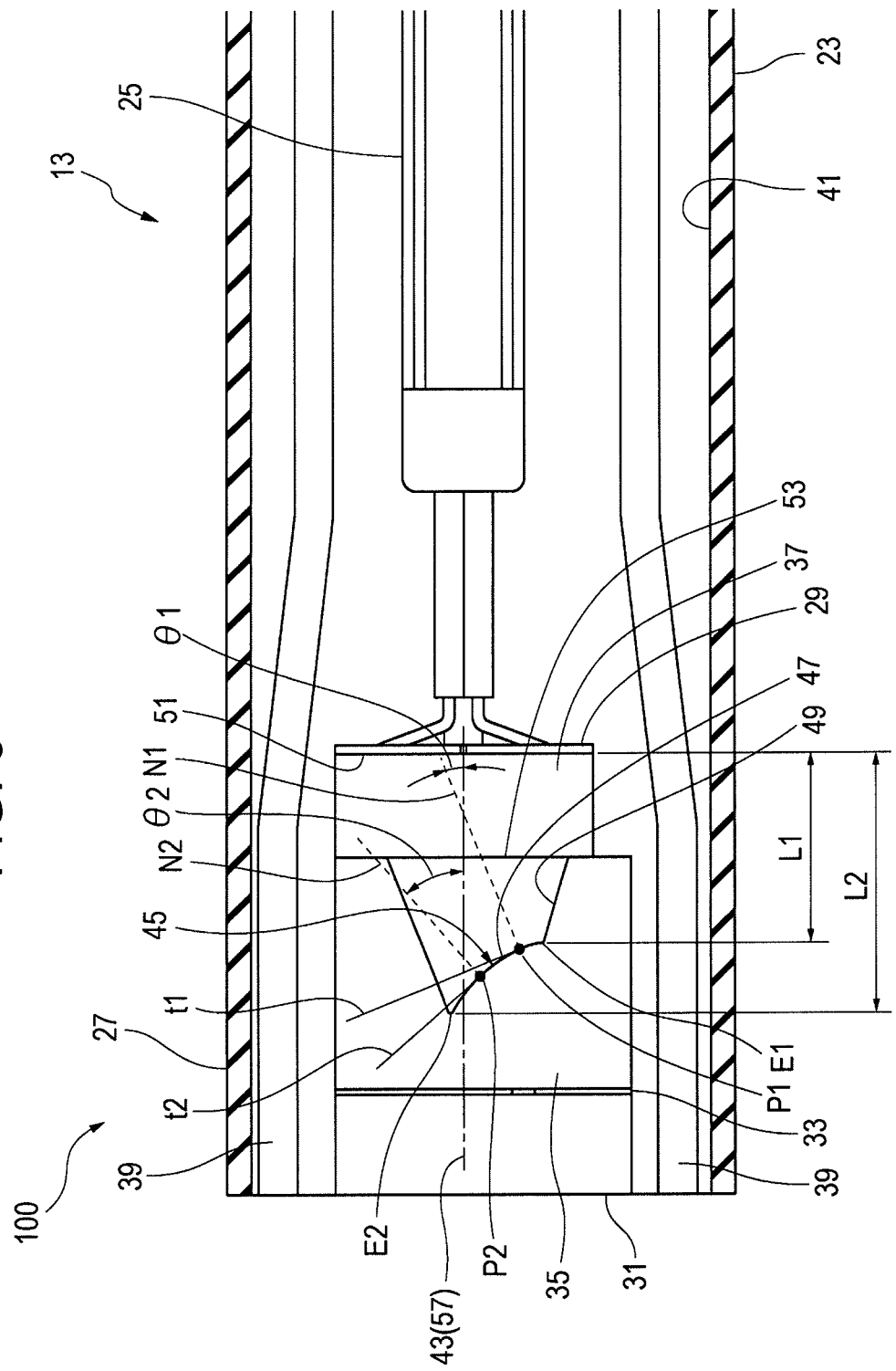
FIG. 8 is a lateral sectional view of the oblique viewing endoscope according to Exemplary Embodiment 1.

FIG. 8 is a lateral sectional view of oblique viewing endoscope 100 according to Exemplary Embodiment 1.

Lens surface 45 described above is formed in lens 35. In lens surface 45, the light incident in the visual field direction which tilts with respect to light receiving center 57 perpendicular to light receiving plane 51 can form the image so as to be perpendicular to light receiving plane 51. Light receiving center 57 may not coincide with axial line 43 of distal end portion 27. In FIG. 8, imaging element 29 is shifted in the upward direction in the drawing with respect to axial line 43 of distal end portion 27. Accordingly, light receiving center 57 perpendicular to light receiving plane 51 is located parallel to axial line 43 on the upper side of axial line 43.

In lens 35 disposed between aperture 33 and imaging element 29, lens surface 45 allows the ray transmitted through aperture 33 in the visual field center to be substantially perpendicularly incident on the center of imaging element 29, thereby forming the image.

Here, ideally, it is desirable that an incident angle of the principal ray passing through the center of the aperture at the center of the imaging element is 0° (vertical incidence). However, since there is no significant influence if the incident angle is approximately ±10°, it is preferable to set the angle to be in a range of 0 to 10°. If the incident angle falls within ±5°, the influence further decreases. Therefore, it is more preferable to set the range from 0° to 5°.

In lens 35, lens surface 45 is allowed to have positive power. In this manner, the rays are bent so that the incident angle of the rays incident on imaging element 29 is reduced. The rays are focused on light receiving plane 51 of imaging element 29, thereby forming the image.

In oblique viewing endoscope 100, lens surface 45 is formed as free curve surface 47.

FIG. 8 illustrates a cross-sectional shape of free curve surface 47 using a plane including, for example, optical axis 59 (refer to FIG. 10) tilting in the visual field direction and light receiving center 57 perpendicular to light receiving plane 51. Free curve surface 47 is a different free curve surface in a lateral section in a different rightward-leftward direction. Hereinafter, in order to simplify the description, as free curve surface 47 in the lateral cross-section, free curve surface 47 illustrated in FIG. 8 which uses the plane including the optical axis tilting in the visual field direction and light receiving center 57 perpendicular to light receiving plane 51 will be described as a representative example.

Here, in lens surface 45, point P1 on the lower side and point P2 on the upper side of free curve surface 47 are considered. An angle formed between normal line N1 perpendicular to tangent line t1 of point P1 and light receiving center 57 is set to θ1. An angle formed between normal line N2 perpendicular to tangent line t2 of point P2 and light receiving center 57 is set to θ2. Angles θ1 and θ2 satisfy a relationship of θ1<θ2.

In free curve surface 47, in the cross section using the plane including the optical axis tilting in the visual field direction and light receiving center 57 perpendicular to light receiving plane 51, curved surface end E1 on a side (lower side) in the visual field direction side is located at a position closer to light receiving plane 51 than curved surface end E2 on the opposite side (upper side) in the visual field direction. That is, in free curve surface 47, distance L2 between curved surface end E2 and light receiving plane 51 is longer than distance L1 between curved surface end E1 and light receiving plane 51.

When ray tracing is actually performed, an area is equally divided using a light incident pupil plane of the optical system, and multiple rays emitted from one object point are set so as to pass through the center of each small division. In this manner, an evaluation can be carried out.

Lens surface 45 can also be free curve surface 47 different from free curve surface 47 described above in the planar section illustrated in FIG. 7. Free curve surface 47 in the planar section becomes free curve surface 47 different in the planar section at a different height. Free curve surface 47 in the planar section illustrated in FIG. 7 is formed in a symmetrical shape by using axial line 43 as a boundary. However, the shape is not limited thereto. That is, free curve surface 47 in the planar section may be formed in an asymmetrical shape by using axial line 43 as the boundary at any desired position in the planar cross-section.

Four conductor connections (not illustrated) are disposed behind imaging element 29. The conductor connections can be formed using a land grid array (LGA), for example. The four conductor connections are formed using a pair of power connections and a pair of signal connections. Transmission cable 25 is configured to have a pair of power lines and a pair of signal lines. The pair of power lines of transmission cable 25 is connected to the pair of power connections of the conductor connections. The pair of signal lines of transmission cable 25 is connected to the pair of signal connections of the conductor connections.

Next, a more specific configuration example when oblique viewing endoscope 100 according to the present exemplary embodiment is realized will be described.

In oblique viewing endoscope 100, an angle (dip angle) of the principal ray in the visual field direction with respect to axial line 43 of distal end portion 27 can be set to 30°, for example. In oblique viewing endoscope 100, for example, the dip angle can be configured to fall within the range of 10° to 60° by utilizing the operation of different lens 35 having the free curve surface suitable for each oblique viewing endoscope 100.

A viewing angle can be set to vertical 30±30°, horizontal±35°, and diagonal 90°.

An F-number can correspond to F9.2.

Objective cover glass 31 can be set to 1 mm wide and 1.15 mm long.

Objective cover glass 31 can have the thickness of 0.4 mm.

Lens 35 can be set to 1 mm wide and 1.15 mm long.

Lens 35 can have the thickness of 0.8 mm.

Imaging element 29 can have an outer diameter size of φ1.0 mm.

Imaging element 29 can have the thickness of 0.1 mm.

Element cover glass 37 can have the outer diameter size of φ1.0 mm.

Element cover glass 37 can have the thickness of 0.4 mm.

Sheath 41 can have the outer diameter of φ1.65 mm and the thickness of 0.1 mm.

Next, an operation of the above-described configuration will be described.

Figure 9:
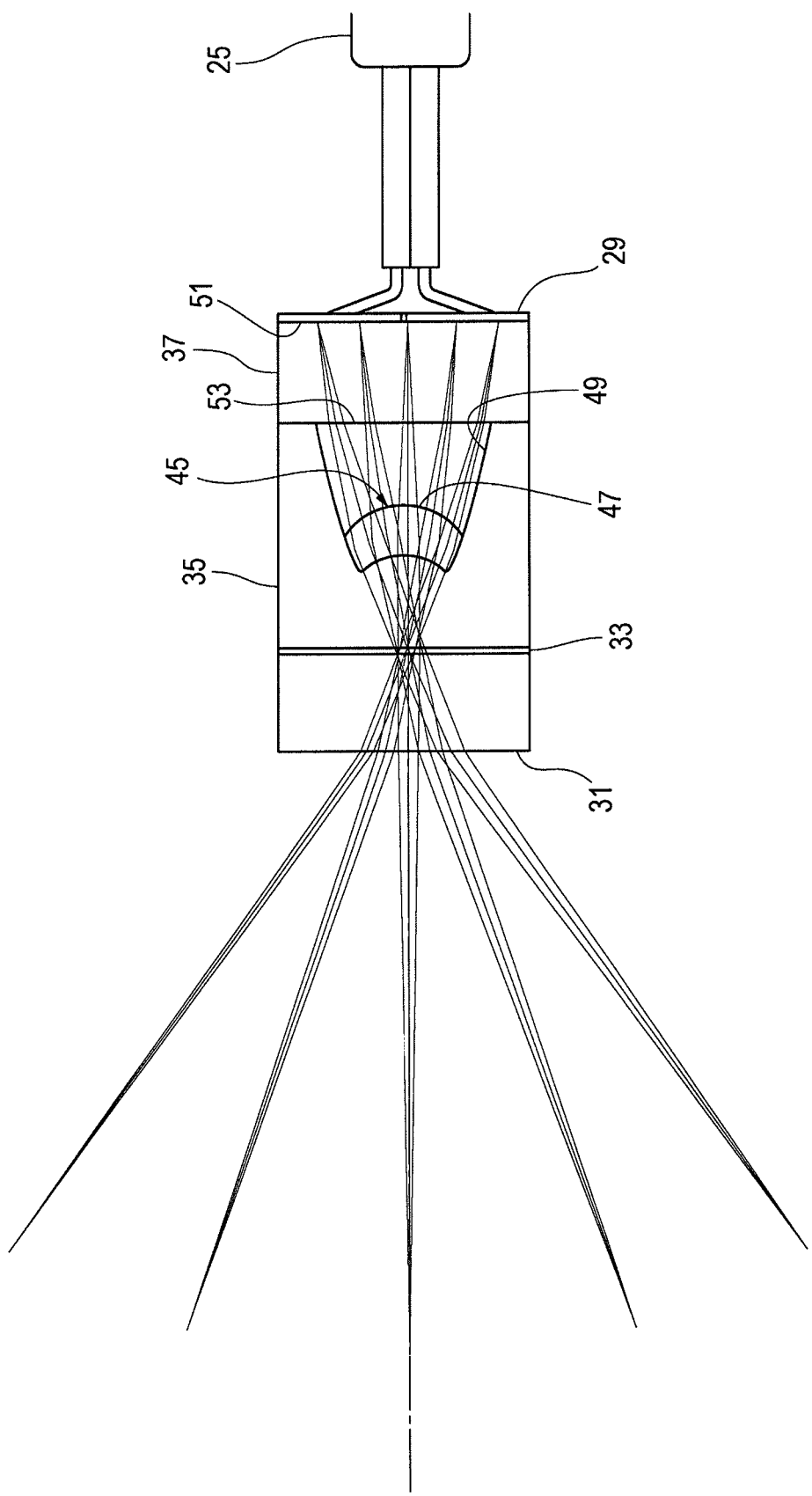
FIG. 9 is a ray tracing diagram in an optical system planar section of the oblique viewing endoscope according to Exemplary Embodiment 1.

FIG. 9 is a ray tracing diagram in an optical system planar section of oblique viewing endoscope 100 according to Exemplary Embodiment 1.

Figure 10:
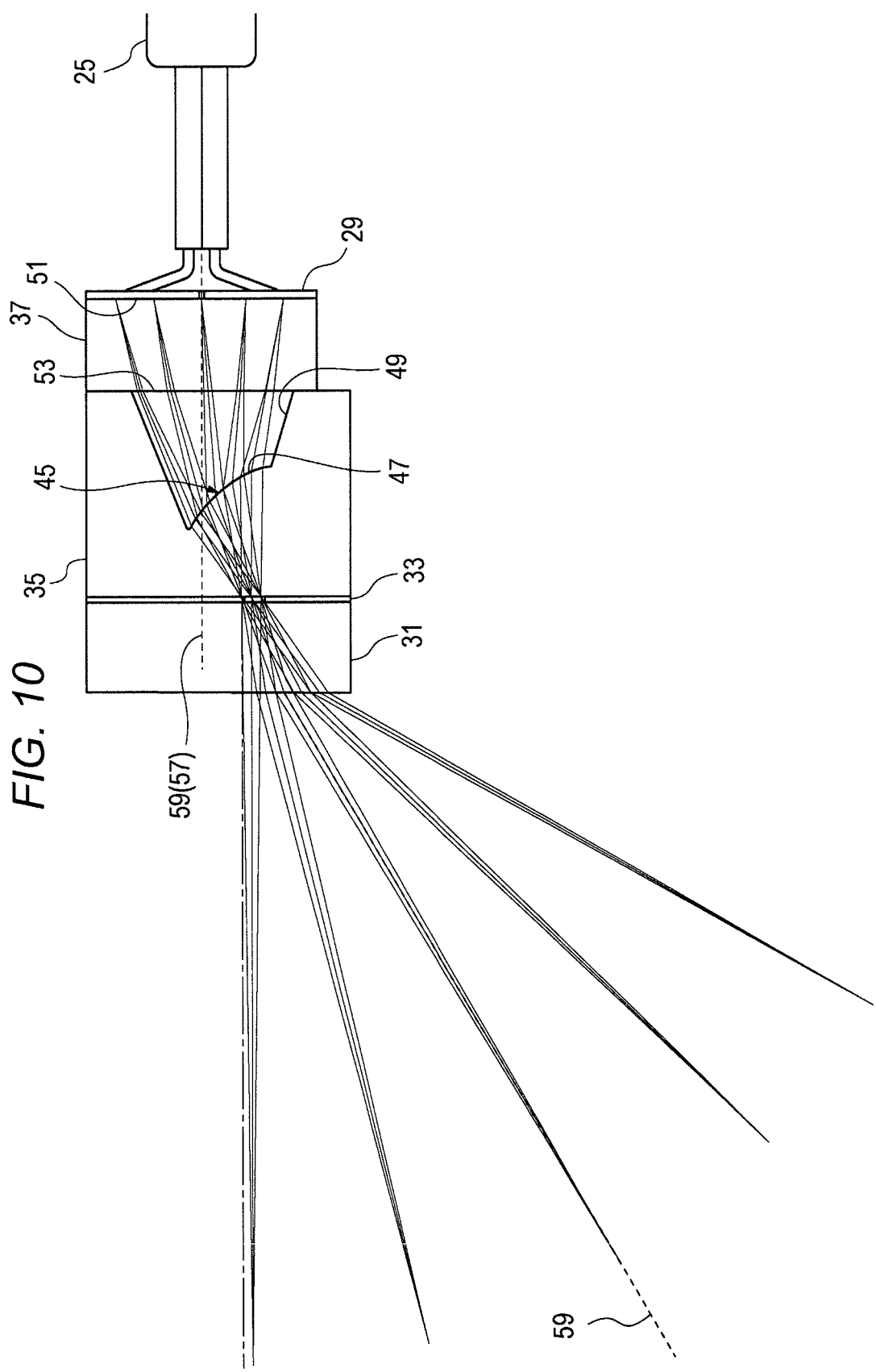
FIG. 10 is a ray tracing diagram in an optical system lateral section of the oblique viewing endoscope according to Exemplary Embodiment 1.

FIG. 10 is a ray tracing diagram in an optical system lateral section of oblique viewing endoscope 100 according to Exemplary Embodiment 1.

Figure 33:
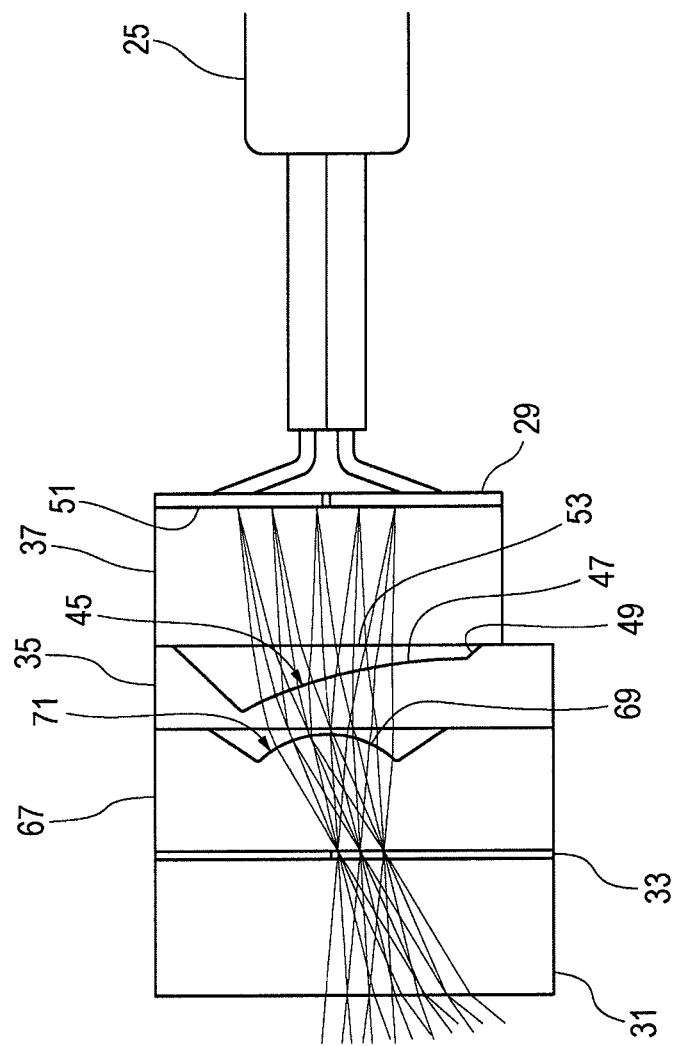
FIG. 33 is a ray tracing diagram in an optical system lateral section of the oblique viewing endoscope according to Exemplary Embodiment 3.

Basically, as lens 35 having this aberration correction function, only one sheet may be sufficiently used. Therefore, compared to a configuration in the related art which includes a front lens group, a prism, and a rear lens group as illustrated in FIG. 33, distal end portion 27 of oblique viewing endoscope 100 can be easily miniaturized (in particular, the diameter can be reduced). In oblique viewing endoscope 100, the number of components can be significantly reduced compared to the configuration in the related art. Accordingly, a distance from the distal end to imaging element 29 can be shortened. Furthermore, in oblique viewing endoscope 100, the number of components can be significantly reduced compared to the configuration in the related art. Accordingly, weight saving can also be achieved. Lens 35 can be manufactured by performing injection molding on a synthetic resin such as plastic (representative material: PMMA). Therefore, if a mold is manufactured, mass production is available, and lens 35 can be manufactured at low cost.

Figure 11:
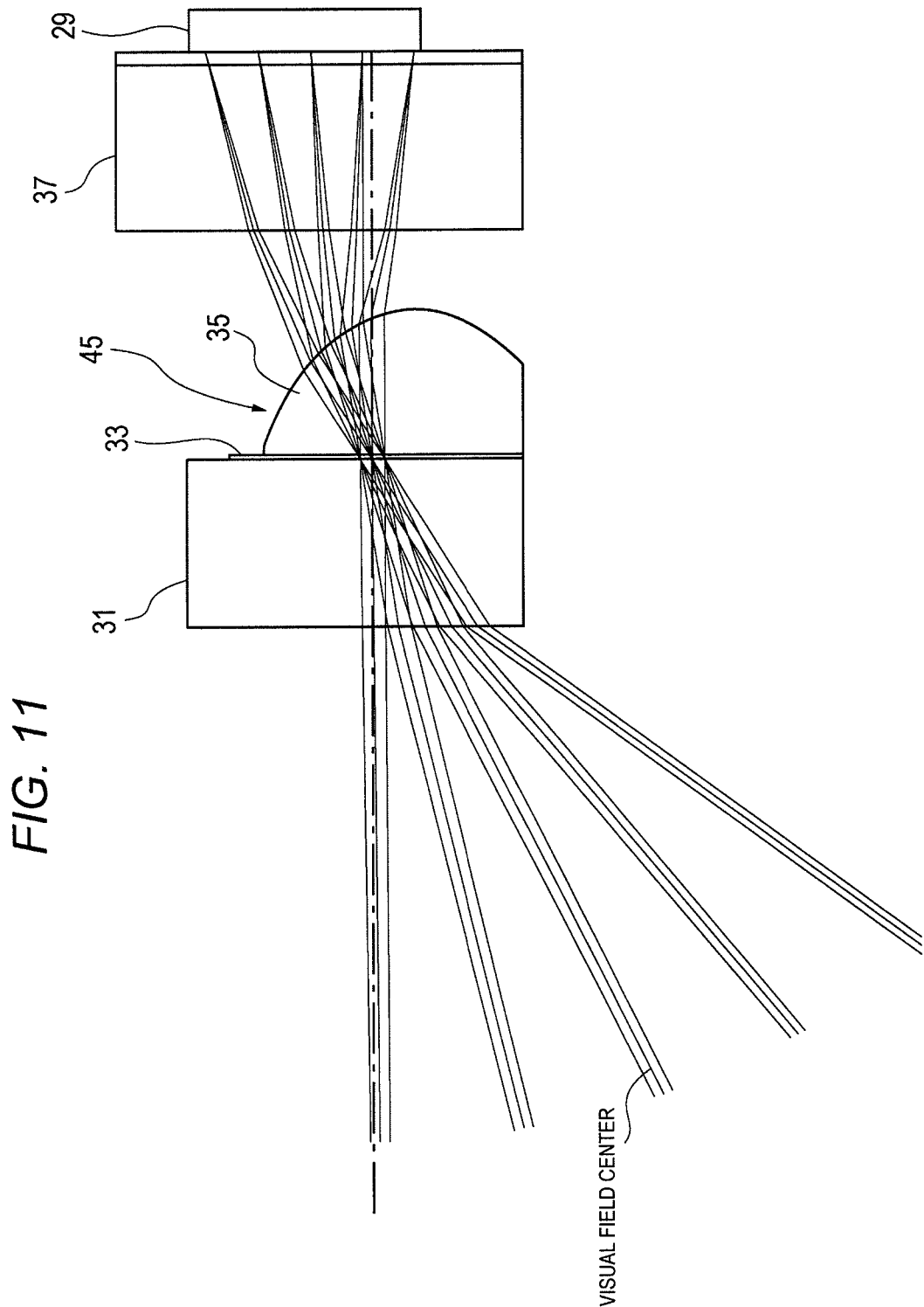
FIG. 11 is a plan view of an optical system in which an imaging element of the oblique viewing endoscope according to Exemplary Embodiment 1 is shifted.

FIG. 11 is a plan view of an optical system in which imaging element 29 of oblique viewing endoscope 100 according to Exemplary Embodiment 1 is shifted.

In oblique viewing endoscope 100, lens surface 45 is allowed to have positive power. In this manner, the rays are bent by lens 35 so that the incident angle of the rays incident on imaging element 29 is reduced. The rays are focused on light receiving plane 51 of imaging element 29, thereby forming the image.

Figure 12:
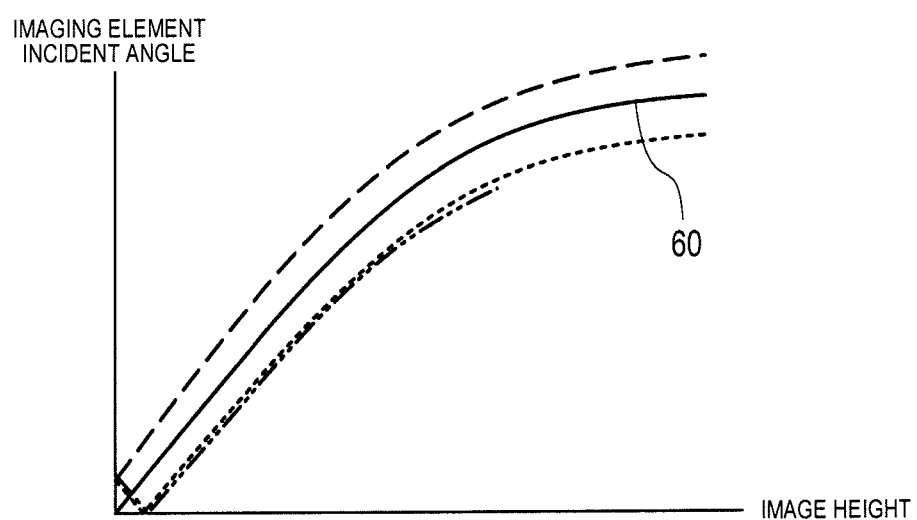
FIG. 12 is a view for describing a correlation between an incident angle and an image height in the shifted imaging element of the oblique viewing endoscope according to Exemplary Embodiment 1.

FIG. 12 is a view for describing a correlation between the incident angle and the image height in shifted imaging element 29 of oblique viewing endoscope 100 according to Exemplary Embodiment 1.

Figure 46:
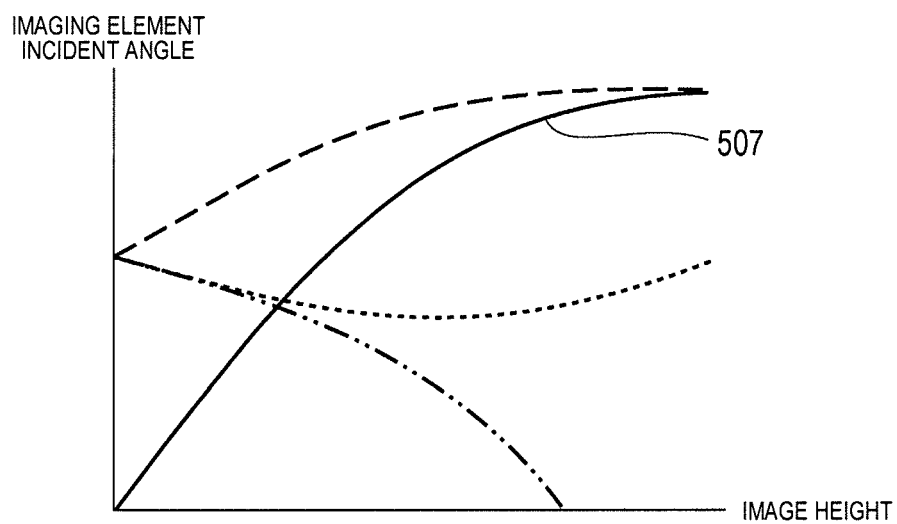
FIG. 46 is a view for describing a correlation between an incident angle and an image height in the shifted imaging element.

In general, in imaging element 29, the incident angle is 0 degrees at the center, and is 20 to 30 degrees at the periphery. Pupil correction is performed symmetrically with respect to the center. In oblique viewing endoscope 100, in the configuration in which imaging element 29 is shifted, lens surface 45 bends the ray so as to reduce the incident angle of the ray incident on imaging element 29. In this manner, compared to a case of adopting the configuration in the related art (correlation between incident angle and the image height illustrated in FIG. 46), the incident light does not greatly deviate from design value characteristic 60. As a result, the light is effectively utilized, and it is possible to prevent a screen from being partially darkened.

In oblique viewing endoscope 100, lens surface 45 which performs aberrations correction on a distorted image has free curve surface 47. At least a portion of lens surface 45 is formed using free curve surface 47. In free curve surface 47, the cross-sectional shape using the plane including the optical axis tilting in the visual field direction and light receiving center 57 perpendicular to light receiving plane 51 has a convex curved surface which protrudes toward light receiving plane 51. Free curve surface 47 is formed using a continuously curved surface controlled so that the radius of curvature of the upper side portion gradually increases compared to the radius of curvature of the lower side portion.

In general, if the ray is bent on the surface having the positive power so as to decrease the incident angle of the ray incident on imaging element 29, it becomes difficult to perform various aberration corrections on field curvature. In oblique viewing endoscope 100, this surface is used as free curve surface 47. Accordingly, it is possible to more freely perform correction on the field curvature and distortion correction. Therefore, image forming performance can be more satisfactorily ensured.

As described above, in free curve surface 47, distance L2 between curved surface end E2 and light receiving plane 51 is longer than distance L1 between curved surface end E1 and light receiving plane 51. Free curve surface 47 employs this shape. Accordingly, only an effective region of free curve surface 47 can be compactly formed by eliminating an unnecessary portion. As a result, distal end portion 27 of oblique viewing endoscope 100 can be more easily miniaturized.

In oblique viewing endoscope 100, the number of components can be significantly reduced compared to the configuration in the related art. Accordingly, a distance from the distal end to imaging element 29 can be shortened. Furthermore, in oblique viewing endoscope 100, the number of components can be significantly reduced compared to the configuration in the related art. Accordingly, weight saving can also be achieved. Lens 35 can be manufactured by performing injection molding on a synthetic resin such as plastic (representative material: PMMA). Therefore, if a mold is manufactured, mass production is available, and lens 35 can be manufactured at low cost.

In oblique viewing endoscope 100, objective cover glass 31 comes into contact with the air. In oblique viewing endoscope 100, objective cover glass 31 can be located parallel to light receiving plane 51 of imaging element 29. Accordingly, an accommodation space of distal end portion 27 for accommodating objective cover glass 31 can be set to a minimum necessary diameter (diameter approximate to a circumscribed circle of imaging element 29).

Therefore, compared to a configuration including the front lens group, the prism, and the rear lens group, oblique viewing endoscope 100 can have a miniaturized configuration and can capture the image in the forward oblique visual field direction while the number of components is minimized.

Furthermore, in oblique viewing endoscope system 11 including oblique viewing endoscope 100, a correction processor (not illustrated) performs image processing such as color correction and gradation correction on image data transmitted from imaging element 29 for each pixel or for each of the above-described small divisions. In a case where the image forming lens is configured to include one convex lens, in a general rotation target lens, magnification chromatic aberration does not occur at the center of the screen. However, in lens 35 in which the principal ray arriving at the center of the screen as in oblique viewing endoscope 100 has an angle of deviation, even in the center of the screen, color drift occurs in a direction in which the ray deviates. Therefore, it is desirable to provide a correction mechanism for electrically correcting the color drift. In oblique viewing endoscope system 11, in addition to the color aberration correction of the optical system which is performed in oblique viewing endoscope 100, chromatic aberration is corrected by performing the image processing. Accordingly, a higher quality image can be displayed on a display device.

Exemplary Embodiment 2

Next, exemplary embodiment 2 will be described. In Exemplary Embodiment 2, the same reference numerals will be given to members the same as the members described in Exemplary Embodiment 1, and repeated description will be omitted.

Figure 13:
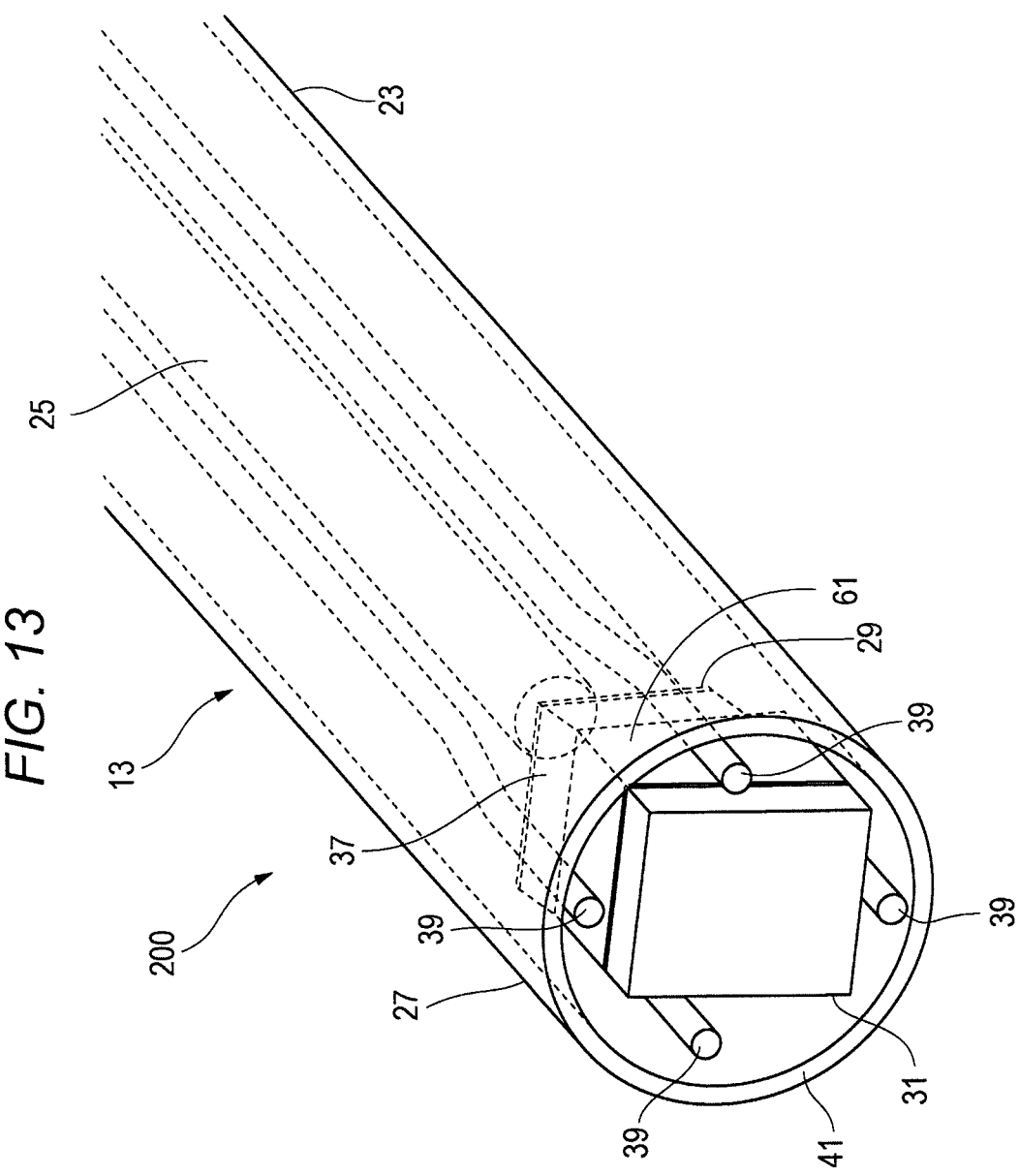
FIG. 13 is a perspective view when a distal end portion of an oblique viewing endoscope according to Exemplary Embodiment 2 is viewed from a front side.

FIG. 13 is a perspective view when distal end portion 27 of oblique viewing endoscope 200 according to Exemplary Embodiment 2 is viewed from the front side.

In oblique viewing endoscope 200 according to Exemplary Embodiment 2, imaging element 29 is located in a tilting manner. In imaging element 29, light receiving center 57 perpendicular to light receiving plane 51 is located tilting in the visual field direction with respect to axial line 43 of columnar distal end portion 27 for accommodating lens 35 and imaging element 29. As imaging element 29, the same one as that according to Exemplary Embodiment 1 can be used in the tilting manner. Therefore, as oblique viewing endoscope 200, it is possible to use a member the same as that of oblique viewing endoscope 100, except that lens 61 is different from that in Exemplary Embodiment 1.

Figure 14:
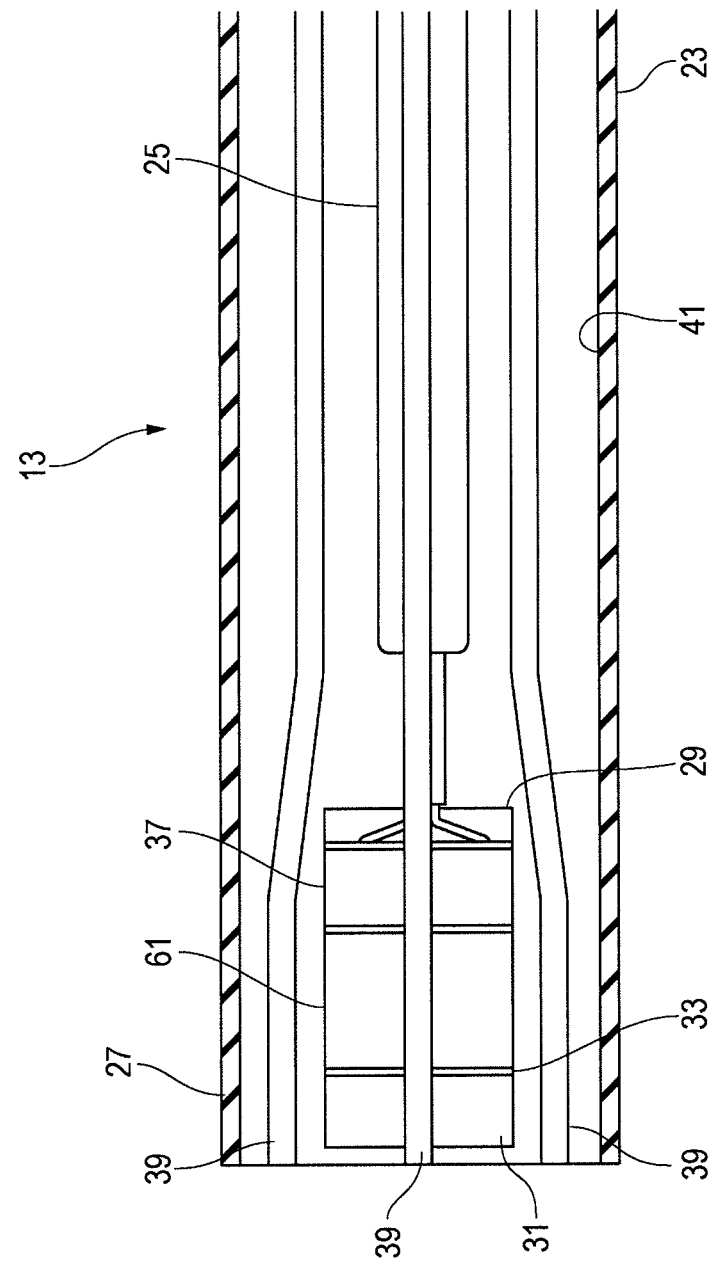
FIG. 14 is a plan view of a sheath interior of the oblique viewing endoscope according to Exemplary Embodiment 2.

FIG. 14 is a plan view of a sheath interior of oblique viewing endoscope 200 according to Exemplary Embodiment 2.

In oblique viewing endoscope 200, a distance in a direction along axial line 43 from lens 61 to the rear end surface of imaging element 29 slightly increases as much as the tilting amount of imaging element 29.

Figure 15:
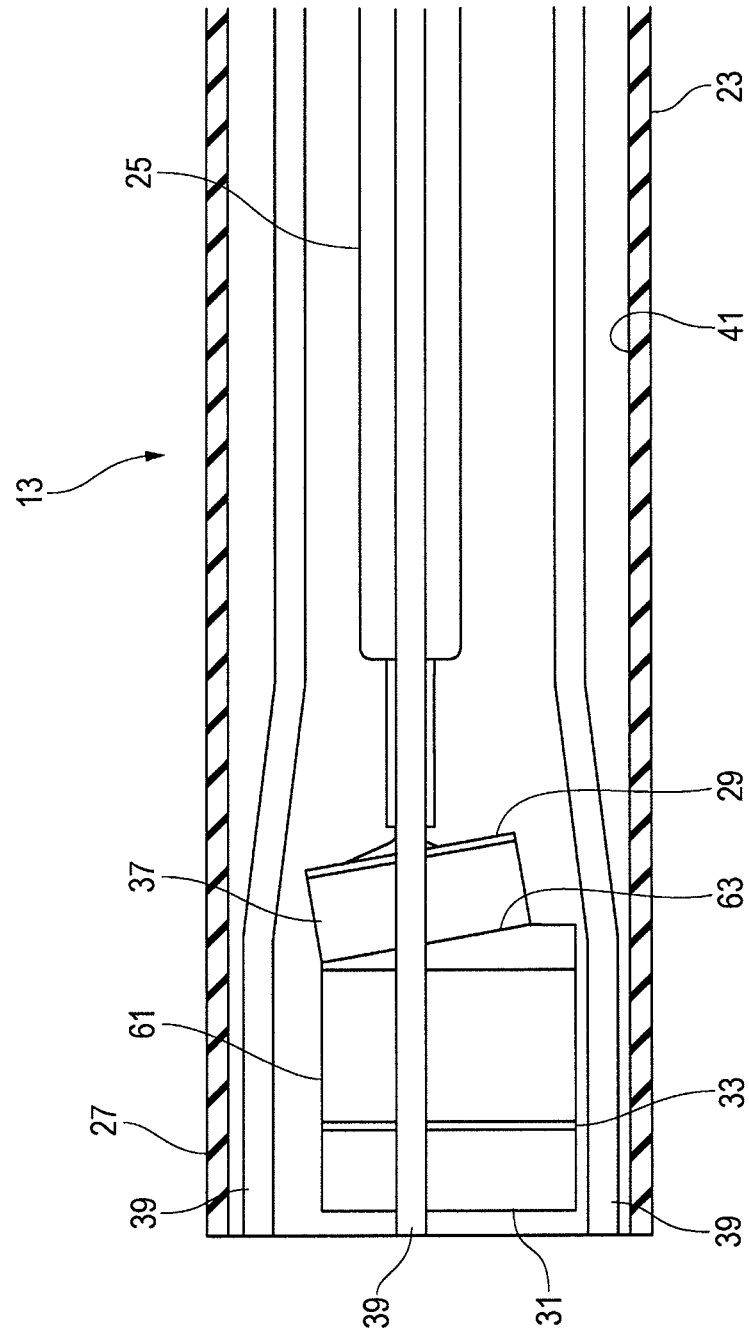
FIG. 15 is a side view of the sheath interior of the oblique viewing endoscope according to Exemplary Embodiment 2.

FIG. 15 is a side view of the sheath interior of oblique viewing endoscope 200 according to Exemplary Embodiment 2.

In oblique viewing endoscope 200, element fixing tilting surface 63 for fixing imaging element 29 in the tilting manner is formed in lens 61. According to the present exemplary embodiment, a tilt angle of imaging element 29 is 10°, for example. This tilt angle is angle θ formed between axial line 43 of distal end portion 27 and light receiving center 57. Imaging element 29 is fixed to element fixing tilting surface 63, thereby causing the rear portion to protrude slightly higher than the upper surface of lens 61.

Figure 16:
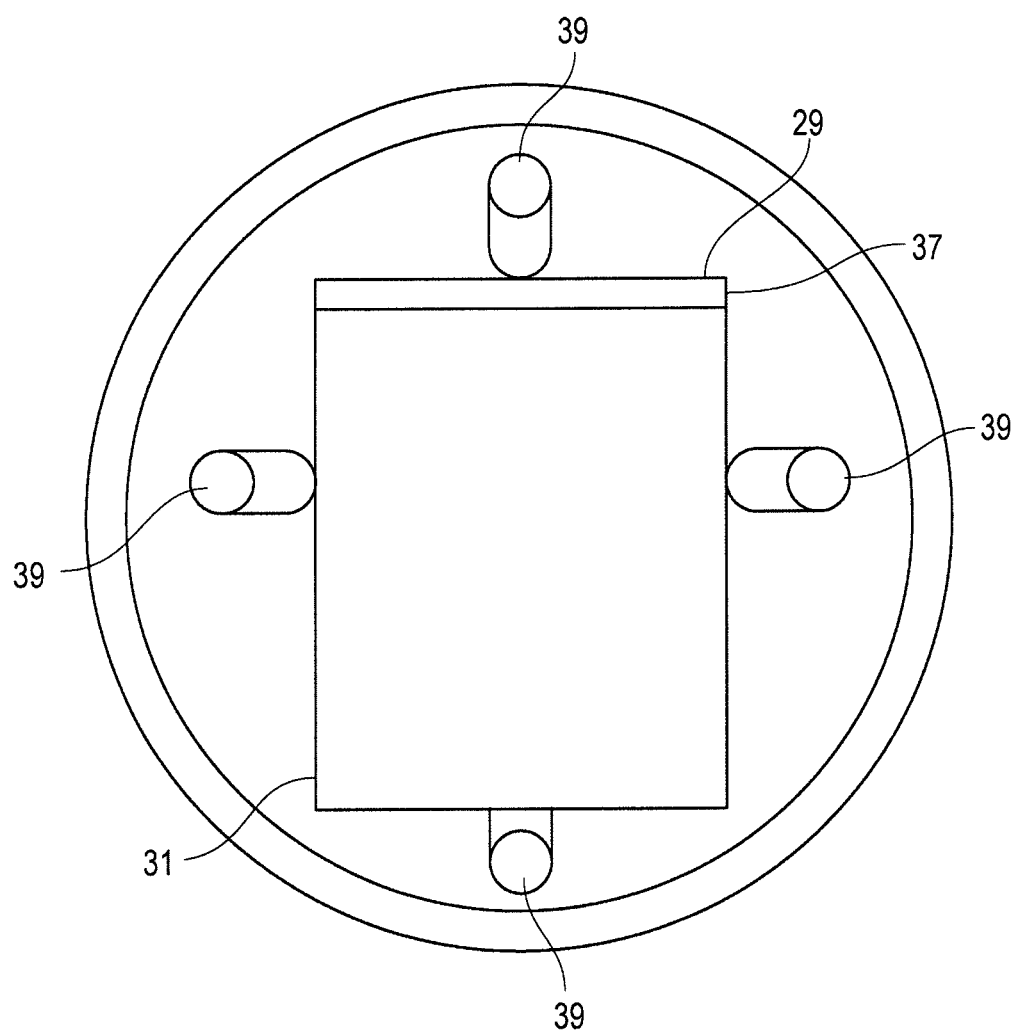
FIG. 16 is a front view of the sheath interior of the oblique viewing endoscope according to Exemplary Embodiment 2.

FIG. 16 is a front view of the sheath interior of oblique viewing endoscope 200 according to Exemplary Embodiment 2.

In oblique viewing endoscope 200, in a front view, the rear portion of imaging element 29 attached in the tilting manner appears to protrude slightly higher than the upper surface of lens 61. In oblique viewing endoscope 200, a total height in a front view increases as much as the protruding amount of the rear portion of imaging element 29, compared to oblique viewing endoscope 100. Therefore, sheath 41 increases in the outer diameter, compared to that according to oblique viewing endoscope 100. Specifically, in a case where the outer diameter of sheath 41 of oblique viewing endoscope 100 is 1.65 mm, for example, the outer diameter of sheath 41 of oblique viewing endoscope 200 is 1.8 mm, for example.

Figure 17:
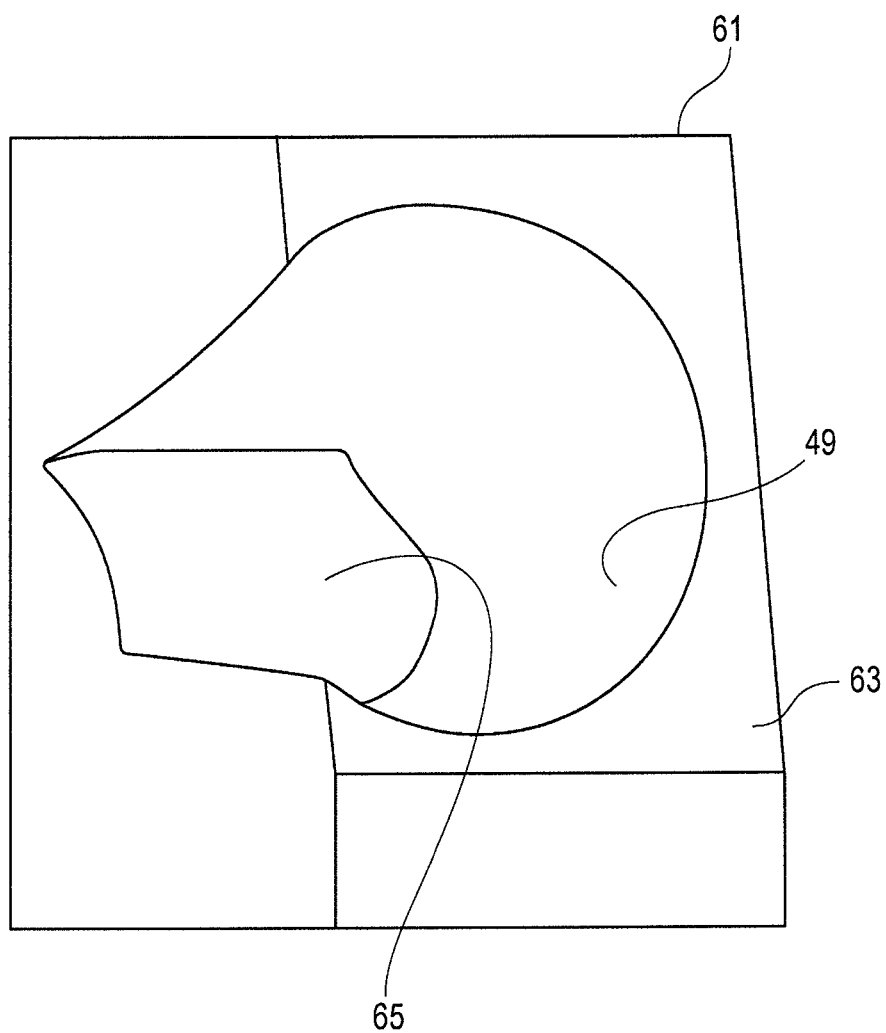
FIG. 17 is a perspective view of a lens which is partially cut off in the oblique viewing endoscope according to Exemplary Embodiment 2.

FIG. 17 is a perspective view of lens 61 which is partially cut off in oblique viewing endoscope 200 according to Exemplary Embodiment 2.

The operation of lens 61 of oblique viewing endoscope 200 is the same as the basic operation of lens 35 of oblique viewing endoscope 100. However, the curvature of lens 61 at various positions of free curve surface 65 is different from that of lens 35 of oblique viewing endoscope 100. A shape difference of free curve surface 65 is caused by a fact that a refraction angle depending on lens 61 is relaxed as large as 10° compared to a case of lens 35.

Figure 18:
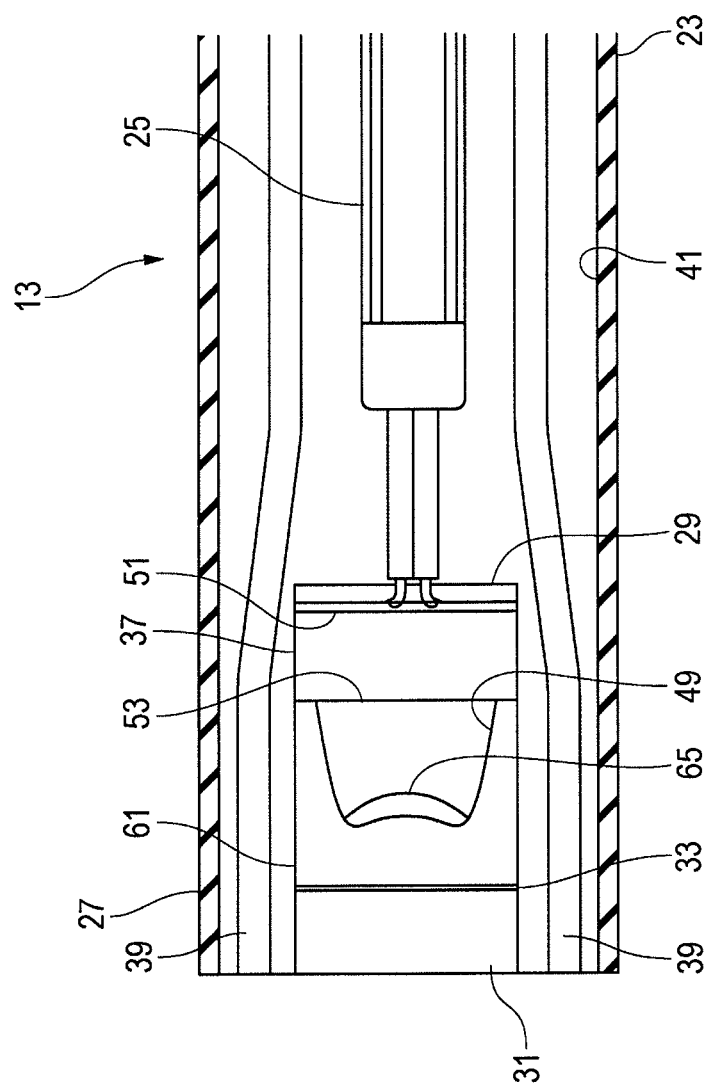
FIG. 18 is a planar sectional view of the oblique viewing endoscope according to Exemplary Embodiment 2.

FIG. 18 is a planar sectional view of oblique viewing endoscope 200 according to Exemplary Embodiment 2.

As described above, in oblique viewing endoscope 200, the refraction angle required for lens 61 is relaxed. Therefore, in free curve surface 65 of lens 61, a protruding distance decreases than that of free curve surface 47 of lens 35 in oblique viewing endoscope 100 in a planar section.

Figure 19:
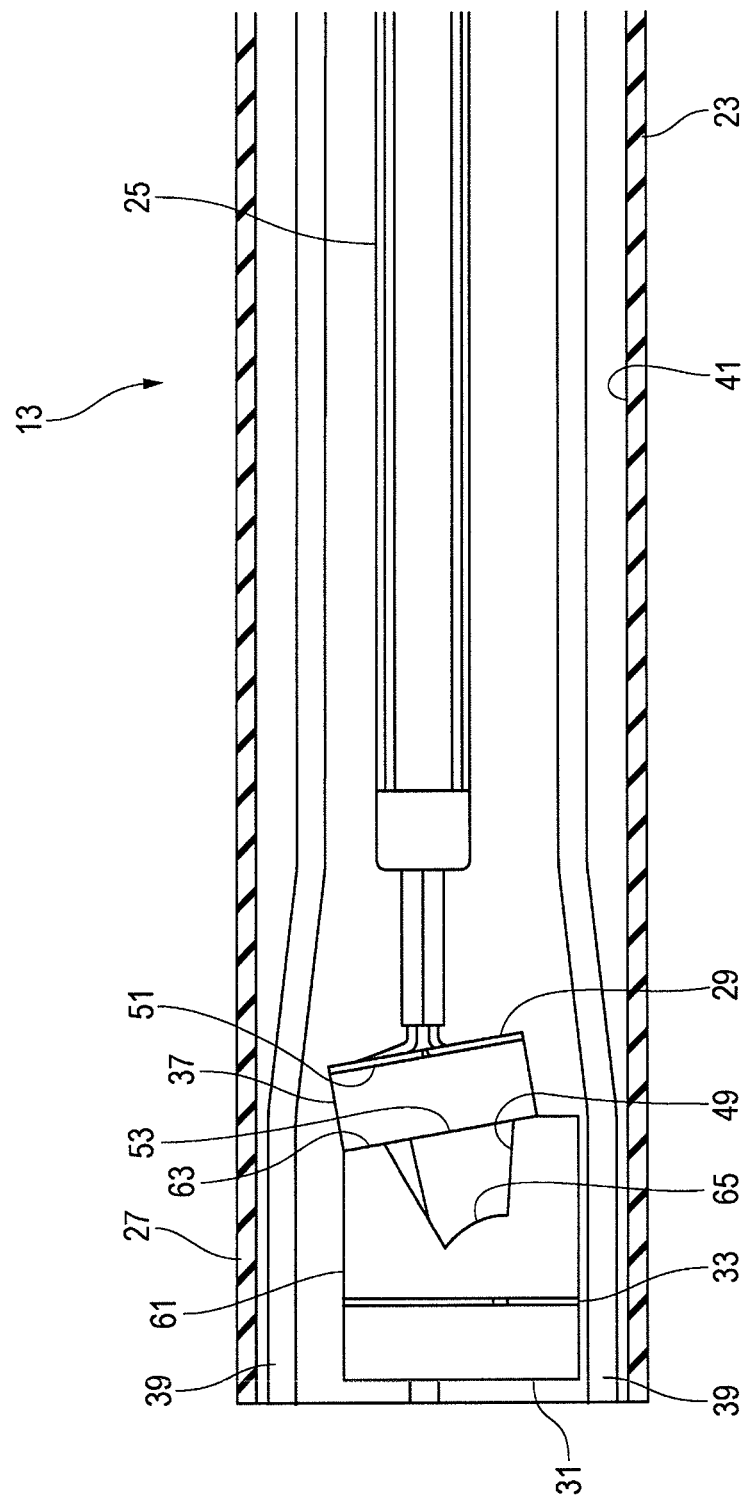
FIG. 19 is a lateral sectional view of the oblique viewing endoscope according to Exemplary Embodiment 2.

FIG. 19 is a lateral sectional view of oblique viewing endoscope 200 according to Exemplary Embodiment 2. In oblique viewing endoscope 200, the protruding distance of free curve surface 65 also decreases than that of free curve surface 47 of lens 35 in oblique viewing endoscope 100 in a lateral section.

Next, a more specific configuration example when oblique viewing endoscope 200 according to the present exemplary embodiment is realized will be described.

In oblique viewing endoscope 200, the angle (dip angle) of the principal ray in the visual field direction with respect to axial line 43 of distal end portion 27 can be set to 30°, for example. In oblique viewing endoscope 200, for example, the dip angle can be configured to fall within the range of 10° to 60° by utilizing the operation of different lens 35 having the free curve surface suitable for each oblique viewing endoscope 200.

A viewing angle can be set to vertical 30±30°, horizontal±35°, and diagonal 90°.

The F-number can correspond to F9.2.

Objective cover glass 31 can be set to 1 mm wide and 1.15 mm long.

Objective cover glass 31 can have the thickness of 0.4 mm.

Lens 35 can be set to 1 mm wide and 1.15 mm long.

Lens 35 can have the thickness of 0.8 mm.

Imaging element 29 can have an outer diameter size of φ1.0 mm.

Imaging element 29 can have the thickness of 0.1 mm.

Element cover glass 37 can have the outer diameter size of φ1.0 mm.

Element cover glass 37 can have the thickness of 0.4 mm.

Sheath 41 can have the outer diameter of φ1.8 mm and the thickness of 0.1 mm.

Since imaging element 29 is tilted and shifted, oblique viewing endoscope 200 becomes larger as much as the image height in the tilt angle direction (approximately 0.35 mm in a case of 1 mm sensor). That is, in a case where imaging element 29 tilting as much as 10° is fixed to lens 61 at the height of 1.0 mm, the height of lens 61 and imaging element 29 which are integrated with each other is 1.35 mm.

Performance of oblique viewing endoscope 200 is greatly improved by tilting imaging element 29. In a case where a large number of pixels is present, a configuration of tilting imaging element 29 is advantageously adopted.

Next, an operation of the above-described configuration will be described.

Figure 20:
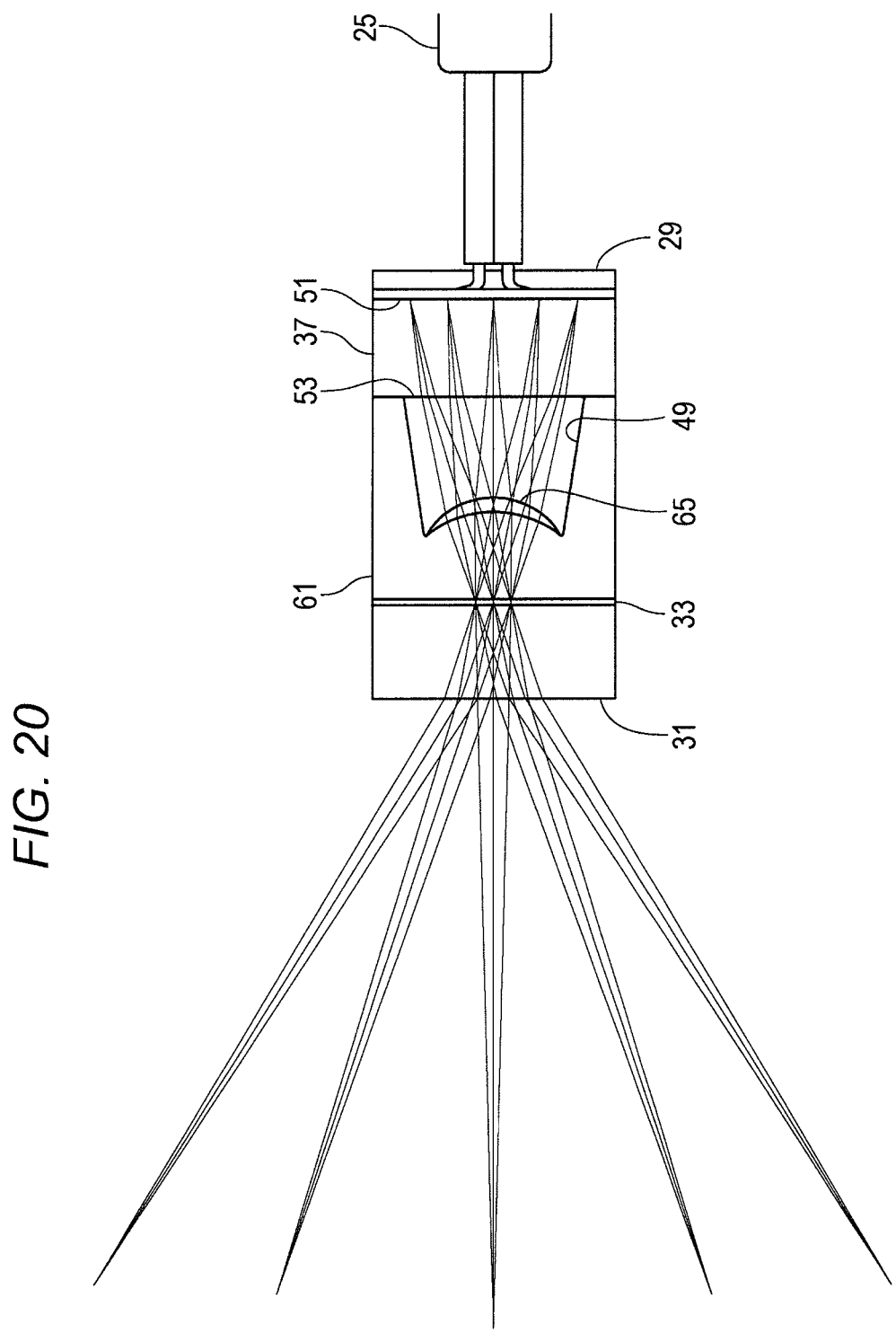
FIG. 20 is a ray tracing diagram in an optical system planar section of the oblique viewing endoscope according to Exemplary Embodiment 2.

FIG. 20 is a ray tracing diagram in an optical system planar section of oblique viewing endoscope 200 according to Exemplary Embodiment 2.

Figure 21:
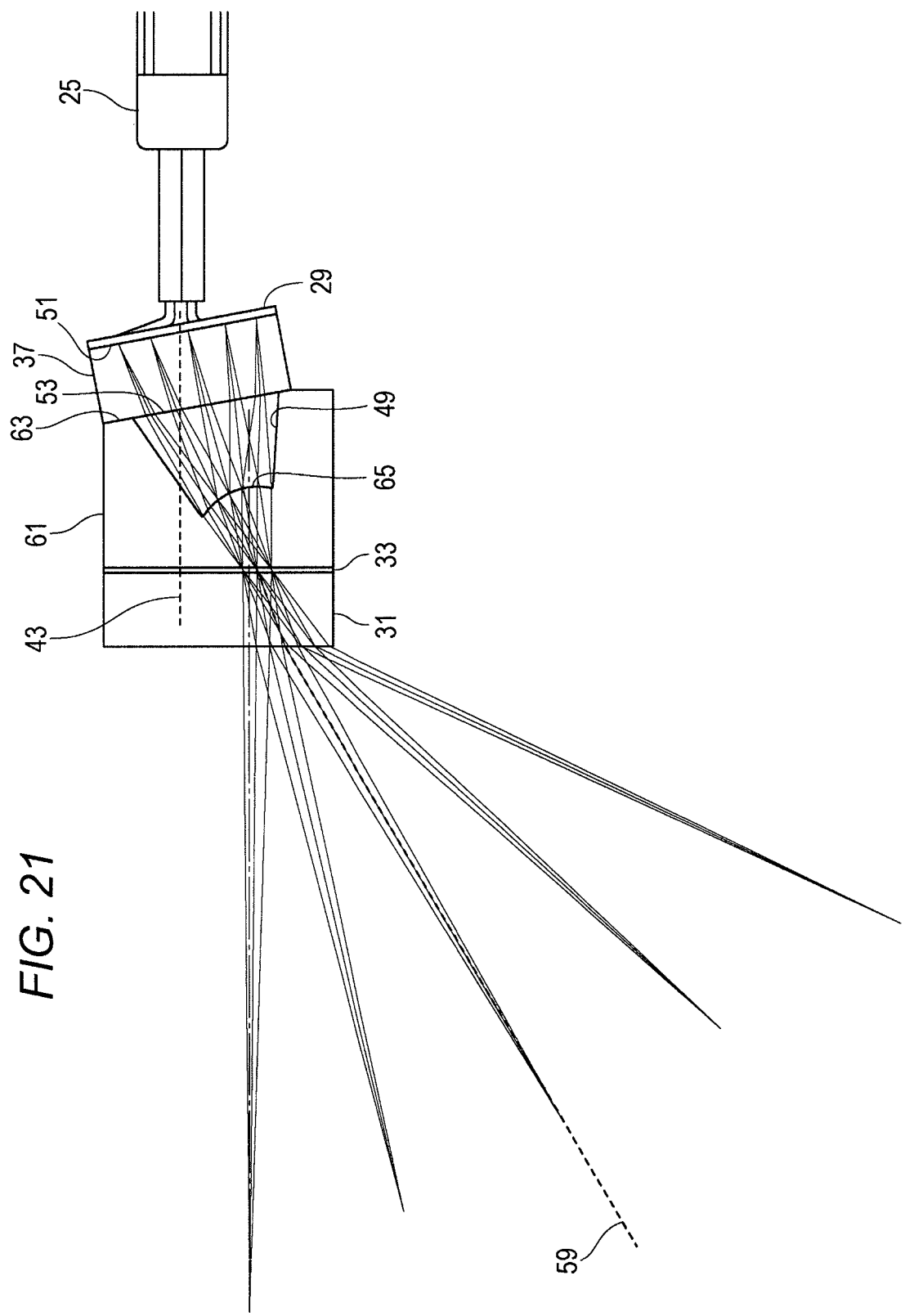
FIG. 21 is a ray tracing diagram in an optical system lateral section of the oblique viewing endoscope according to Exemplary Embodiment 2.

FIG. 21 is a ray tracing diagram in an optical system lateral section of oblique viewing endoscope 200 according to Exemplary Embodiment 2.

In oblique viewing endoscope 200, imaging element 29 tilts in the visual field direction as illustrated in FIG. 21. For example, in a case where an angle formed between the optical axis included in the principal ray in the visual field direction and axial line 43 of distal end portion 27 is 30°, imaging element 29 is assumed to tilt as much as 10° in the visual field direction. In this case, compared to a configuration in which imaging element 29 does not tilt, the refraction angle depending on lens 61 may be set to 20°. In lens 61, the refraction angle in a planar sectional view illustrated in FIG. 20 also becomes smaller than the refraction angle of lens 35 illustrated in FIG. 9 which is configured so that imaging element 29 does not tilt.

Accordingly, in oblique viewing endoscope 200, the refraction angle of lens 61 can be reduced as much as 10°, compared to the configuration in which imaging element 29 does not tilt. Lens 61 can minimize the magnification chromatic aberration by reducing the refraction angle. As a result, in oblique viewing endoscope 200 in which imaging element 29 tilts, the outer diameter of sheath 41 slightly increases. However, compared to a configuration in which the lens does not tilt at the same dip angle, image quality can be improved. In a case of the oblique viewing endoscope having a particularly large number of pixels, the configuration in which imaging element 29 tilts is advantageously adopted, since the magnification chromatic aberration is reduced and the performance is greatly improved.

In this way, in oblique viewing endoscope 200, the field curvature is easily corrected by tilting imaging element 29, and the image forming performance can be improved. However, this leads to an increase in the diameter. Accordingly, it is desirable to improve the performance while the tilting amount of tilting is minimized and the increase in diameter is suppressed. In this case, it is desirable that the tilting amount of imaging element 29 is 15° or smaller, and preferably 10° or smaller, if possible. In a case where priority is given to the further reduced diameter, it is desirable that the tilting amount is 5° or smaller.

Exemplary Embodiment 3

Next, Exemplary Embodiment 3 will be described. In Exemplary Embodiment 3, the same reference numerals will be given to members the same as the members described in Exemplary Embodiment 1, and repeated description will be omitted.

Figure 22:
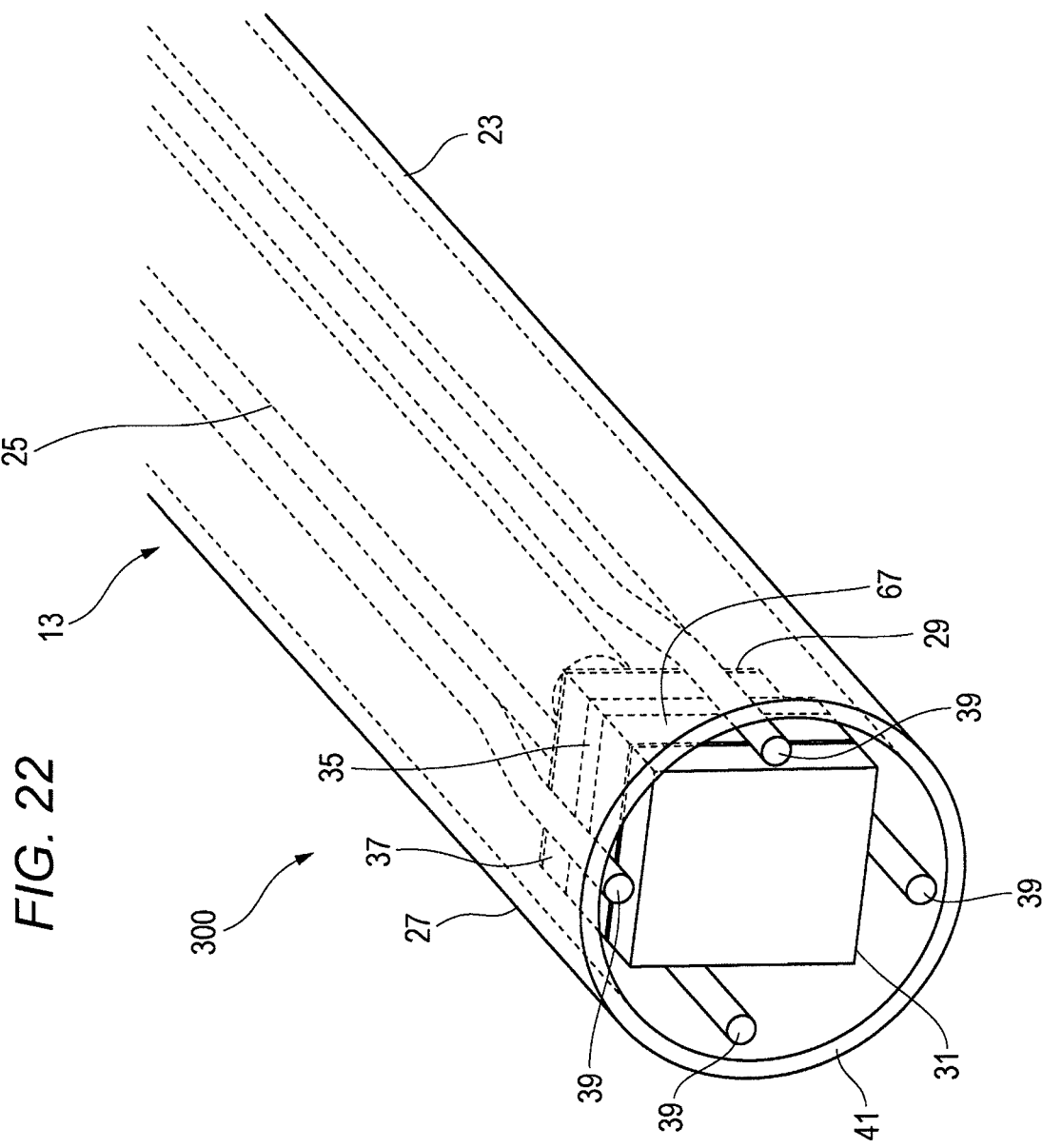
FIG. 22 is a perspective view when a distal end portion of an oblique viewing endoscope according to Exemplary Embodiment 3 is viewed from a front side.

FIG. 22 is a perspective view when distal end portion 27 of oblique viewing endoscope 300 according to Exemplary Embodiment 3 is viewed from the front side.

Figure 23:
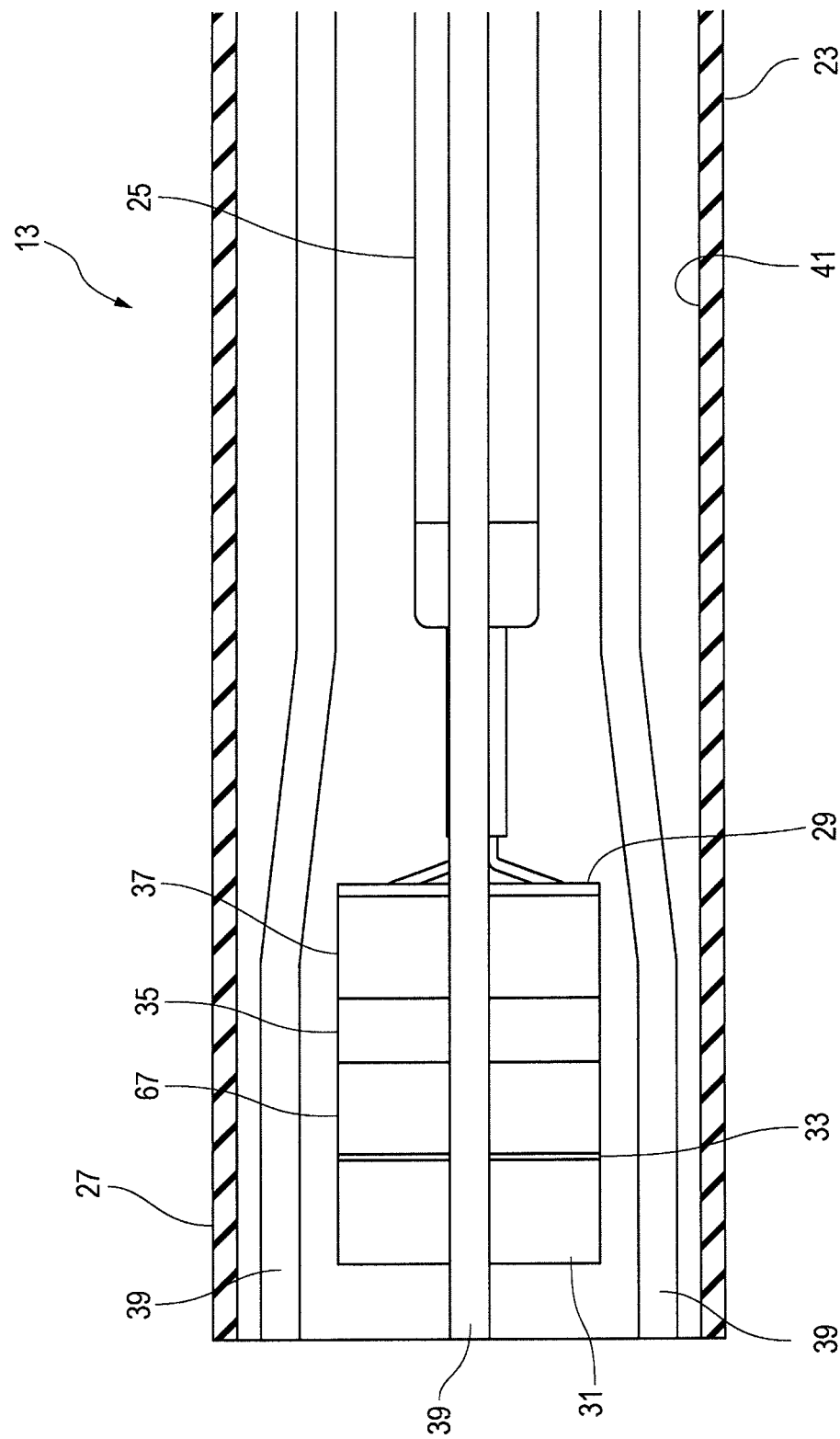
FIG. 23 is a plan view of a sheath interior of the oblique viewing endoscope according to Exemplary Embodiment 3.

FIG. 23 is a plan view of the sheath interior of oblique viewing endoscope 300 according to Exemplary Embodiment 3.

In oblique viewing endoscope 300, front stage lens 67 is disposed between objective cover glass 31 and lens 35. In oblique viewing endoscope 300, a distance from objective cover glass 31 to lens 35 is longer than that of oblique viewing endoscope 100, as front stage lens 67 is disposed between objective cover glass 31 and lens 35.

Figure 24:
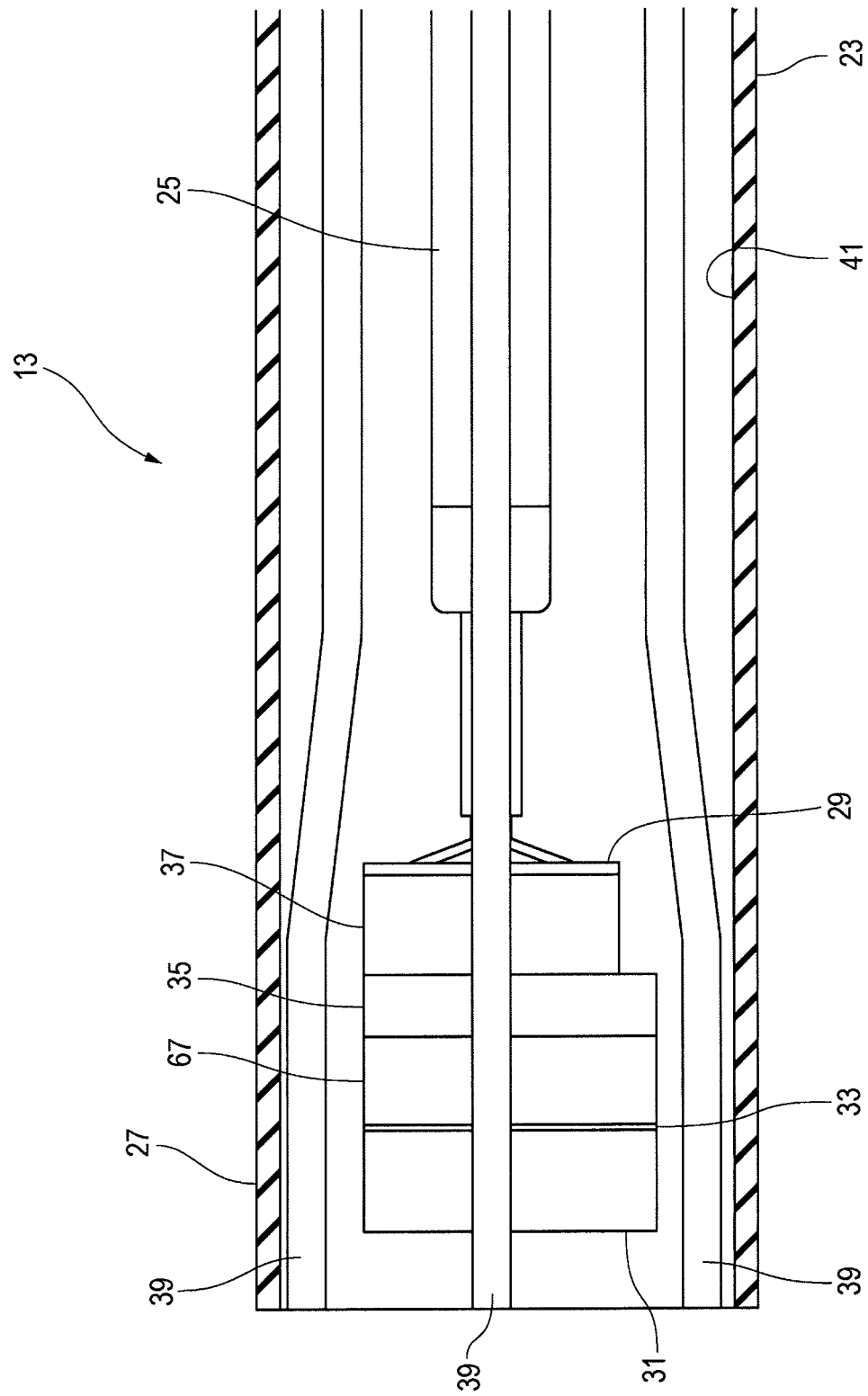
FIG. 24 is a side view of the sheath interior of the oblique viewing endoscope according to Exemplary Embodiment 3.

FIG. 24 is a side view of the sheath interior of oblique viewing endoscope 300 according to Exemplary Embodiment 3.

Figure 25:
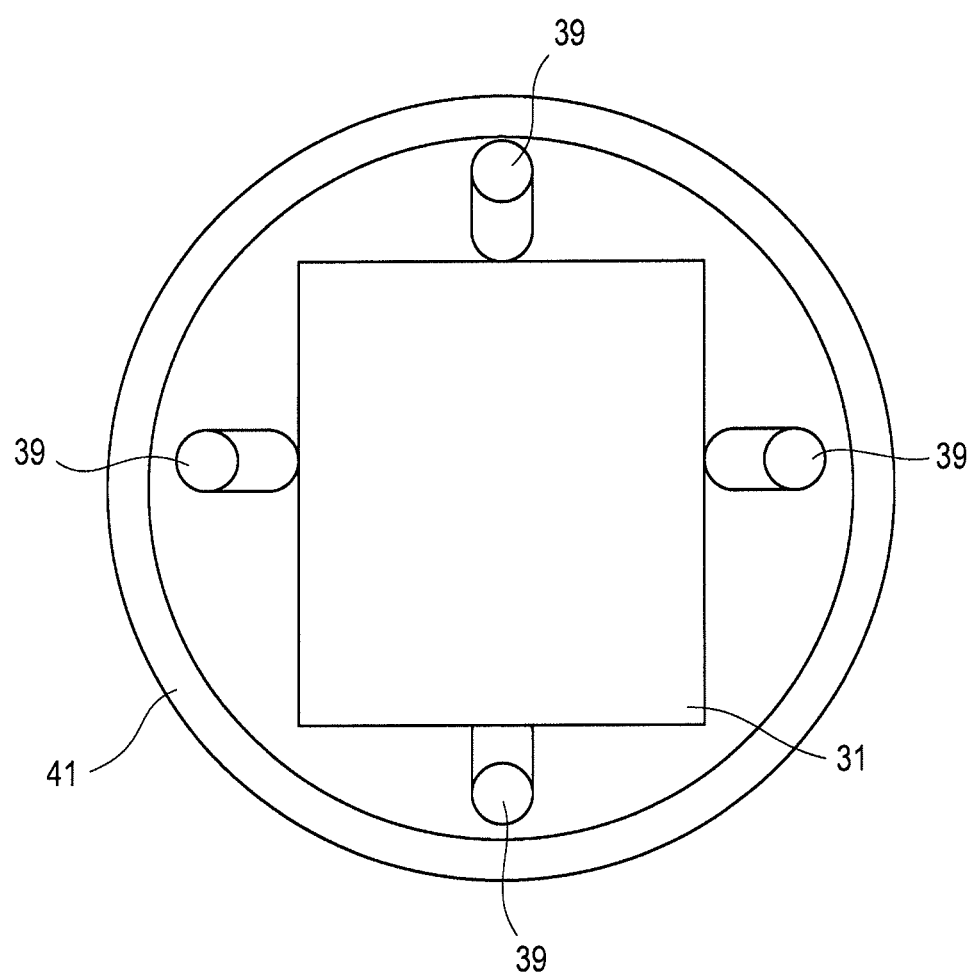
FIG. 25 is a front view of the sheath interior of the oblique viewing endoscope according to Exemplary Embodiment 3.

FIG. 25 is a front view of the sheath interior of oblique viewing endoscope 300 according to Exemplary Embodiment 3.

Front stage lens 67 is formed in a rectangular shape so that the width in the rightward-leftward direction in FIG. 23 and the height in the upward-downward direction in FIG. 24 are the same as those of objective cover glass 31 and lens 35. Oblique viewing endoscope 300 has a front view the same as that of oblique viewing endoscope 100.

Figure 26:
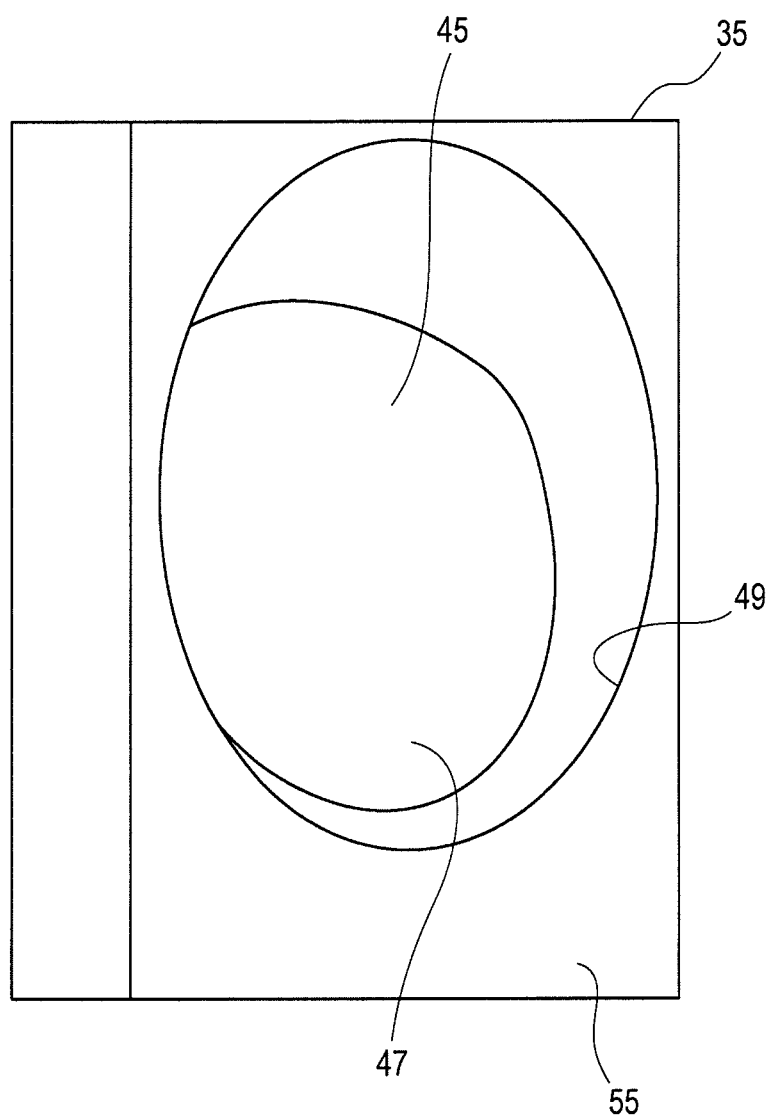
FIG. 26 is a perspective view of a lens in the oblique viewing endoscope according to Exemplary Embodiment 3.

FIG. 26 is a perspective view of lens 35 in oblique viewing endoscope 300 according to Exemplary Embodiment 3.

Figure 27:
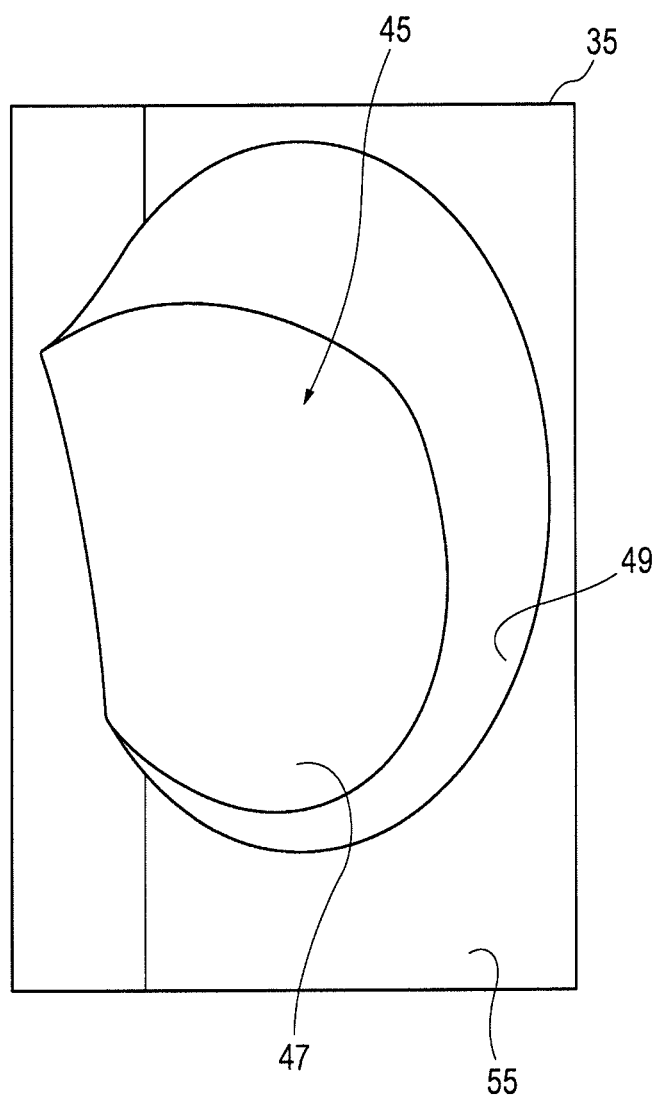
FIG. 27 is a perspective view of the lens which is partially cut off in the oblique viewing endoscope according to Exemplary Embodiment 3.

FIG. 27 is a perspective view of lens 35 which is partially cut off in oblique viewing endoscope 300 according to Exemplary Embodiment 3.

Lens 35 of oblique viewing endoscope 300 is identical to lens 35 of oblique viewing endoscope 100. As described above, in oblique viewing endoscope 300, the refraction angle required for lens 35 is relaxed. Therefore, free curve surface 47 of lens 35 has a protruding distance shorter than that of free curve surface 47 of lens 35 in oblique viewing endoscope 100.

Figure 28:
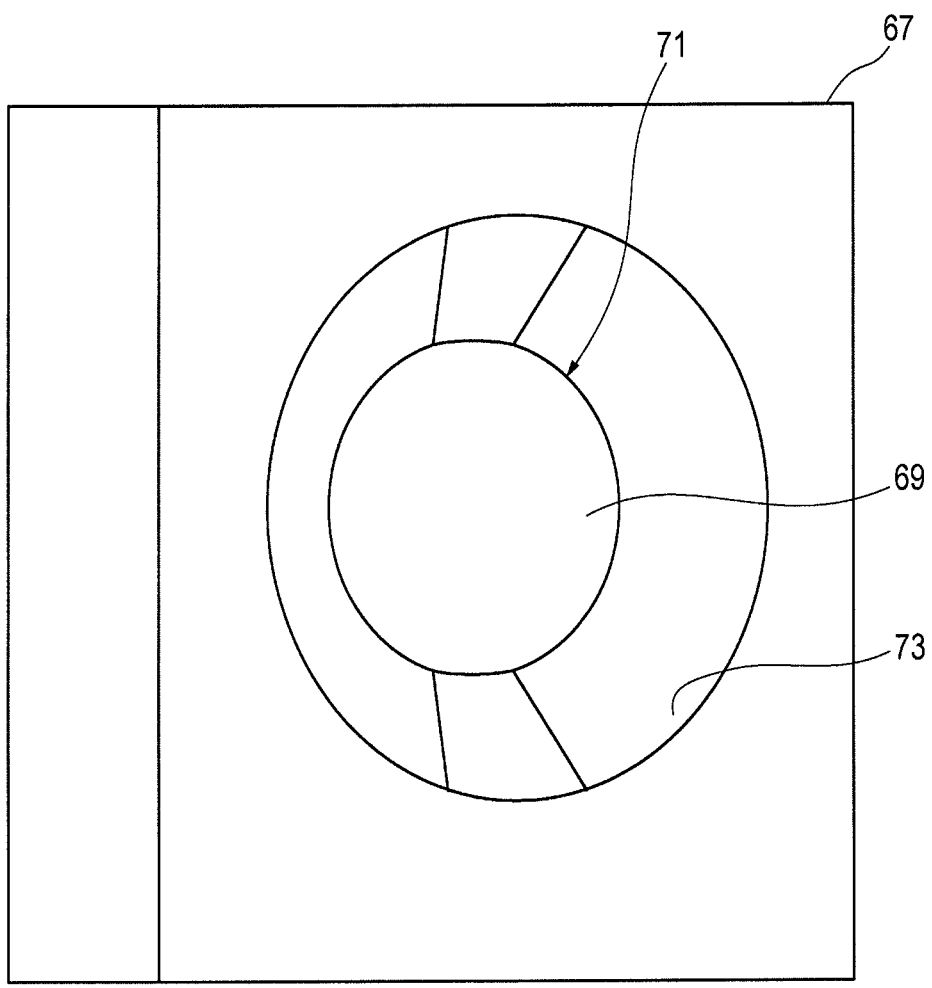
FIG. 28 is a perspective view of a front stage lens in the oblique viewing endoscope according to Exemplary Embodiment 3.

FIG. 28 is a perspective view of front stage lens 67 in oblique viewing endoscope 300 according to Exemplary Embodiment 3.

Figure 29:
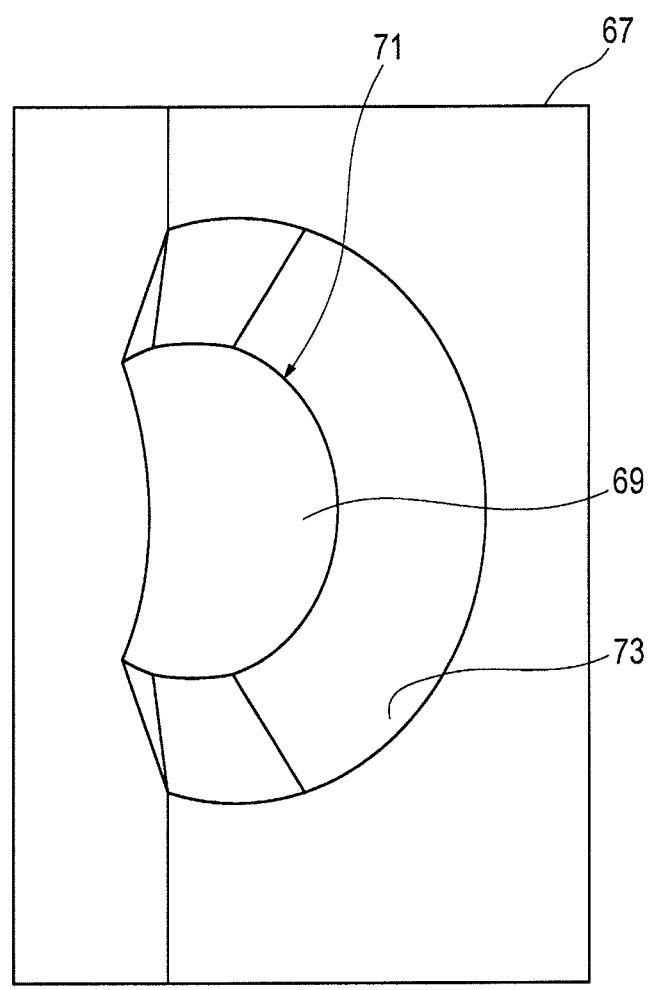
FIG. 29 is a perspective view of the front stage lens which is partially cut off in the oblique viewing endoscope according to Exemplary Embodiment 3.

FIG. 29 is a perspective view of front stage lens 67 which is partially cut off in oblique viewing endoscope 300 according to Exemplary Embodiment 3.

In front stage lens 67, lens surface 71 has convex curved surface 69 formed in a shape of a circular dome raised in a substantially spherical shape. As front stage lens 67, a spherical lens is illustrated as an example. However, the configuration is not limited thereto. Front stage lens 67 may have the free curve surface. Convex curved surface 69 of front stage lens 67 is formed in a bottom portion of tapered hole 73.

Figure 30:
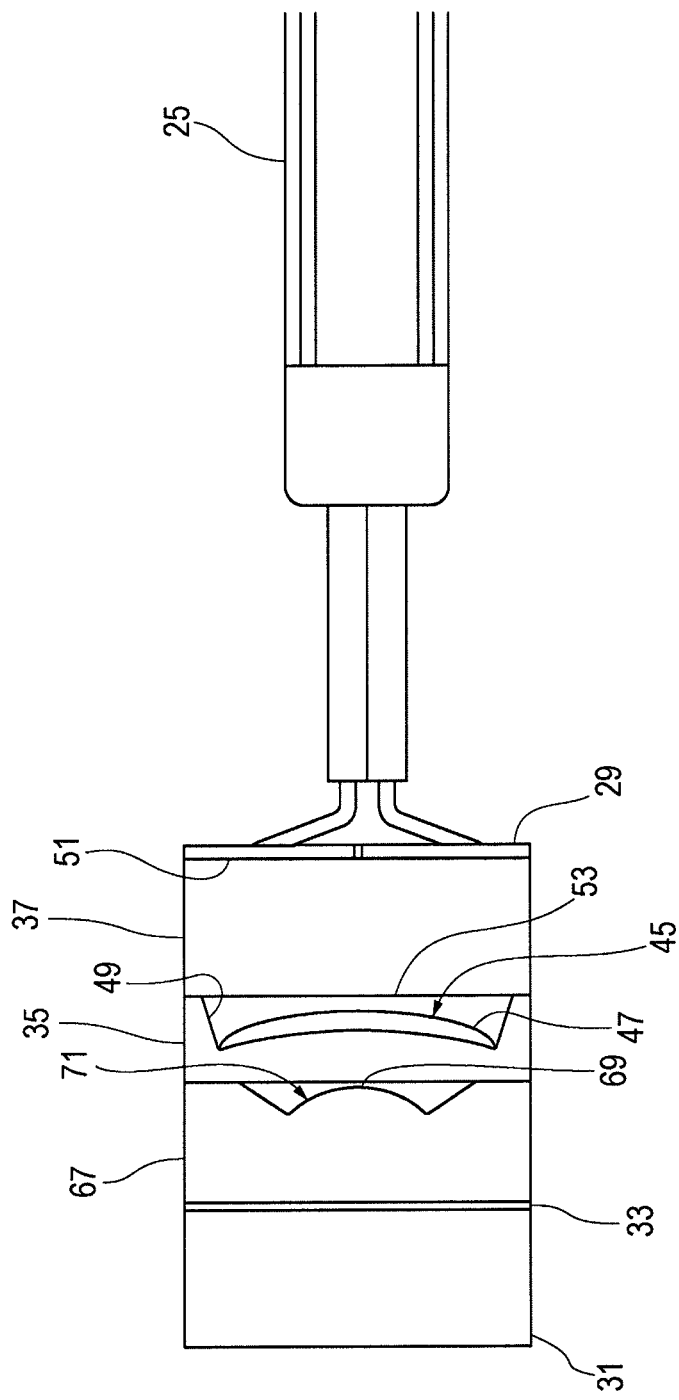
FIG. 30 is a planar sectional view of the oblique viewing endoscope according to Exemplary Embodiment 3.

FIG. 30 is a planar sectional view of oblique viewing endoscope 300 according to Exemplary Embodiment 3.

Lens 35 is bonded to front stage lens 67, thereby forming air layer 53 sealed in tapered hole 73 between lens surface 71 and lens 35. Since air layer 53 is formed in front stage lens 67, it is possible to increase a refractive index of the light emitted from lens surface 71 to air layer 53.

Figure 31:
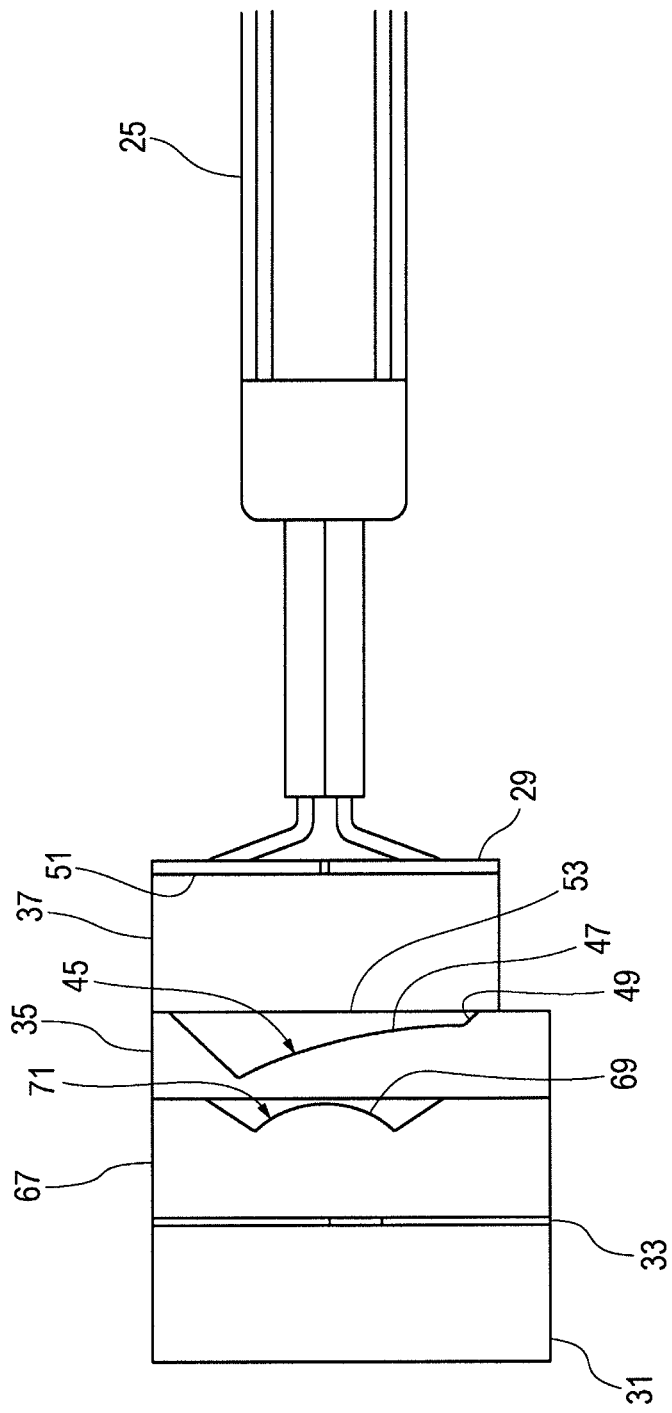
FIG. 31 is a lateral sectional view of the oblique viewing endoscope according to Exemplary Embodiment 3.

FIG. 31 is a lateral sectional view of oblique viewing endoscope 300 according to Exemplary Embodiment 3.

Front stage lens 67 is located so that the lens center (optical axis in front stage lens 67) is shifted upward above the opening of aperture 33. A relative position between the lens center of front stage lens 67 and aperture 33 is not limited thereto.

Next, an operation of the above-described configuration will be described.

Figure 32:
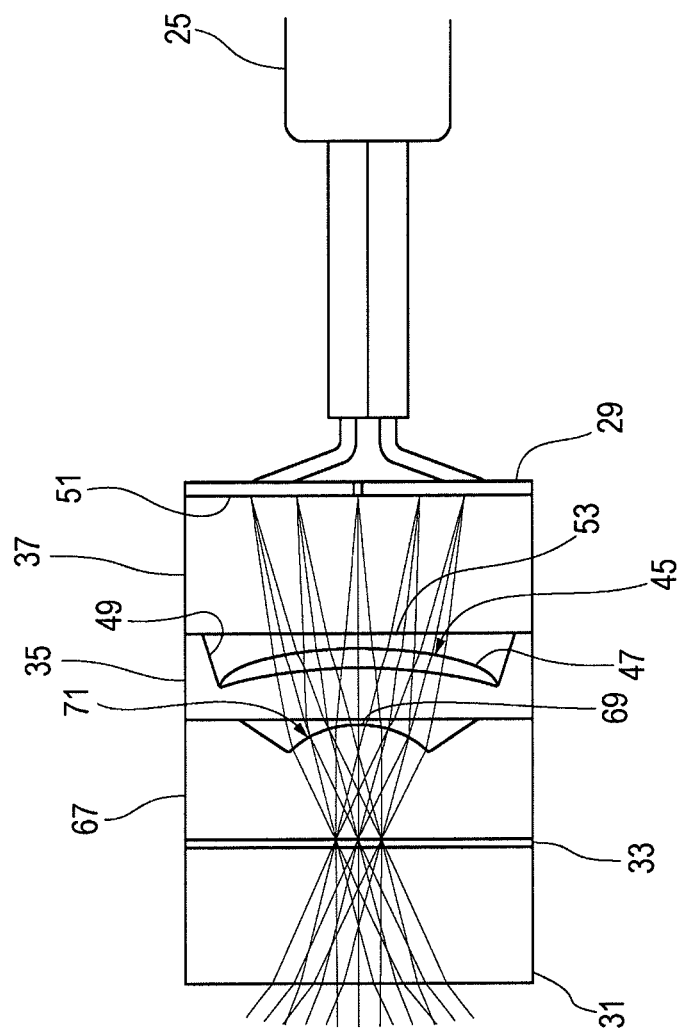
FIG. 32 is a ray tracing diagram in an optical system planar section of the oblique viewing endoscope according to Exemplary Embodiment 3.

FIG. 32 is a ray tracing diagram in an optical system planar section of the oblique viewing endoscope according to Exemplary Embodiment 3.

FIG. 33 is a ray tracing diagram in an optical system lateral section of the oblique viewing endoscope according to Exemplary Embodiment 3.

Oblique viewing endoscope 300 is configured to have two lenses such as front stage lens 67 close to the aperture and lens 35 close to the image plane. The aberration correction is shared by the lens surfaces so that front stage lens 67 close to the aperture mainly corrects spherical aberration and lens 35 close to the image plane mainly corrects distortion. In this manner, more advanced aberration correction can be performed, and the image forming performance can be improved.

Exemplary Embodiment 4

Next, Exemplary Embodiment 4 will be described. In Exemplary Embodiment 4, the same reference numerals will be given to members the same as the members described in Exemplary Embodiment 1, and repeated description will be omitted.

Figure 34:
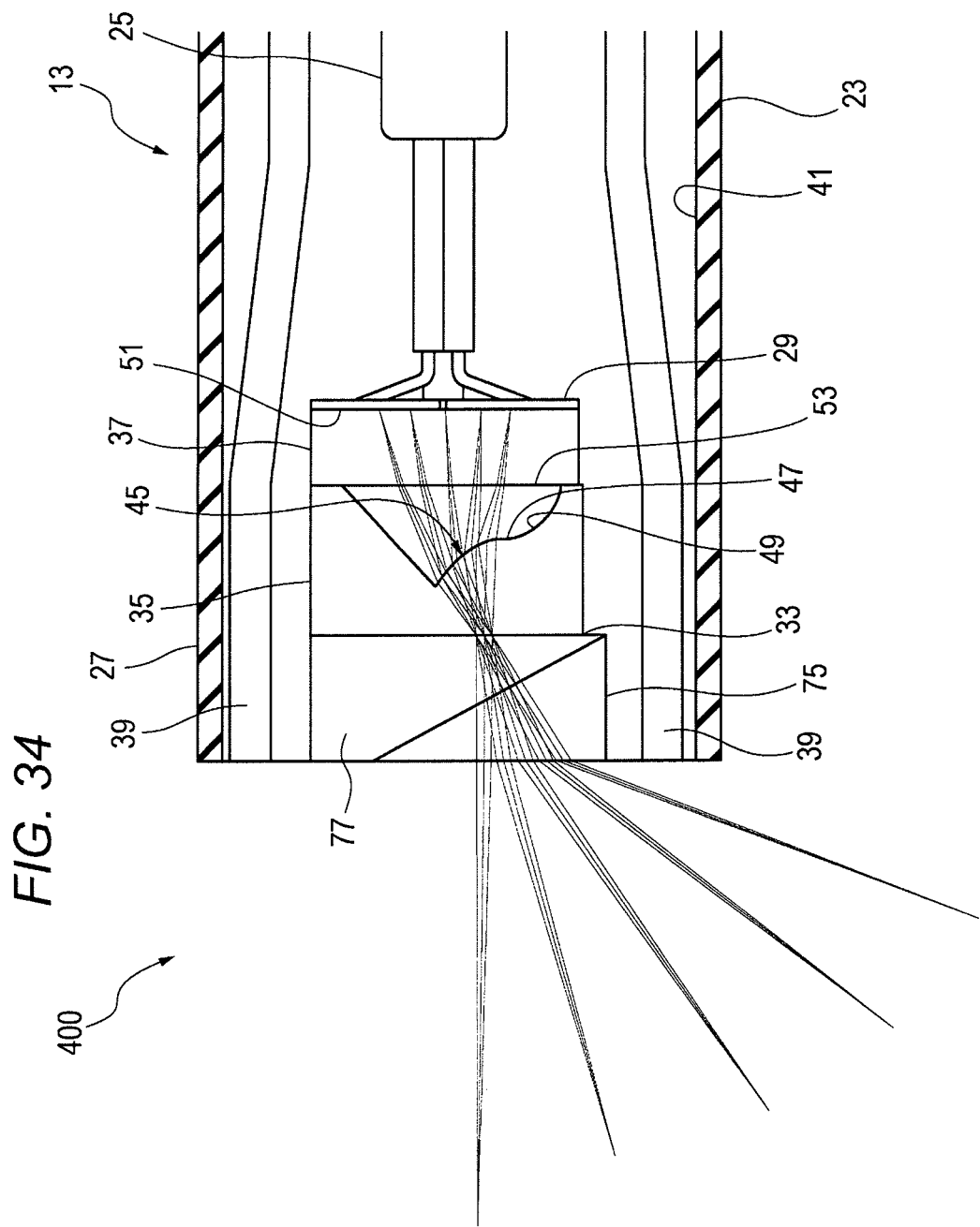
FIG. 34 is a ray tracing diagram in an optical system lateral section of an oblique viewing endoscope according to Exemplary Embodiment 4.

FIG. 34 is a ray tracing diagram in an optical system lateral section of oblique viewing endoscope 400 according to Exemplary Embodiment 4.

In oblique viewing endoscope 400 according to Exemplary Embodiment 4, in order to reduce the magnification chromatic aberration, a pair of prism 75 and prism 77 is located together on the objective side of lens 35. Each of the pair of prism 75 and prism 77 is a deflection angle prism on which the incident light is not reflected and which refracts the incident light. The pair of prism 75 and prism 77 is in close contact with a mating surface. The light vertically emitted from the light emitting surface of prism 75 is vertically incident on the light incident surface of prism 77.

According to oblique viewing endoscope 400, a difference between a refractive index and a dispersion rate can be utilized by locating the pair of prism 75 and prism 77 having mutually different refractive indexes and dispersion rates on the objective side with respect to lens 35. Oblique viewing endoscope 400 can reduce the chromatic aberration relative to a portion of the magnification chromatic aberration occurring in lens 35 by utilizing the difference between the refractive index and the dispersion rate. In oblique viewing endoscope 400, prism 75 and prism 77 having the mutually different dispersion rates are combined with each other on the front side of aperture 33 so as to correct the chromatic aberration caused by the deflection angle, and a substantially parallel optical system is inserted. In this manner, the color drift at the center of the screen can be corrected. In oblique viewing endoscope 400, the pair of prism 75 and prism 77 can be substituted for a cover glass.

Modification Example

Next, a modification example of Exemplary Embodiment 1 will be described. Illustration of this modification example will be omitted.

An oblique viewing endoscope according to the modification of Exemplary Embodiment 1 further has a refracting cover glass in the distal end on the objective side. This refracting cover glass is located perpendicular to the principal ray in the visual field direction by disposing an air layer between the refracting cover glass and objective cover glass 31. That is, in order to eliminate central image skipping, the oblique viewing endoscope according to the modification example is configured so that the additional refracting cover glass is tilted as large as the oblique viewing angle.

If oblique viewing endoscope 100 according to Exemplary Embodiment 1 obliquely views the object as large as 30° in the air, oblique viewing endoscope 100 obliquely views the object as large as 22° under the water. The viewing angle is changed around the frontal ray which is vertically incident on the cover glass. Accordingly, if oblique viewing endoscope 100 enters the water, the center is shifted. On the other hand, if the magnification chromatic aberration is corrected based on the air, the magnification chromatic aberration is excessively corrected under the water.

Therefore, the oblique viewing endoscope according to the modification example has the refracting cover glass on which the principal ray at the center of light receiving plane 51 is vertically incident. In this refracting cover glass, for example, a parallel flat plate or a dome glass is located in front of distal end portion 27.

According to the oblique viewing endoscope of this modification example, the refracting cover glass is obliquely located so as to be vertical to the principal ray in the visual field direction. In this manner, the principal ray at the center of light receiving plane 51 is vertically incident. Accordingly, even if the oblique viewing endoscope is in the air and under the water, it is possible to suppress movement of a central image.

Therefore, according to oblique viewing endoscope 100, oblique viewing endoscope 200, oblique viewing endoscope 300, and oblique viewing endoscope 400 of the present exemplary embodiment, the oblique viewing endoscope can be miniaturized and the visual field direction can be obliquely set, while the number of components is minimized.

Hereinafter, numerical value examples for specifically embodying a projection optical system according to Exemplary Embodiments 1, 2, and 4 will be described. In the following, Numerical Value Example 1 corresponds to Exemplary Embodiment 1 described above, Numerical Value Example 2 corresponds to Exemplary Embodiment 4 described above, and Numerical Value Example 3 corresponds to Exemplary Embodiment 2 described above. The optical configurations of Numerical Value Examples 1, 2, and 3 (FIGS. 35, 36, 44, and 52) respectively represent the optical configurations of corresponding Exemplary Embodiments 1, 4, and 2.

In each of the numerical value examples, the units of length in the table are all "mm", and the units of the viewing angle are all "°". In each of the numerical value examples, r represents the radius of curvature, d represents spacing (distance to the rear surface), nd represents the refractive index with respect to d-line, and vd represents an Abbe number with respect to the d-line. In each of the numerical value examples, a surface marked with an asterisk in the rear of the surface number is the free curve surface, and a shape of the free curve surface is defined by the following equation using a localized orthogonal coordinate system (x, y, and z) whose origin is a surface vertex. Here, x is set to the rightward-leftward direction when the lens is viewed from the object, y is set to the upward-downward direction, and z is set to a direction orthogonal to x and y.

Equation 1

$$Z = \frac{cr^2}{1 + \sqrt{1 - (1+k)c^2 r^2}} + \sum_{j=2}^{66} C_j x^m y^n \qquad (1)$$

Equation 2

$$j = \frac{(m+n)^2 + m + 3n}{2} + 1 \qquad (2)$$

Here,

Z: Sag amount of Surface Parallel to z-axis r: Distance in Radial Direction ($=\sqrt{(x^2 \pm y^2)}$)

c: Curvature at Surface Vertex k: Conic Constant

Cj: Coefficient of Monomial $x^m y^n$

In each of the following data, for the sake of convenience, the term of the i-th order of x which is a free curve surface coefficient in a polynomial, and the term of the j-th order of y are described as xiyj. For example, "X2Y" indicates the free curve surface coefficient of the term of the second order of x in the polynomial and the term of the first order of y.

Figure 35:
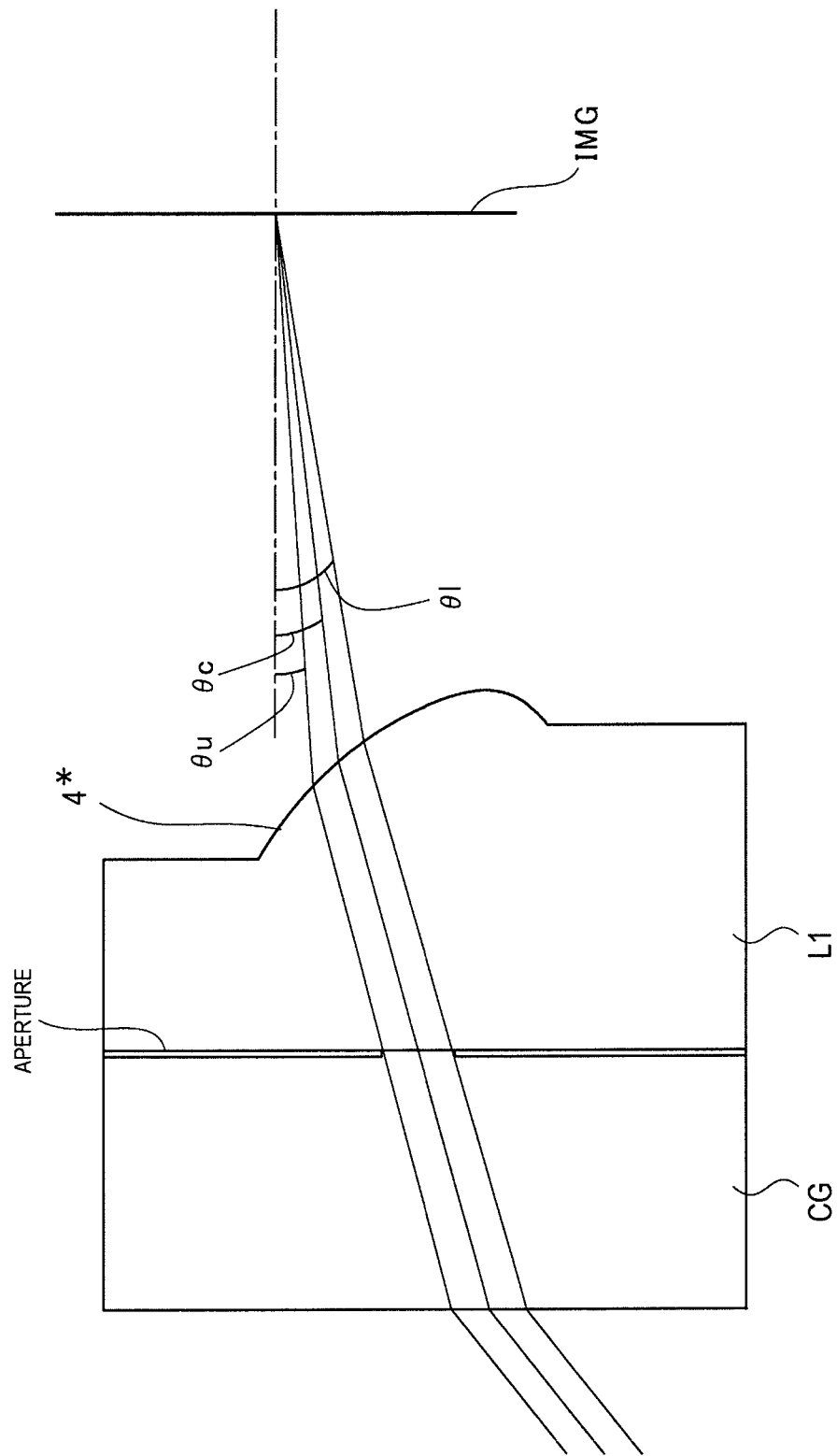
FIG. 35 is a view for describing each incident angle of rays incident on an image sensor (that is, an imaging element) according to numerical value examples.

FIG. 35 is a view for describing incident angles θc, θu, and θ1 of the rays incident on an image sensor (that is, imaging element 29) according to numerical value examples.

In FIG. 35, CG represents the cover glass (that is, objective cover glass 31), L1 represents the lens (that is, lens 35) having the free curve surface, SG represents a sensor cover glass (that is, element cover glass 37), and IMG represents an image sensor (that is, imaging element 29), respectively.

In Table 1, in each of Numerical Value Examples 1, 2, and 3, the incident angles of the principal ray, the upward ray in the y-direction, and the downward ray in the y-direction which are incident on the center of the image sensor are respectively illustrated as θc, θu, and θ1. The effective F-number derived from θu and θ1 is described as Fey. In Table 1, the numerical value examples are abbreviated as "examples". In any one of the numerical value examples, the incident angle θc of the principal ray is 5° or smaller, and efficiency of image sensor IMG (in other words, refer to design value characteristic 60 of the incident light illustrated in FIG. 12) is utilized (in other words, a characteristic substantially equivalent to characteristic 60 is obtained without greatly deviating from characteristic 60) so as to perform design.

TABLE 1

F Number in Respective Numerical Value Examples

|  | Example 1 | Example 2 | Example 3 |
|---|---|---|---|
| θc | 4.799 | 4.799 | 4.734 |
| θu | 1.507 | 1.507 | −0.804 |

TABLE 1-continued

F Number in Respective Numerical Value Examples

|  | Example 1 | Example 2 | Example 3 |
|---|---|---|---|
| θl | 7.740 | 7.740 | 10.252 |
| Fey | 9.20 | 9.20 | 5.19 |

Numerical Value Example 1

Figure 36:
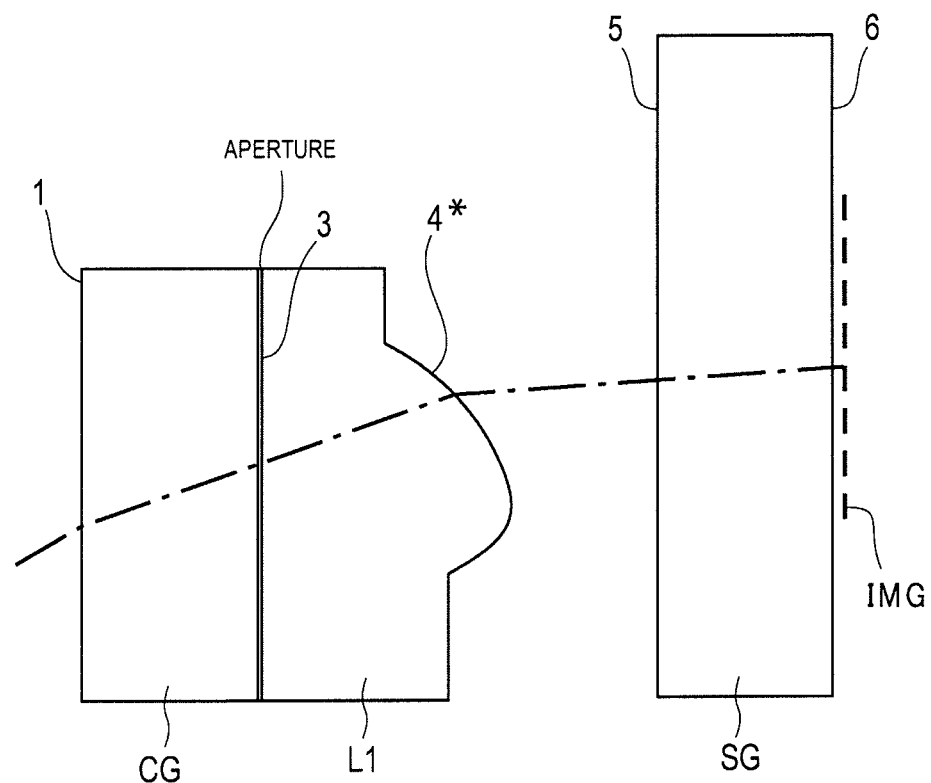
FIG. 36 is a sectional configuration diagram for describing an imaging optical system according to Numerical Value Example E

FIG. 36 is a sectional configuration diagram for describing an imaging optical system according to Numerical Value Example 1. In the drawing, reference numerals 1 to 6 represent surface numbers.

The rays emitted from a point on a dashed line of an object surface are refracted by cover glass CG, are transmitted through the aperture, are focused by lens L1 having the positive power, and form an image at the center of image sensor IMG.

Figure 37:
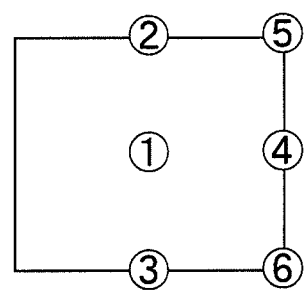
FIG. 37 is a view for describing each coordinate position on the image sensor which is viewed from an image side, in the configuration diagram illustrated in FIG. 36.

FIG. 37 is a view for describing an example in which respective coordinate positions on the image sensor which are viewed from the image side in the configuration diagram illustrated in FIG. 36 are illustrated using white circle 1 to white circle 6.

Figure 38:
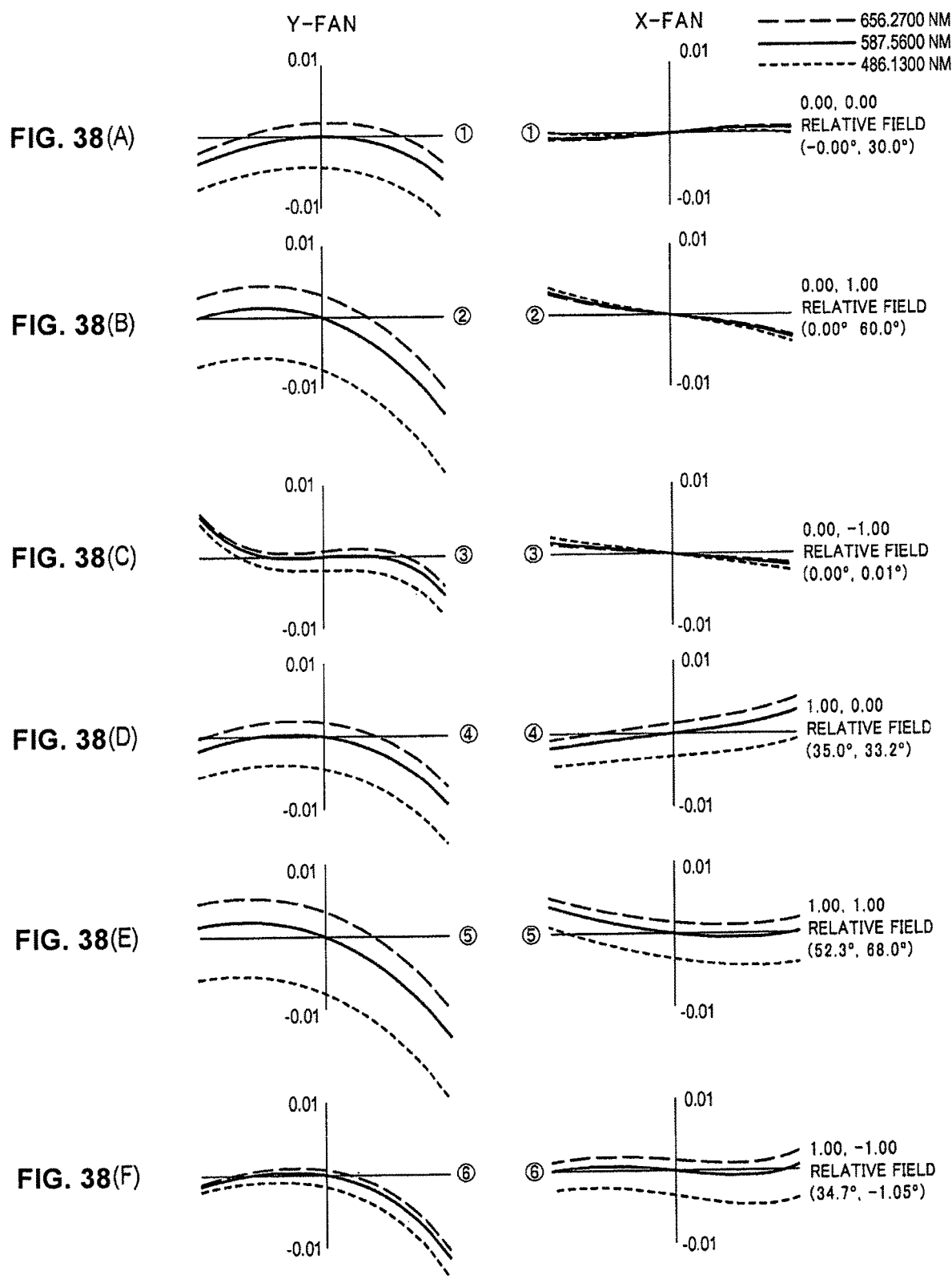
FIG. 38(A) is a transverse aberration diagram in an x, y-direction in white circle 1 at each coordinate position according to Numerical Value Example 1.
FIG. 38(B) is a transverse aberration diagram in the x, y-direction in white circle 2 at each coordinate position according to Numerical Value Example 1.
FIG. 38(C) is a transverse aberration diagram in the x, y-direction in white circle 3 at each coordinate position according to Numerical Value Example 1.
FIG. 38(D) is a transverse aberration diagram in the x, y-direction in white circle 4 at each coordinate position according to Numerical Value Example 1.
FIG. 38(E) is a transverse aberration diagram in the x, y-direction in white circle 5 at each coordinate position according to Numerical Value Example 1.
FIG. 38(F) is a transverse aberration diagram in the x, y-direction in white circle 6 at each coordinate position according to Numerical Value Example 1.

FIGS. 38(A) to 38(F) are transverse aberration diagrams in x, y-direction in white circle 1 to white circle 6 at respective coordinate positions according to Numerical Value Example 1. FIG. 38(A) is a transverse aberration diagram in the x, y-direction in white circle 1 at each coordinate position according to Numerical Value Example 1. FIG. 38(B) is a transverse aberration diagram in the x, y-direction in white circle 2 at each coordinate position according to Numerical Value Example 1. FIG. 38(C) is a transverse aberration diagram in the x, y-direction in white circle 3 at each coordinate position according to Numerical Value Example 1. FIG. 38(D) is a transverse aberration diagram in the x, y-direction in white circle 4 at each coordinate position according to Numerical Value Example 1. FIG. 38(E) is a transverse aberration diagram in the x, y-direction in white circle 5 at each coordinate position according to Numerical Value Example 1. FIG. 38(F) is a transverse aberration diagram in the x, y-direction in white circle 6 at each coordinate position according to Numerical Value Example 1. A solid line represents a characteristic of the d-line (0.588 μm), a short broken line represents a characteristic of an F-line (0.486 μm), and a long broken line represents a characteristic of a C-line (0.656 μm). Y-FAN is the transverse aberration in the y-direction, and X-FAN is the transverse aberration in the x-direction.

The vertical axis in FIGS. 38(A) to 38(F) represents a transverse aberration amount (mm). In FIGS. 38(A) to 38(F), a maximum scalar value of the transverse aberration amount is ±0.01 mm. The value of ±0.01 mm means that a highest portion of the vertical axis is +0.01 mm and a lowest portion of the vertical axis is −0.01 mm. The horizontal axis in FIGS. 38(A) to 38(F) represents a relative pupil height, and the horizontal axis in the drawing on the left side of transverse aberration diagrams arranged two by two represents relative pupil height y in the y-direction, and the horizontal axis in the drawing on the right side represents relative pupil height x in the x-direction (similarly applicable to the following numerical value examples).

Table 2 and Table 3 below show specific data of an imaging optical system according to Numerical Value Example 1. In Numerical Value Example 1, the center of the image has an angle of approximately 60° in the y-direction (upward-downward direction of the drawing paper), and the viewing angle in the y-direction is approximately 60°. The object surface is obtained on the assumption of an observation target for endoscopic use, and it is assumed that the observation target has a hemispheric shape having a radius of 3.2 mm, which is located 3 mm ahead of the first surface. Eccentricity Y in the table represents a shift amount shifted in the y-direction. In the table, tilt α represents an in-plane rotation amount (similarly applicable to the following numerical value examples). Table 2 below shows the surface data of each optical element according to Numerical Value Example 1.

TABLE 2

Surface Data of Numerical Value Example 1

| Surface No. | | r (Y Radius of Curvature) | d | nd | vd | Eccentricity Y | Tilt α | Remarks |
|---|---|---|---|---|---|---|---|---|
| Object Surface | | 3.2 | 3.000 | | | | | |
| 1 | | Unlimited | 0.400 | 1.51680 | 64.20 | | | |
| Aperture | | Unlimited | 0.010 | 1.58144 | 40.85 | −0.045 | | Only surface is eccentric |
| 3 | | Unlimited | 0.560 | 1.50900 | 55.00 | −0.045 | | Only surface is eccentric |
| 4 | Free Curve Surface | −0.1107 | 0.343 | | | | | |
| 5 | | Unlimited | 0.400 | 1.51680 | 64.20 | −0.264 | | Only surface is eccentric |
| 6 Image Surface | | Unlimited | 0.010 | | | | | |

Hereinafter, Table 3 shows free curve surface data.

TABLE 3

Free Curve Surface Data of Numerical Value Example 1

| Coefficient | Order | Fourth Surface |
|---|---|---|
| k | 0 | −9.6424E−01 |
| C3 | Y | −2.9033E−01 |
| C4 | X2 | 2.7195E+00 |

TABLE 3-continued

Free Curve Surface Data of Numerical Value, Example 1

| Coefficient | Order | Fourth Surface |
|---|---|---|
| C6 | Y2 | 2.4616E+00 |
| C8 | X2Y | 1.4817E+00 |
| C10 | Y3 | 9.2481E+00 |
| C11 | X4 | 9.4416E+00 |
| C13 | X2Y2 | 6.8917E+00 |
| C15 | Y4 | −4.1793E+01 |
| C17 | X4Y | −3.5190E+01 |
| C19 | X2Y3 | −1.7135E+02 |
| C22 | X6 | −1.8473E+02 |
| C24 | X4Y2 | 1.5922E+02 |
| C26 | X2Y4 | 1.0876E+03 |
| C28 | Y6 | 4.5138E+02 |
| C30 | X6Y | 8.9015E+01 |
| C32 | X4Y3 | −9.5835E+02 |
| C34 | X2Y5 | −2.4516E+03 |
| C36 | Y7 | −8.4082E+02 |

Numerical Value Example 2

Figure 39:
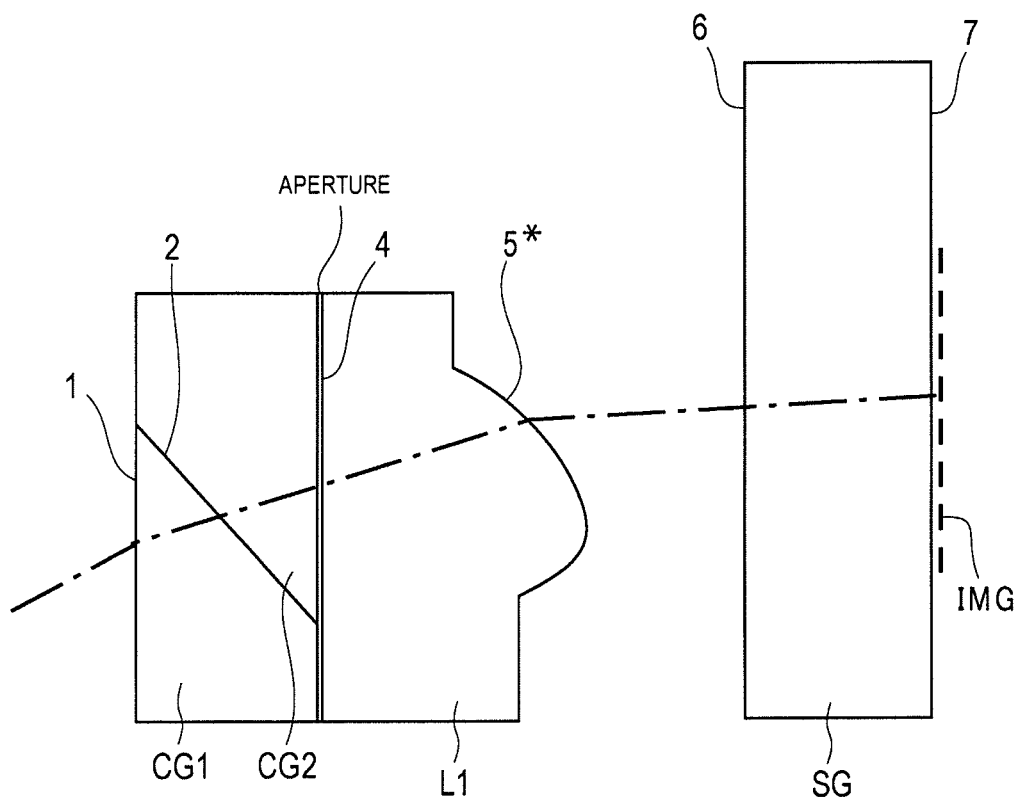
FIG. 39 is a sectional configuration diagram for describing an imaging optical system according to Numerical Value Example 2.

FIG. 39 is a sectional configuration diagram for describing an imaging optical system according to Numerical Value Example 2. In the drawing, the reference numerals of 1 to 7 represent surface numbers.

The rays emitted from a point on a dashed line of an object surface are refracted by cover glass CG1 and cover glass CG2, are transmitted through the aperture, are focused by lens L1 having the positive power, and form an image at the center of image sensor IMG.

Figure 40:
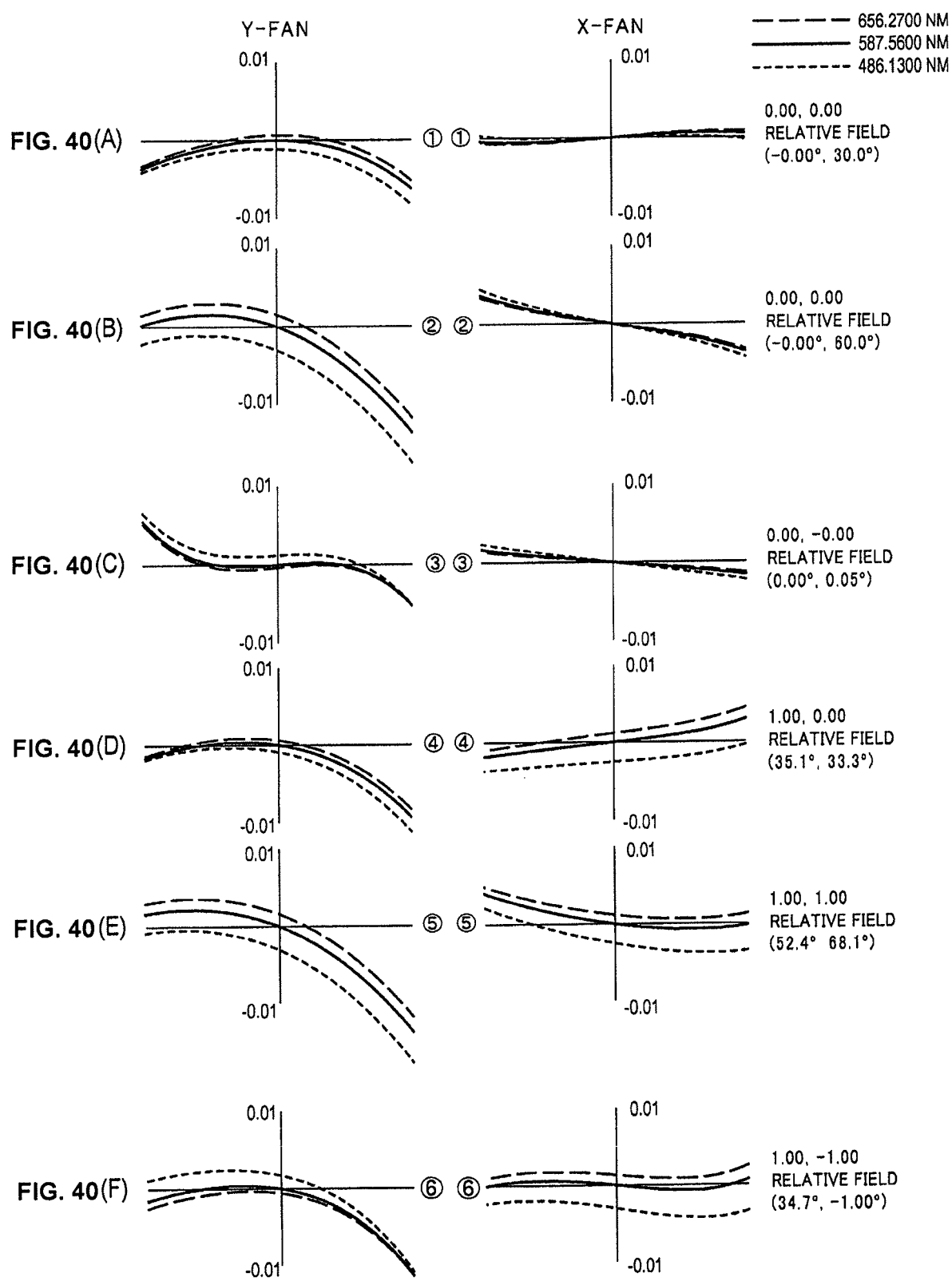
FIG. 40(A) is a transverse aberration diagram in the x, y-direction in white circle 1 at each coordinate position according to Numerical Value Example 2.
FIG. 40(B) is a transverse aberration diagram in the x, y-direction in white circle 2 at each coordinate position according to Numerical Value Example 2.
FIG. 40(C) is a transverse aberration diagram in the x, y-direction in white circle 3 at each coordinate position according to Numerical Value Example 2.
FIG. 40(D) is a transverse aberration diagram in the x, y-direction in white circle 4 at each coordinate position according to Numerical Value Example 2.
FIG. 40(E) is a transverse aberration diagram in the x, y-direction in white circle 5 at each coordinate position according to Numerical Value Example 2.
FIG. 40(F) is a transverse aberration diagram in the x, y-direction in white circle 6 at each coordinate position according to Numerical Value Example 2.

FIGS. 40(A) to 40(F) are transverse aberration diagrams in x, y-direction in white circle 1 to white circle 6 at respective coordinate positions according to Numerical Value Example 2. FIG. 40(A) is a transverse aberration diagram in the x, y-direction in white circle 1 at each coordinate position according to Numerical Value Example 2. FIG. 40(B) is a transverse aberration diagram in the x, y-direction in white circle 2 at each coordinate position according to Numerical Value Example 2. FIG. 40(C) is a transverse aberration diagram in the x, y-direction in white circle 3 at each coordinate position according to Numerical Value Example 2. FIG. 40(D) is a transverse aberration diagram in the x, y-direction in white circle 4 at each coordinate position according to Numerical Value Example 2. FIG. 40(E) is a transverse aberration diagram in the x, y-direction in white circle 5 at each coordinate position according to Numerical Value Example 2. FIG. 40(F) is a transverse aberration diagram in the x, y-direction in white circle 6 at each coordinate position according to Numerical Value Example 2. The solid line represents the characteristic of the d-line (0.588 μm), the short broken line represents the characteristic of the F-line (0.486 μm), and the long broken line represents the characteristic of the C-line (0.656 μm). Y-FAN is the transverse aberration in the y-direction, and X-FAN is the transverse aberration in the x-direction.

Table 4 and Table 5 below show specific data of an imaging optical system according to Numerical Value Example 2. Similar to Numerical Value Example 1, in Numerical Value Example 2, the center of the image has an angle of approximately 60° in the y-direction (upward-downward direction of the drawing paper), and the viewing angle in the y-direction is approximately 60°. The object surface is obtained on the assumption of the observation target for endoscopic use, and it is assumed that the observation target has the hemispheric shape having the radius of 3.2 mm, which is located 3 mm ahead of the first surface. A shape of each surface is the same as that according to Numerical Value Example 1. However, the chromatic aberration is reduced by configuring cover glass CG1 and cover glass CG2 so as to include two prisms.

Table 4 shows the surface data of each optical element according to Numerical Value Example 2.

TABLE 4

Surface Data of Numerical Value Example 2

| Surface No. | | r (Y Radius of Curvature) | d | nd | vd | Eccentricity Y | Tilt α | Remarks |
|---|---|---|---|---|---|---|---|---|
| Object Surface | | 3.2 | 3.000 | | | | | |
| 1 | | Unlimited | 0.200 | 1.59349 | 67.00 | | 40.000 | Only surface is eccentric |
| 2 | | Unlimited | 0.200 | 1.59270 | 35.44 | | −40.000 | Only surface is eccentric |
| Aperture | | Unlimited | 0.010 | 1.58144 | 40.85 | −0.045 | | Only surface is eccentric |
| 4 | | Unlimited | 0.560 | 1.50900 | 55.00 | −0.045 | | Only surface is eccentric |
| 5 | Free Curve Surface | −0.1107 | 0.343 | | | | | |
| 6 | | Unlimited | 0.400 | 1.51680 | 64.20 | −0.264 | | Only surface is eccentric |
| 7 Image Surface | | Unlimited | 0.010 | | | | | |

Hereinafter, Table 5 shows free curve surface data according to Numerical Value Example 2.

TABLE 5

Free Curve Surface Data of Numerical Value Example 2

| Coefficient | Order | Fifth Surface |
|---|---|---|
| k | 0 | −9.6424E−01 |
| C3 | Y | −2.9033E−01 |
| C4 | X2 | 2.7195E+00 |
| C6 | Y2 | 2.4616E+00 |
| C8 | X2Y | 1.4817E+00 |
| C10 | Y3 | 9.2481E+00 |
| C11 | X4 | 9.4416E+00 |
| C13 | X2Y2 | 6.8917E+00 |
| C15 | Y4 | −4.1793E+01 |
| C17 | X4Y | −3.5190E+01 |
| C19 | X2Y3 | −1.7135E+02 |
| C22 | X6 | −1.8473E+02 |
| C24 | X4Y2 | 1.5922E+02 |
| C26 | X2Y4 | 1.0876E+03 |
| C28 | Y6 | 4.5138E+02 |
| C30 | X6Y | 8.9015E+02 |
| C32 | X4Y3 | −9.5835E+02 |
| C34 | X2Y5 | −2.4516E+03 |
| C36 | Y7 | −8.4082E+02 |
| C37 | X8 | 1.3586E+03 |
| C39 | X6Y2 | 1.6423E+03 |
| C41 | X4Y4 | 8.8816E+02 |
| C43 | X2Y6 | 1.0545E+03 |

Numerical Value Example 3

Figure 41:
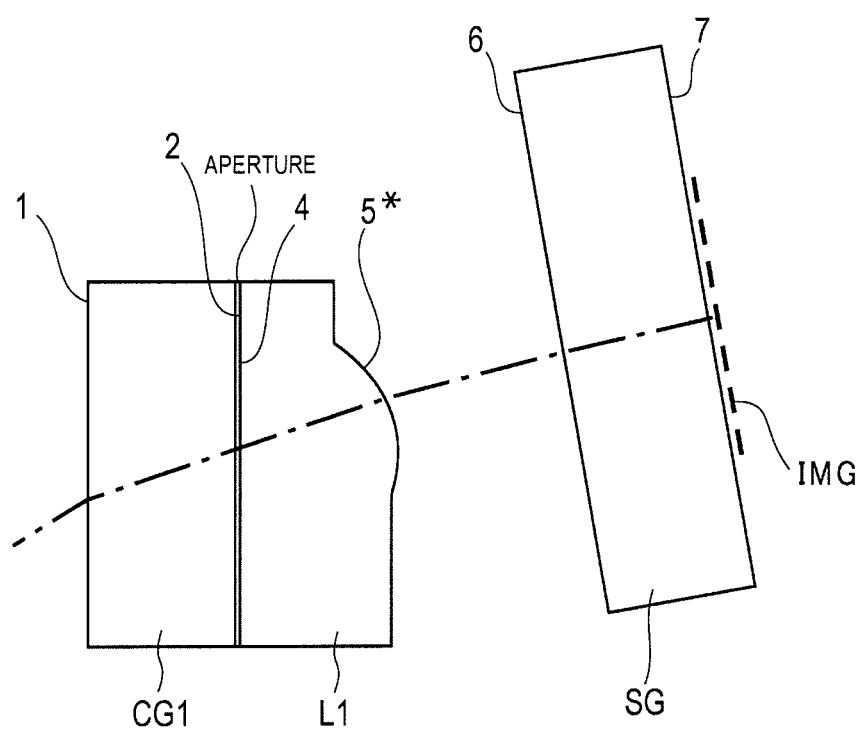
FIG. 41 is a sectional configuration diagram for describing an imaging optical system according to Numerical Value Example 3.

FIG. 41 is a sectional configuration diagram for describing an imaging optical system according to Numerical Value Example 3. In the drawing, the reference numerals of 1 to 7 represent surface numbers.

The rays emitted from a point on a dashed line of an object surface are refracted by cover glass CG1 and cover glass CG2, are transmitted through the aperture, are focused by lens L1 having the positive power, and form an image at the center of image sensor IMG.

Figure 42:
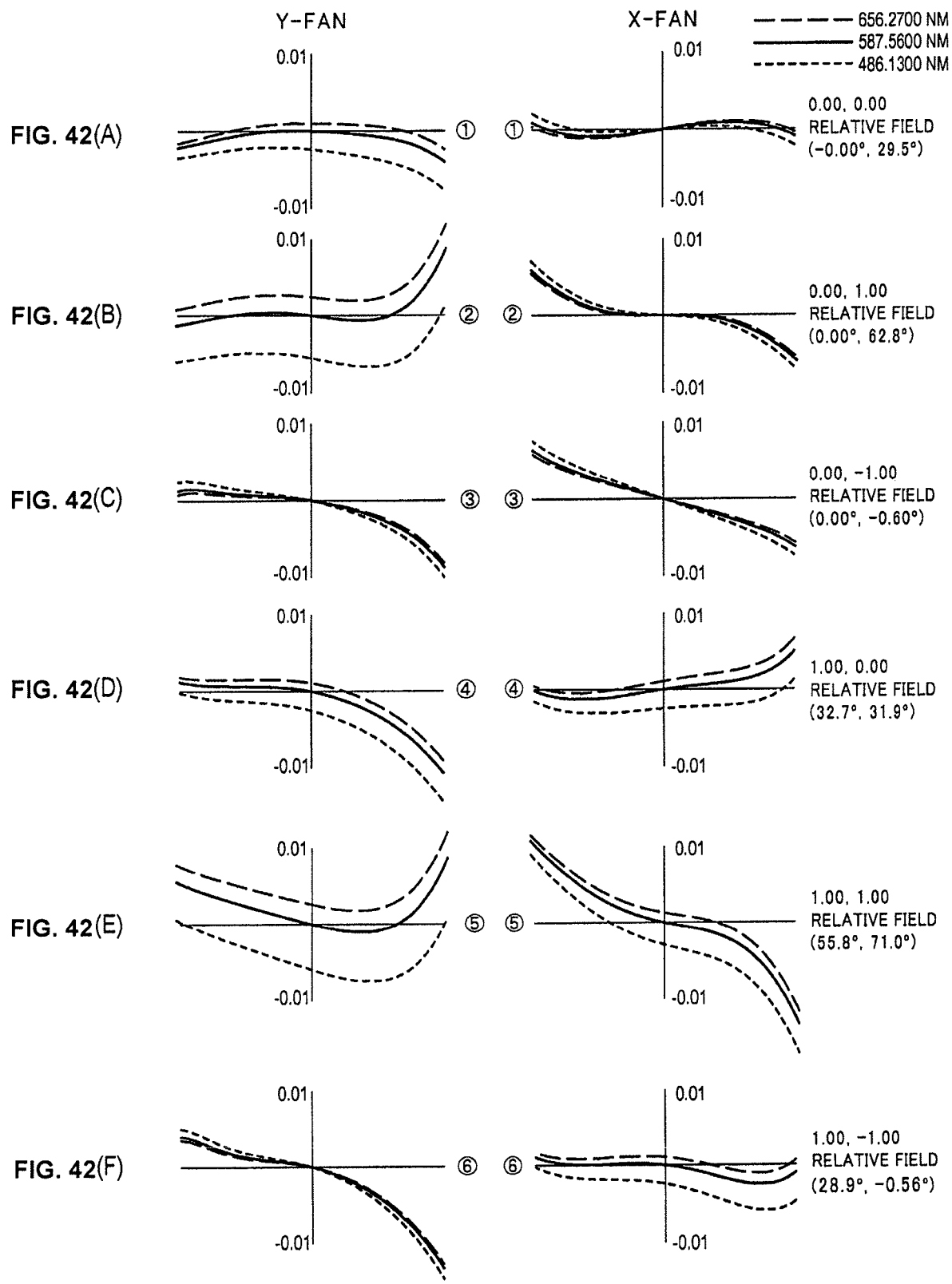
FIG. 42(A) is a transverse aberration diagram in the x, y-direction in white circle 1 at each coordinate position according to Numerical Value Example 3.
FIG. 42(B) is a transverse aberration diagram in the x, y-direction in white circle 2 at each coordinate position according to Numerical Value Example 3.
FIG. 42(C) is a transverse aberration diagram in the x, y-direction in white circle 3 at each coordinate position according to Numerical Value Example 3.
FIG. 42(D) is a transverse aberration diagram in the x, y-direction in white circle 4 at each coordinate position according to Numerical Value Example 3.
FIG. 42(E) is a transverse aberration diagram in the x, y-direction in white circle 5 at each coordinate position according to Numerical Value Example 3.
FIG. 42(F) is a transverse aberration diagram in the x, y-direction in white circle 6 at each coordinate position according to Numerical Value Example 3.
Figure 43:
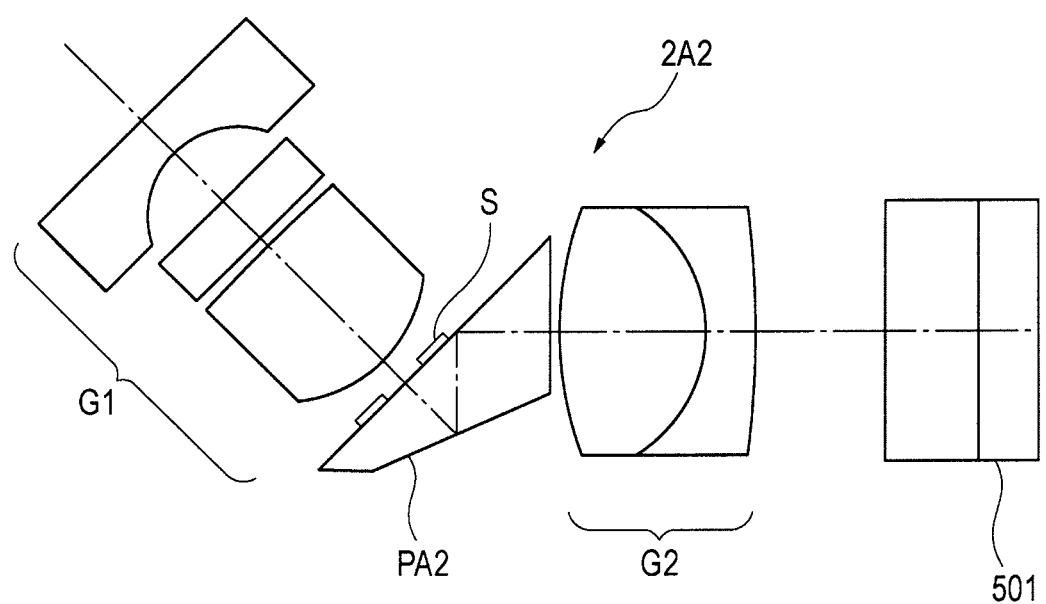
FIG. 43 is a layout view of a forward oblique viewing optical system in the related art.
Figure 44:
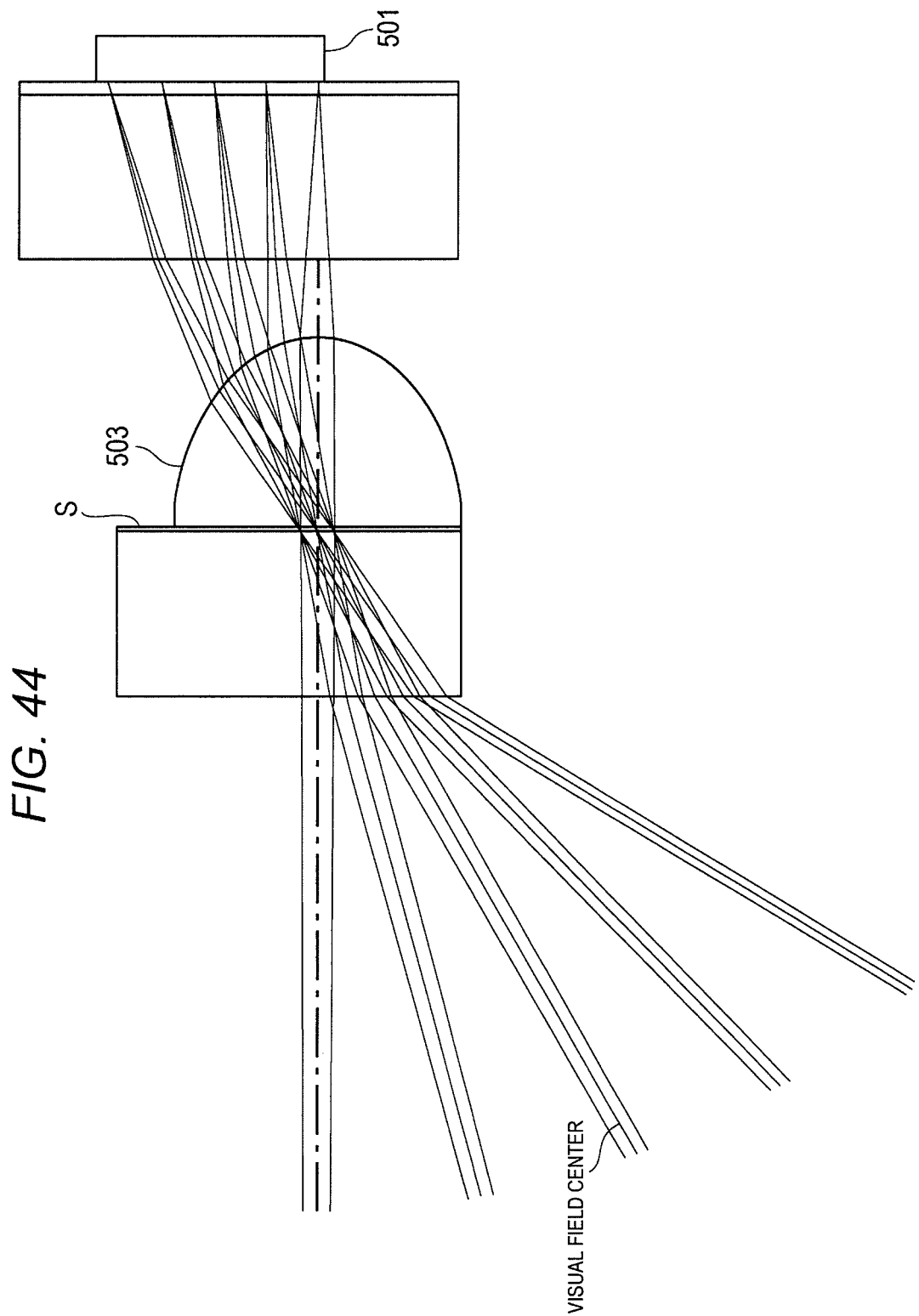
FIG. 44 is a plan view of an optical system in the related art, in which an imaging element is shifted in a horizontal direction.
Figure 45:
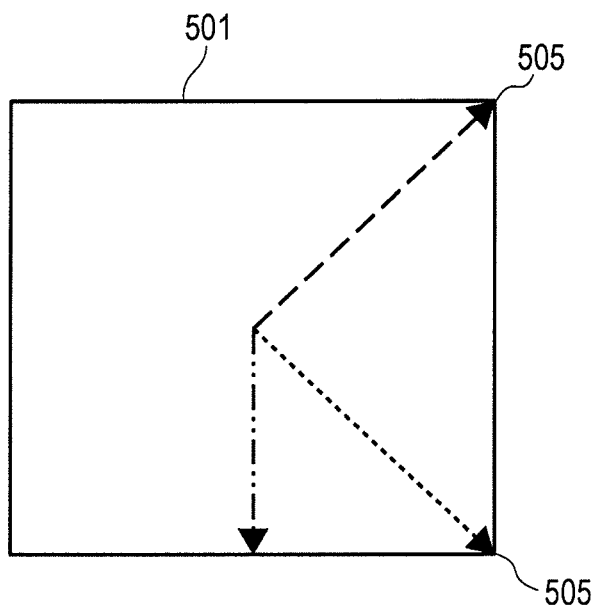
FIG. 45 a view for describing a ray example from a center of an imaging plane to each periphery in the shifted imaging element.

FIGS. 42(A) to 42(F) are transverse aberration diagrams in x, y-direction in white circle 1 to white circle 6 at respective coordinate positions according to Numerical Value Example 3. FIG. 42(A) is a transverse aberration diagram in the x, y-direction in white circle 1 at each coordinate position according to Numerical Value Example 3. FIG. 42(B) is a transverse aberration diagram in the x, y-direction in white circle 2 at each coordinate position according to Numerical Value Example 3. FIG. 42(C) is a transverse aberration diagram in the x, y-direction in white circle 3 at each coordinate position according to Numerical Value Example 3. FIG. 42(D) is a transverse aberration diagram in the x, y-direction in white circle 4 at each coordinate position according to Numerical Value Example 3. FIG. 42(E) is a transverse aberration diagram in the x, y-direction in white circle 5 at each coordinate position according to Numerical Value Example 3. FIG. 42(F) is a transverse aberration diagram in the x, y-direction in white circle 6 at each coordinate position according to Numerical Value Example 3. The solid line represents the characteristic of the d-line (0.588 μm), the short broken line represents the characteristic of the F-line (0.486 μm), and the long broken line represents the characteristic of the C-line (0.656 μm). Y-FAN is the transverse aberration in the y-direction, and X-FAN is the transverse aberration in the x-direction.

Table 6 and Table 7 below show specific data of an imaging optical system according to Numerical Value Example 3. In Numerical Value Example 3, the center of the image has an angle of approximately 60° in the y-direction (upward-downward direction of the drawing paper), and the viewing angle in the y-direction is approximately 60°. The object surface is obtained on the assumption of the observation target for endoscopic use, and it is assumed that the observation target is a surface tilting as much as 30°, which is located 3.5 mm ahead of the first surface.

Table 6 below shows the surface data of each optical element according to Numerical Value Example 3.

TABLE 6

Surface Data of Numerical Value Example 3

| Surface No. | | r (Y-Radius of Curvature) | d | nd | vd | Eccentricity y | Tilt α | Remarks |
|---|---|---|---|---|---|---|---|---|
| Object Surface | | Unlimited | 0.000 | | | | 30.0 | Only surface is eccentric |
| 1 | | Unlimited | 3.500 | | | | | |
| 2 | | Unlimited | 0.400 | 1.51680 | 64.20 | | | |
| Aperture | | Unlimited | 0.010 | 1.58144 | 40.85 | −0.0378 | | Only surface is eccentric |
| 4 | | Unlimited | 0.430 | 1.50900 | 55.00 | −0.0378 | | Only surface is eccentric |
| 5 | Free Curve Surface | −0.1974 | 0.450 | | | | | |
| 6 | | Unlimited | 0.400 | 1.51680 | 64.20 | 0.0328 | 10.0 | Only surface is eccentric |
| 7 Image Surface | | Unlimited | 0.010 | | | | | |

Hereinafter, Table 7 shows free curve surface data according to Numerical Value Example 3.

TABLE 7

Free Curve Surface Data of Numerical Value Example 3

| Coefficient | Order | Fifth Surface |
|---|---|---|
| k | 0 | −1.0000E+00 |
| C3 | Y | 6.6350E−02 |
| C4 | X2 | 9.8558E−01 |
| C6 | Y2 | 1.0145E+00 |
| C8 | X2Y | −1.2050E+00 |
| C10 | Y3 | −1.4650E−01 |
| C11 | X4 | 8.3035E−01 |
| C13 | X2Y2 | 1.0212E+01 |
| C15 | Y4 | −4.1802E+00 |
| C17 | X4Y | 1.0103E+02 |
| C19 | X2Y3 | −2.6731E+00 |
| C22 | X6 | −8.7526E+01 |
| C24 | X4Y2 | −1.0204E+03 |
| C26 | X2Y4 | −4.9819E+02 |
| C28 | Y6 | 1.4016E+03 |
| C30 | X6Y | −31716E+03 |
| C32 | X4Y3 | 2.2782E+03 |
| C34 | X2Y5 | −8.1074E+02 |
| C36 | Y7 | −1.7704E+04 |
| C37 | X8 | 8.4523E+02 |
| C39 | X6Y2 | 2.4780E+04 |
| C41 | X4Y4 | 5.5849E+03 |
| C43 | X2Y6 | 3.4564E+04 |
| C45 | Y8 | 8.9380E+04 |
| C47 | X8Y | 3.2845E+04 |
| C49 | X6Y3 | −3.5840E+04 |
| C51 | X4Y5 | −5.0915E+04 |
| C53 | X2Y7 | −1.5267E+05 |
| C55 | Y9 | −2.0709E+05 |
| C58 | X8Y2 | −1.9452E+05 |
| C60 | X6Y4 | 1.8843E+04 |
| C62 | X4Y6 | 9.1723E+04 |
| C64 | X2Y8 | 2.0236E+05 |
| C66 | Y10 | 1.8278E+05 |

Hitherto, the exemplary embodiments and the numerical value examples have been described with reference to the drawings. However, as a matter of course, the present disclosure is not limited to the examples. Those skilled in the art will obviously appreciate that various modification examples or correction examples are conceivable within the scope described in the appended claims. Naturally, it will be understood that the modification examples or the correction examples fall within the technical scope of the present disclosure. The respective configuration elements in the above-described exemplary embodiments may be optionally combined with each other without departing from the gist of the invention.

The present disclosure has an effect of reducing the number of components, miniaturization, cost reduction, and weight reduction in the imaging device, and is usefully applicable to a small diameter oblique viewing endoscope used for medical surgery, for example.

What is claimed is:

1. An oblique viewing endoscope comprising:
   an aperture;
   a lens including a free curve surface having positive power; and
   an imaging element that captures an image formed by the lens including the free curve surface having the positive power,
   wherein rays passed through a center of the aperture and incident on a center of the imaging element are incident in an oblique viewing direction, are bent by the lens including the free curve surface having the positive power, and are vertically incident on the imaging element, and
   wherein the free curve surface is formed in an asymmetrical shape by using the center of the aperture as a boundary.

2. The oblique viewing endoscope of claim 1,
   wherein the lens has a rectangular outer shape.

3. The oblique viewing endoscope of claim 1,
   wherein the lens bends the rays so as to reduce an angle of the rays incident on the imaging element by causing a surface of the lens to have the positive power, and converges the rays on a light receiving plane of the imaging element so as to form an image, and
   wherein the surface of the lens is formed to serve as a single piece.

4. The oblique viewing endoscope of claim 1, further comprising:
   an element cover glass disposed between the lens and the imaging element,
   wherein the lens and the element cover glass are connected to each other via an adhesion resin.

5. An imaging system comprising:
   the oblique viewing endoscope of claim 1; and
   a correction processor that performs correction processing on an image signal imaged by the oblique viewing endoscope.

6. The oblique viewing endoscope of claim 1, wherein the free curve surface is formed using a continuously curved surface controlled so that a radius of curvature of an upper side portion of the free curve surface in a vertical direction gradually increases compared to a radius of curvature of a lower side portion thereof in the vertical direction.

7. The oblique viewing endoscope of claim 6, wherein in the free curve surface, a first distance between a first curved surface end disposed on an upper side in the vertical direction and the light receiving plane is longer than a second distance between a second curved surface end disposed on a lower side in the vertical direction and the light receiving plane.

* * * * *